(12) United States Patent
Buchanan et al.

(10) Patent No.: US 6,838,113 B1
(45) Date of Patent: Jan. 4, 2005

(54) INCREASING THE DIGESTIBILITY OF FOOD PROTEINS BY THIOREDOXIN REDUCTION

(75) Inventors: Bob B. Buchanan, Berkeley, CA (US); Gregorio del Val, Saint-Aubin (CH); Rosa M. Lozano, Madrid (ES); Jin-an Jiao, Ft. Lauderdale, FL (US); Joshua H. Wong, South San Francisco, CA (US); Boihon C. Yee, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/296,927

(22) Filed: Apr. 22, 1999

Related U.S. Application Data

(60) Division of application No. 08/953,703, filed on Oct. 17, 1997, now Pat. No. 5,952,034, which is a continuation-in-part of application No. 08/326,976, filed on Oct. 21, 1994, now Pat. No. 5,792,506, which is a continuation-in-part of application No. 08/211,673, filed as application No. PCT/US92/08595 on Oct. 8, 1992, now Pat. No. 6,113,951, which is a continuation-in-part of application No. 07/935,002, filed on Aug. 25, 1992, now abandoned, which is a continuation-in-part of application No. 07/776,109, filed on Oct. 12, 1991, now abandoned.

(51) Int. Cl.[7] ............................. A23L 1/29; A23L 3/358
(52) U.S. Cl. ....................... 426/656; 426/541; 426/549; 426/574; 426/615
(58) Field of Search ................................. 426/656, 541, 426/549, 574, 581, 615, 618; 424/94.4

(56) References Cited

U.S. PATENT DOCUMENTS

| 3,803,326 A | 4/1974 | Craig et al. .................... 426/21 |
| 4,405,648 A | 9/1983 | Atsumi et al. ................. 426/19 |
| 5,028,419 A | 7/1991 | Pigiet ........................... 424/71 |

FOREIGN PATENT DOCUMENTS

| GB | 1 400 972 | 7/1975 |
| GB | 1 420 843 | 1/1976 |
| WO | 96/12799 | 5/1996 |

OTHER PUBLICATIONS

Dahle et al., "The Weakening Action of Thioctic Acid in Unyeasted and Yeasted Doughs," *Cereal Chem.* 43:682–688 (1966).
Florencio et al., "An NADP/Thioredoxin System in Leaves: Purification and Characterization of NADP–Thioredoxin Reductase and Thioredoxin ih from Spinach," *Arch. Biochem. Biophys.*, 266(2):496–507 (1988).
Crawford et al., "Evidence for Function of the Ferredoxin/Thioredoxin System in the Reductive Activation of Target Enzymes of Isolated Intact Chloroplasts," *Arch. Biochem. Biophys.* 271(1):223–239 (1989).
Yamada, "Inactive Debranching–Enzyme in Rice Seeds, and its Activation," *Carbohydrate Research*, 90:253–157 (1981).
Wada et al., "Purothionin: A Seed Protein with Thioredoxin Activity," *FEBS Letters*, 124(2):237–240 (1981).
Russel et al, "Sequence of Thioredoxin Reductase from *Escherichia coli*," *J. Biol. Chem.*, 263(18):9015–9019 (1988).
Holmgren et al., "Thioredoxin and Glutaredoxin Systems" *J. Biol. Chem.*, 264(24):13963–13966 (1989).
Edman et al., "Sequence of Protein Disulphide Isomerase and Implications of its Relationship to Thioredoxin," *Nature*, 317(19):267–270 (1985).
Johnson et al., "Reduction of Purothionin by the Wheat Seed Thioredoxin System," *Plant Physiol.*, 85:446–451 (1987).
Birk, "Proteinase inhibitors from Plant Sources," *Method Enz.*, 45:695–739 (1976).
Nishiyama et al., "Reactivity of Sulfhydryls in Reduced Gluten with Lipid Hydroperoxides," *Agric. Biol. Chem.*, 51(5):1291–1297 (1987).
Suske, G., et al., "NADPH–Dependent Thioredoxin Reductase and a New Thioredoxin from Wheat,", *Z. Naturforsch. C.* 34:214–221 (1979).
Bodenstein–Lang, J., et al., "Animal and Plant Mitochondria Contain Specific Thioredoxins," *FEBS Lett.* 258:22–26 (1989).
Kasarda, D.D., et al., "Wheat Proteins," *Adv. Cer. Sci. Tech.* 1:158–236 (1976).
Osborne, T.B., et al., "Proteids of the Wheat Kernel," *Amer. Chem. J.* 15:392–471 (1893).
Shewry, P.R., et al., "Seed Storage Proteins of Economically Important Cereals," *Adv. Cer. Sci. Tech.* 7:1–83 (1985).
Birk, Y., "The Bowman–Birk Inhibitor," *Int. J. Peptide Protein Res.* 25:113–131 (1985).

(List continued on next page.)

*Primary Examiner*—Keith Hendricks
(74) *Attorney, Agent, or Firm*—Morrison & Foerster LLP

(57) ABSTRACT

Thioredoxin, a small dithiol protein, is a specific reductant for major food proteins, allergenic proteins and particularly allergenic proteins present in widely used foods from animal and plant sources. All targeted proteins contain disulfide (S—S) bonds that are reduced to the sulfhydryl (SH) level by thioredoxin. The proteins are allergenically active and less digestible in the oxidized (S—S) state. When reduced (SH state), they lose their allergenicity and/or become more digestible. Thioredoxin achieved this reduction when activated (reduced) either by NADPH via NADP-thioredoxin reductase (physiological conditions) or by dithiothreitol, a chemical reductant. Skin tests and feeding experiments carried out with sensitized dogs showed that treatment of the food with reduced thioredoxin prior to ingestion eliminated or decreased the allergenicity of the food. Studies showed increased digestion of food and food proteins by pepsin and trypsin following reduction by thioredoxin.

5 Claims, 14 Drawing Sheets

OTHER PUBLICATIONS

Ryan, C.A., et al., "Proteinase Inhibitors," *The Biochemistry of Plants*, 6:351–370 (1981).

de la Motte–Guery, F. et al., "Mutation of a Negatively Charged Amino Acid in Thioredoxin Modifies its Reactivity with Chloroplastic Enzymes," *Eur. J. Biochem.* 196:287–294 (1991).

Jacquot, J.–P., et al., "Enzyme Regulation in $C_4$ Photosynthesis[1,2]" *Plant Physiol.* 68:300–304 (1981).

Kobrehel, K. et al., "Isolation and Partial Characterisation of Two Low Molecular Weight Durum Wheat (*Triticum durum*) Glutenins," *J. Sci. Food Agric.* 48:441–452 (1989).

Laemmli, "Cleavage of Structural Proteins During the Assembly of the Head of Bacteriophage T4" *Nature* 227:680–685 (1970).

Nishizawa, A.N., et al. (1982), "Chloroplast Fructose–1, 6–Bisphosphatase from Spinach Leaves," *Methods in Chloroplast Molecular Biology*, (M. Edelman, R.B. Hallick and N.–H. Chua, eds.) pp. 707–714, Elsevier Biomedical Press, New York.

Kassel, B., et al., "The Basic Trypsin Inhibitor of Bovine Pancreas," *Biochem. Biophys. Res. Commun.* 20:463–468 (1965).

Jones, B.L., et al., "Amino Acid Sequences of the Two $\alpha$–Purothionins of Hexaploid Wheat," *Cereal Chem.* 54:511–523 (1977).

Wolosiuk, R.A., et al., "Thioredoxin and Glutathione Regulate Photosynthesis in Chloroplasts," *Nature* 266:565–567 (1977).

Tsang, M.L.–S., "Thioredoxin/Glutaredoxin System of Chlorella," *Plant Physiol.* 68:1098–1104 (1981).

Bushuk, W., et al., "Wheat Cultivar Identification by Gliadin Electrophoregrams. I. Apparatus, Method and Nomenclature," *Can. J. Plant Sci.* 58:505–515 (1978).

Sapirstein, H.D., et al., "Computer–Aided Analysis of Gliadin Electrophoregrams. I. Improvement of Precision of Relative Mobility Determiniation by Using a Three Reference Band Standardization," *Cereal Chem.* 62:372–377 (1985).

Tatham, A.S., et al., "Structural Studies of Cereal Prolamins, Including Wheat Gluten," *Adv. Cer. Sci. Tech.* 10:1–78 (1990).

MacRitchie, F., et al., "Flour Polypeptides Related to Wheat Quality," *Adv. Cer. Sci. Tech.* 10:79–145 (1990).

Fickenscher, K., et al., "Purification and Properties of the Cytoplasmic Glucose–6–Phosphate Dehydrogenase from Pea Leaves," *Arch. Biochem. Biophys.* 247:393–402 (1986).

Scheibe, R., et al., "Chloroplast Glucose–6–Phosphate Dehydrogenase: $K_m$ Shift upon Light Modulation and Reduction," *Arch. Biochem. Biophys.* 274:290–297 (1990).

Johnson, T.C., et al., "Thioredoxin and NADP–Thioredoxin Reductase from Cultured Carrot Cells," *Planta* 171:321–331 (1987).

Muller, E.G.D., et al., "Thioredoxin is Essential for Photosynthetic Growth" *J. Biol. Chem.* 264:4008–4014 (1989).

Holmgren (1979), "Reduction of disulfides by thioredoxins," *J. Biol. Chem.* 254:9113–9119.

Holmgren (1985), "Thioredoxin," *Ann. Rev. Biochem.* 54:237–271.

Droux, M. et al. (1987) "Ferredoxin–Thioredoxin Reductase, an Iron–Sulfur Enzyme Linking Light to Enzyme Regulation in Oxygenic Photosynthesis: Purification and Properties of the Enzyme from $C_3$, $C_4$, and Cyanobacterial Species", *Archives of Biochemistry and Biophysics* 252(2):426–439.

Marcus, F. et al. (1988) "Comparative amino acid sequence of fructose–1,6–bisphosphatases: Identification of a region unique to the light–regulated chloroplast enzyme", *Proc. Natl. Acad. Sci. USA* 85:5379–5383.

Raines, C.A. et al. (1988) "Chloroplast fructose–1, 6–bisphosphatase: the product of a mosaic gene", *Nucleic Acids Research* 16:7931–7942.

Decottignies, P. et al. (1988) "Primary Structure of the Light–dependent Regulatory Site of Corn NADP–Malate Dehydrogenase", *The Journal of Biological Chemistry* 263(24):11780–11785.

Miki, J. et al. (1988) "The $\gamma$–subunit of ATP synthase from spinach chloroplasts Primary structure deduced from the cloned cDNA sequence" *FEBS* 232(1):221–226.

Porter, M.A., et al., (1988) "Characterization of the Regulatory Thioredoxin Site of Phosphorinulokinse", *The Journal of Biological Chemistry* 263(1):123–129.

Schiavo, G. et al. (1990) "An Intact Interchain Disulfide Bond Is Required for the Neurotoxicity of Tetanus Toxin", *Infection and Immunity* 58(12):4136–4141.

Muller, R.G.D. "Thioredoxin Deficiency in Yeast Prolongs S Phase and Shortens the G1 Interval of the Cell Cycle," *The Journal of Biological Chemistry* 266(14):9194–9202 (1991).

Blomback et al. "Enzymic reduction of disulfide bonds in fibrinogen by the thioredoxin system. I identification of reduced bonds and studies on reoxidation process" *Thrombosis Research* 4(1):55–75 (1974).

Holmgren et al., "Enzymic reduction of disulfide bonds by thioredoxin. The reactivity of disulfide bonds in human choriogonadotropin and its subunits" *European J. Biochemistry* 70(2):377–383 (1976).

Frick et al., "Immunoglobulin E Antibodies to Pollens Augmented in Dogs by Virus Vaccines," *Am. J. Vet. Res.* 44(3):440–445 (1983).

Wide et al., "Diagnosis of Allergy by an In–Vitro Test for Allergen Antibodies," *The Lancet*, pp. 1105–1107 (Nov. 25, 1976).

Kahlert et al., "Epitope Analysis of the Allergen Ovalbumin With Monoclonal Antibodies and Patients'IgE," *Molecular Immunology* 29(10):1191–1201 (1992).

Matsuda et al., "Reduction of Ovomucoid Immunogenic Activity on Peptic Fragmentation and Heart Denaturation," *Agric. Biol. Chem.* 49(7):2237–2241 (1985).

Rothenbuhler et al., "Disulfide Reduction and Molecular Dissociation Improves the Proteolysis of Soy Glycinin by Pancreatin in vitro," *Journal of Food Science*, 51(6):1479–1482, (1986).

Astwood et al., "Stability of Food Allergens to Digestion in Vitro," *Nature Biotechnology*, 14(10): 1269–1273, (1996).

Buchanan et al., "Thioredoxin–linked Mitigation of Allergic Responses to Wheat," Proceedings of the National Academy of Sciences of the United States of America, 94(10): 5372–5377 (1997).

Buchanan et al., "Thioredoxin: A Mutlifunctional Regulatory Protein with a Bright Future in Technology and Medicine," Archives of Biochemistry and Biophysics, 314(2): 257–260, (1994).

Watt, D.D., et al., "Effects on Lethality of Toxins in Venom from the Scorpion Centruroides Sculpturatus by Group Specific Reagents," *Toxicon* 10:173–181 (1972).

Elsayed, S. et al. (1971) "Characterization of a major allergen (cod). Observations on effect of denaturation on allergenic activity," *J. Allergy* 47:283–291.

Esch et al. (1989), "Identification and localization of allergenic determinants on Grass Group I antigens using monoclonal antibodies," *J. Immunol.* 142:179–184.

Burks, A.W. et al. (1992), "Allergenicity of peanut and soybean extracts altered by chemical and thermal denaturation in patients with atopic dermatitis and positive food challenges," *J. Allergy Clin. Immunol.* 90:889–897.

Morton, J.I. et al. (1961), "Immunochemical Studies of Modified Ovomucoids," *Arch. Biochem. Biophys.* 93:661–665.

Engström, N.E. et al. (1974) "Isolation and Characterization of Calf Liver Thioredoxin", *Journal of Biological Chemistry* 249(1):205–210.

FIG. 1 Mitigation of Skin Test Response by Treating Soy Allergenic Extract with Thioredoxin

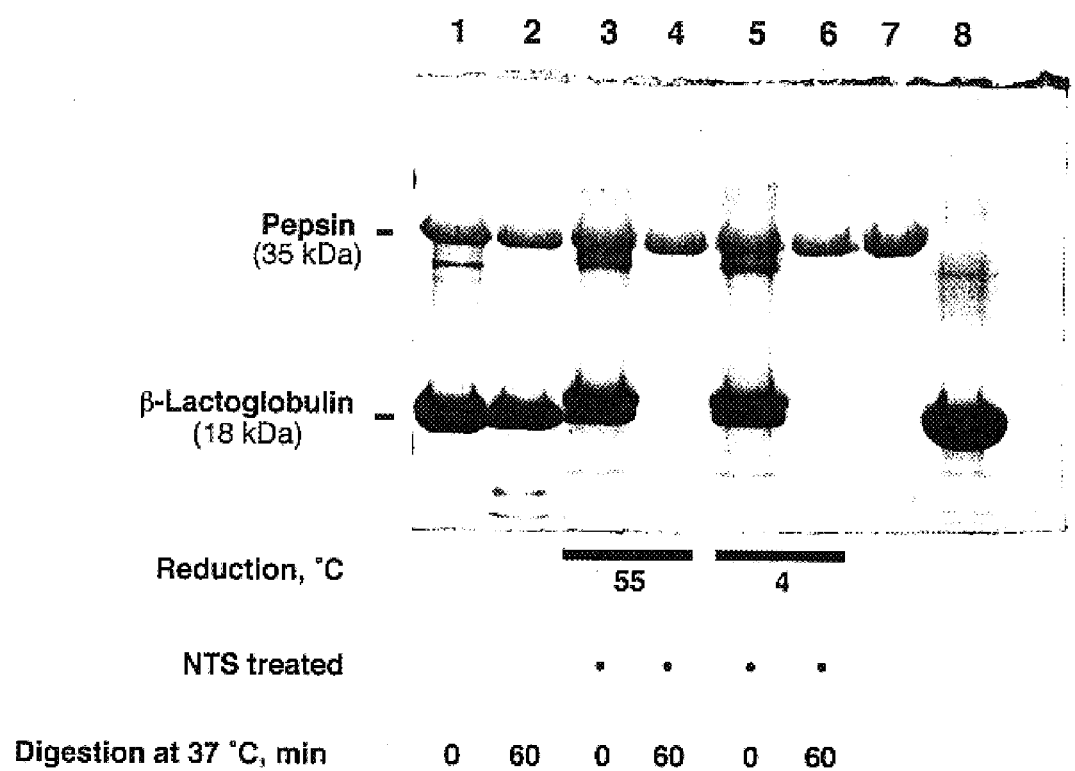
FIG._9

INCREASING THE DIGESTIBILITY OF FOOD PROTEINS BY THIOREDOXIN REDUCTION

CROSS-REFERENCE

This application is a divisional of application Ser. No. 08/953,703 filed Oct. 17, 1997 (now U.S. Pat. No. 5,952,034 issued Sep. 14, 1999), which is a continuation-in-part of application Ser. No. 08/326,976 filed Oct. 21, 1994 (now U.S. Pat. No. 5,792,506 issued Aug. 11, 1998), which is a continuation-in-part of application Ser. No. 08/211,673 filed Nov. 21, 1994 (now U.S. Pat. No. 6,113,951 issued Sep. 5, 2000) which is a national stage filing of International Application No. PCT/US92/08595 filed Oct. 8, 1992, which is a continuation-in-part of application Ser. No. 07/935,002 filed Aug. 25, 1992 (now abandoned), which is a continuation-in-part of application Ser. No. 07/776,109 filed Oct. 12, 1991 (now abandoned).

Reference is also made to the following related applications and patents: (1) application Ser. No. 08/483,930, filed Jun. 7, 1995 (now U.S. Pat. No. 6,114,504 issued Sep. 5, 2000), which is a divisional of application Ser. No. 08/211,673; (2) application Ser. No. 09/046,780 filed Mar. 23, 1998, (now U.S. Pat. No. 6,190,723), which is a divisional of application Ser. No. 08/326,976; (3) application Ser. No. 09/238,379 filed Jan. 27, 1999, (now U.S. Pat. No. 6,555,116), which is a continuation-in-part of application Ser. No. 08/953,703; (4) application Ser. No. 09/447,615 filed Nov. 23, 1999, (now U.S. Pat. No. 6,610,334), which is a divisional of application Ser. No. 08/211,673; (5) application Ser. No. 09/448,109 filed Nov. 23, 1999, (now U.S. Pat. No. 6,583,271), which is a divisional of application Ser. No. 08/211,673; and (6) application Ser. No. 09/448,111 filed Nov. 23, 1999, (now U.S. Pat. No. 6,600,021), which is a divisional of application Ser. No. 08/211,673.

FIELD OF THE INVENTION

The present invention relates to the use of thiol redox proteins to reduce seed protein such as cereal proteins, enzyme inhibitor proteins, venom toxin proteins and the intramolecular disulfide bonds of certain other proteins. More particularly, the invention involves use of thioredoxin and glutaredoxin to reduce gliadins, glutenins, albumins and globulins to improve the characteristics of dough and baked goods and create new doughs and to reduce cystine containing proteins such as amylase and trypsin inhibitors so as to improve the quality of feed and cereal products.

Additonally, the invention involves the isolation of a novel protein that inhibits pullulanase and the reduction of that novel protein by thiol redox proteins. The invention further involves the reduction by thioredoxin of 2S albumin proteins characteristic of oil-storing seeds. Also, the invention involves inactivating snake neurotoxins and certain insect and scorpion venom toxins in vitro and treating the corresponding toxicities in individuals. The invention also involves using thioredoxin to decrease the allergenicity of food allergens and to increase the proteolysis of food proteins and the digestibility of food.

This invention was made with government support under Grant Contract Nos. DCB 8825980 and DMB 88-15980 awarded by the National Science Foundation. The United States Government has certain rights in this invention.

BACKGROUND OF THE INVENTION

Chloroplasts contain a ferredoxin/thioredoxin system comprised of ferredoxin, ferredoxin-thioredoxin reductase and thioredoxins $\underline{f}$ and $\underline{m}$ that links light to the regulation of enzymes of photosynthesis (Buchanan, B. B. (1991) "Regulation of $CO_2$ assimilation in oxygenic photosynthesis: The ferredoxin/thioredoxin system. Perspective on its discovery, present status and future development", *Arch. Biochem. Biophys.* 288:1–9; Scheibe, R. (1991), "Redox-modulation of chloroplast enzymes. A common principle for individual control", *Plant Physiol.* 96:1–3). Several studies have shown that plants also contain a system, analogous to the one established for animals and most microorganisms, in which thioredoxin ($\underline{h}$-type) is reduced by NADPH and the enzyme, NADP-thioredoxin reductase (NTR) according to the following:

$$\text{NADPH} + \text{H}^+ + \text{Thioredoxin } \underline{h}_{ox} \xrightarrow{NTR} \text{NADP} + \text{Thioredoxin } \underline{h}_{red} \quad (1)$$

(Florencio F. J. et al. (1988), *Arch. Biochem. Biophys.* 266:496–507; Johnson, T. C. et al. (1987), *Plant Physiol.* 85:446–451; Suske, G. et al. (1979), *Z. Naturforsch. C.* 34:214–221). Current evidence suggests that the NADP/thioredoxin system is widely distributed in plant tissues and is housed in the mitochondria, endoplasmic reticulum and cytosol (Bodenstein-Lang, J. et al. (1989), *FEBS Lett.* 258:22–26; Marcus, F. et al. (1991), *Arch. Biochem. Biophys.* 287:195–198).

Thioredoxin $\underline{h}$ is also known to reductively activate cytosolic enzyme of carbohydrate metabolism, pyrophosphate fructose-6-P, 1-phosphotransferase or PFP (Kiss, F. et al. (1991), *Arch. Biochem. Biophys.* 287:337–340).

The seed is the only tissue for which the NADP/thioredoxin system has been ascribed physiological activity in plants. Also, thioredoxin $\underline{h}$ has been shown to reduce thionins in the laboratory (Johnson, T. C. et al. (1987), *Plant Physiol.* 85:446–451). Thionins are soluble cereal seed proteins, rich in cystine. In the Johnson, et al. investigation, wheat purothionin was experimentally reduced by NADPH via NADP-thioredoxin reductase (NTR) and thioredoxin $\underline{h}$ according to Eqs. 2 and 3.

$$\text{NADPH} + \text{Thioredoxin } \underline{h}_{ox} \xrightarrow{NTR} \text{NADP} + \text{Thioredoxin } \underline{h}_{red} \quad (2)$$

$$\text{Purthionin}_{ox} + \text{Thioredoxin } \underline{h}_{red} \rightarrow \text{Purthionin}_{red} + \text{Thioredoxin } \underline{h}_{ox} \quad (3)$$

Cereal seeds such as wheat, rye, barley, corn, millet, sorghum and rice contain four major seed protein groups. These four groups are the albumins, globulins, gliadins and the glutenins or corresponding proteins. The thionins belong to the albumin group or faction. Presently, wheat and rye are the only two cereals from which gluten or dough has been formed. Gluten is a tenacious elastic and rubbery protein complex that gives cohesiveness to dough. Gluten is composed mostly of the gliadin and glutenin proteins. It is formed when rye or wheat dough is washed with water. It is the gluten that gives bread dough its elastic type quality. Flour from other major crop cereals barley, corn, sorghum, oat, millet and rice and also from the plant, soybean do not yield a gluten-like network under the conditions used for wheat and rye.

Glutenins and gliadins are cystine containing seed storage proteins and are insoluble. Storage proteins are proteins in the seed which are broken down during germination and used by the germinating seedling to grow and develop. Prolamines are the storage proteins in grains other than wheat that correspond to gliadins while the glutelins are the storage proteins in grains other than wheat that correspond to glutenins. The wheat storage proteins account for up to 80% of the total seed protein (Kasarda, D. D. et al. (1976), *Adv. Cer. Sci. Tech.* 1:158–236; and Osborne, T. B. et al. (1893), *Amer. Chem. J.* 15:392–471). Glutenins and gliadins are considered important in the formation of dough and therefore the quality of bread. It has been shown from in vitro experiments that the solubility of seed storage proteins is increased on reduction (Shewry, P. R. et al. (1985), *Adv. Cer. Sci. Tech.* 7:1–83). However, previously, reduction of glutenins and gliadins was thought to lower dough quality rather than to improve it (Dahle, L. K. et al. (1966), *Cereal Chem.* 43:682–688). This is probably because the non-specific reduction with chemical reducing agents caused the weakening of the dough.

The "Straight Dough" and the "Pre-Ferment" methods are two major conventional methods for the manufacture of dough and subsequent yeast raised bread products.

For the Straight Dough method, all of the flour, water or other liquid, and other dough ingredients which may include, but are not limited to yeast, grains, salt, shortening, sugar, yeast nutrients, dough conditioners, and preservatives are blended to form a dough and are mixed to partial or full development. The resulting dough may be allowed to ferment for a period of time depending upon specific process or desired end-product characteristics.

The next step in the process is the mechanical or manual division of the dough into appropriate size pieces of sufficient weight to ensure achieving the targeted net weight after baking, cooling, and slicing. The dough pieces are often then rounded and allowed to rest (Intermediate Proof) for varying lengths of time. This allows the dough to "relax" prior to sheeting and molding preparations. The time generally ranges from 5–15 minutes, but may vary considerably depending on specific processing requirements and formulations. The dough pieces are then mechanically or manually formed into an appropriate shape are then usually given a final "proof" prior to baking. The dough pieces are then baked at various times, temperatures, and steam conditions in order to achieve the desired end product.

In the Pre-Ferment method, yeast is combined with other ingredients and allowed to ferment for varying lengths of time prior to final mixing of the bread or roll dough. Baker's terms for these systems include "Water Brew", "Liquid Ferment", "Liquid Sponge", and "Sponge/Dough". A percentage of flour ranging from 0–100% is combined with the other ingredients which may include but are not limited to water, yeast, yeast nutrients and dough conditioners and allowed to ferment under controlled or ambient conditions for a period of time. Typical times range from 1–5 hours. The ferment may then be used as is, or chilled and stored in bulk tanks or troughs for later use. The remaining ingredients are added (flour, characterizing ingredients, additional additives, additional water, etc.) and the dough is mixed to partial or full development.

The dough is then allowed to ferment for varying time periods. Typically, as some fermentation has taken place prior to the addition of the remaining ingredients, the time required is minimal (i.e., 10–20 min), however, variations are seen depending upon equipment and product type. Following the second fermentation step, the dough is then treated as in the Straight Dough Method.

As used herein the term "dough mixture" describes a mixture that minimally comprises a flour or meal and a liquid, such as milk or water.

As used herein the term "dough" describes an elastic, pliable protein network mixture that minimally comprises a flour, or meal and a liquid, such as milk or water.

As used herein the term "dough ingredient" may include, but is not exclusive of, any of the following ingredients: flour, water or other liquid, grain, yeast, sponge, salt, shortening, sugar, yeast nutrients, dough conditioners and preservatives.

As used herein, the term "baked good" includes but is not exclusive of all bread types, including yeast-leavened and chemically-leavened and white and variety breads and rolls, english muffins, cakes and cookies, confectionery coatings, crackers, doughnuts and other sweet pastry goods, pie and pizza crusts, pretzels, pita and other flat breads, tortillas, pasta products, and refrigerated and frozen dough products.

While thioredoxin has been used to reduce albumins in flour, thiol redox proteins have not been used to reduce glutenins and gliadins nor other water insoluble storage proteins, nor to improve the quality of dough and baked goods. Thiol redox proteins have also not been used to improve the quality of gluten thereby enhancing its value nor to prepare dough from crop cereals such as barley, corn, sorghum, oat, millet and rice or from soybean flour.

Many cereal seeds also contain proteins that have been shown to act as inhibitors of enzymes from foreign sources. It has been suggested that these enzyme inhibitors may afford protection against certain deleterious organisms (Garcia-Olmedo, F. et al. (1987), *Oxford Surveys of Plant Molecular and Cell Biology* 4:275–335; Birk, Y. (1976), *Meth. Enzymol.* 45:695–739, and Laskowski, M., Jr. et al. (1980), *Ann. Reo. Biochem.* 49:593–626). Two such type enzyme inhibitors are amylase inhibitors and trypsin inhibitors. Furthermore, there is evidence that a barley protein inhibitor (not tested in this study) inhibits an α-amylase from the same source (Weselake, R. J. et al. (1983), *Plant Physiol.* 72:809–812). Unfortunately, the inhibitor protein often causes undesirable effects in certain food products. The trypsin inhibitors in soybeans, notably the Kunitz trypsin inhibitor (KTI) and Bowman-Birk trypsin inhibitor (BBTI) proteins, must first be inactivated before any soybean product can be ingested by humans or domestic animals. It is known that these two inhibitor proteins become ineffective as trypsin inhibitors when reduced chemically by sodium borohydride (Birk, Y. (1985), *Int. J. Peptide Protein Res.* 25:113–131, and Birk, Y. (1976), *Meth. Enzymol.* 45:695–739). These inhibitors like other proteins that inhibit proteases contain intramoelcular disulfides and are usually stable to inactivation by heat and proteolysis (Birk (1976), supra.; Garcia-Olmedo et al. (1987), supra., and Ryan (1980). Currently, to minimize the adverse effects caused by the inhibitors these soybean trypsin inhibitors and other trypsin inhibitors in animal and human food products are being treated by exposing the food to high temperatures. The heat treatment, however, does not fully eliminate inhibitor activity. Further, this process is not only expensive but it also destroys many of the other proteins which have important nutritional value. For example, while 30 min at 120° C. leads to complete inactivation of the BBTI of soy flour, about 20% of the original KTI activity remains (Friedman et al., 1991). The prolonged or higher temperature treatments required for full inactivation of inhibitors results in destruction of amino acids such as cystine, arginine, and lysine (Chae et al., 1984; Skrede and Krogdahl, 1985).

There are also several industrial processes which require α-amylase activity. One example is the malting of barley which requires active α-amylase. Inactivation of inhibitors such as the barley amylase/subtilisin (asi) inhibitor and its equivalent in other cereals by thiol redox protein reduction would enable α-amylases to become fully active sooner than with present procedures, thereby shortening time for malting or similar processes.

Thiol redox proteins have also not previously been used to inactivate trypsin or amylase inhibitor proteins. The reduction of trypsin inhibitors such as the Kunitz and Bowman-Birk inhibitor proteins decreases their inhibitory effects (Birk, Y. (1985), *Int. J. Peptide Protein Res.* 25:113–131). A thiol redox protein linked reduction of the inhibitors in soybean products designed for consumption by humans and domestic animals would require no heat or lower heat than is presently required for protein denaturization, thereby cutting the costs of denaturation and improving the quality of the soy protein. Also a physiological reductant, a so-called clean additive (i.e., an additive free from ingredients viewed as "harmful chemicals") is highly desirable since the food industry is searching for alternatives to chemical additives. Further the ability to selectively reduce the major wheat and seed storage proteins which are important for flour quality (e.g., the gliadins and the glutenins) in a controlled manner by a physiological reductant such as a thiol redox protein would be useful in the baking industry for improving the characteristics of the doughs from wheat and rye and for creating doughs from other grain flours such as cereal flours or from cassava or soybean flour.

The family of 2S albumin proteins characteristic of oilstoring seeds such as castor bean and Brazil nut (Kreis et al. 1989; Youle and Huang, 1981) which are housed within protein bodines in the seed endosperm or cotyledons (Ashton et al. 1976; Weber et al. 1980), typically consist of dissimilar subunits connected by two intermolecular disculfide bonds—one subunit of 7 to 9 kDa and the other of 3 to 4 kDa. The large subunit contians two intramolecular disculfide groups, the small subunit contains none. The intramolecular disculfides of the 2S large subunit show homology with those of the soybean Bowman-Birk inhibitor (Kreis et al. 1989) but nothing is known of the ability of 2S proteins to undergo reduction under physiological conditions.

These 2S albumin proteins are rich in methionine. Recently transgenic soybeans which produce Brazil nut 2S protein have been generated. Reduction of the 2S protein in such soybeans could enhance the integration of the soy proteins into a dough network resulting in a soybread rich in methionine. In addition, these 2S proteins are often allergens. Reduction of the 2S protein would result in the cessation of its allergic activity.

Pullulanase ("debranching enzyme") is an enzyme that breaks down the starch of the endosperm of cereal seeds by hydrolytically cleaving α-1,6 bonds. Pullulanase is an enzyme fundamental to the brewing and baking industries. Pullulanase is required to break down starch in malting and in certain baking procedures carried out in the absence of added sugars or other carbohydrates. Obtaining adequate pullulanase activity is a problem especially in the malting industry. It has been known for some time that dithiothreitol (DTT, a chemical reductant for thioredoxin) activates pullulanase of cereal preparations (e.g., barley, oat and rice flours). A method for adequately activating or increasing the activity of pullulanase with a physiologically acceptable system, could lead to more rapid malting methods and, owing to increased sugar availability, to alcoholic beverages such as beers with enhanced alcoholic content.

Death and permanent injury resulting from snake bites are serious problems in many African, Asian and South American countries and also a major concern in several southern and western areas of the United States. Venoms from snakes are characterized by active protein components (generally several) that contain disulfide (S—S) bridges located in intramolecular (intrachain) cystines and in some cases in intermolecular (interchain) cystines. The position of the cystine within a given toxin group is highly conserved. The importance of intramolecular S—S groups to toxicity is evident from reports showing that reduction of these groups leads to a loss of toxicity in mice (Yang, C. C. (1967) *Biochim. Biophys. Acta.* 133:346–355; Howard, B. D. et al. (1977) *Biochemistry* 16:122–125). The neurotoxins of snake venom are proteins that alter the release of neurotransmitter from motor nerve terminals and can be presynaptic or postsynaptic. Common symptoms observed in individuals suffering from snake venom neurotoxicity include swelling, edema and pain, fainting or dizziness, tingling or numbing of affected part, convulsions, muscle contractions, renal failure, in addition to long-term necrosis and general weakening of the individual, etc.

The presynaptic neurotoxins are classified into two groups. The first group, the β-neurotoxins, include three different classes of proteins, each having a phospholipase $A_2$ component that shows a high degree of conservation. The proteins responsible for the phospholipase $A_2$ activity have from 6 to 7 disulfide bridges. Members of the β-neurotoxin group are either single chain (e.g., caudotoxin, notexin and agkistrodotoxin) or multichain (e.g., crotoxin, ceruleotoxin and *Vipera* toxin). β-bungarotoxin, which is made up of two subunits, constitutes a third group. One of these subunits is homologous to the Kunitz-type proteinase inhibitor from mammalian pancreas. The multichain β-neurotoxins have their protein components linked ionically whereas the two subunits of β-bungarotoxin are linked covalently by an intermolecular disulfide. The B chain subunit of β-bungarotoxin, which is also homologous to the Kunitz-type proteinase inhibitor from mammalian pancreas, has 3 disulfide bonds.

The second presynaptic toxin group, the facilitatory neurotoxins, is devoid of enzymatic activity and has two subgroups. The first subgroup, the dendrotoxins, has a single polypeptide sequence of 57 to 60 amino acids that is homologous with Kunitz-type trypsin inhibitors from mammalian pancreas and blocks voltage sensitive potassium channels. The second subgroup, such as the fasciculins (e.g., fasciculin 1 and fasiculin 2) are cholinesterase inhibitors and have not been otherwise extensively studied.

The postsynaptic neurotoxins are classified either as long or short neurotoxins. Each type contains S—S groups, but the peptide is unique and does not resemble either phospholipase $A_2$ or the Kunitz or Kunitz-type inhibitor protein. The short neurotoxins (e.g., erabutoxin a and erabutoxin b) are 60 to 62 amino acid residues long with 4 intramolecular disulfide bonds. The long neurotoxins (e.g., α-bungarotoxin and α-cobratoxin) contain from 65 to 74 residues and 5 intramolecular disulfide bonds. Another type of toxins, the cytotoxins, acts postsynaptically but its mode of toxicity is ill defined. These cytotoxins show obscure pharmacological effects, e.g., hemolysis, cytolysis and muscle depolarization. They are less toxic than the neurotoxins. The cytotoxins usually contain 60 amino acids and have 4 intramolecular disulfide bonds. The snake venom neurotoxins all have multiple intramolecular disulfide bonds.

The current snake antitoxins used to treat poisonous snake bites following first aid treatment in individuals primarily involve intravenous injection of antivenom prepared in horses. Although it is not known how long after envenomation the antivenom can be administered and be effective, its use is recommended up to 24 hours. Antivenom treatment is generally accompanied by administration of intravenous fluids such as plasma, albumin, platelets or specific clotting factors. In addition, supporting medicines are often given, for example, antibiotics, antihistamines, antitetanus agents, analgesics and sedatives. In some cases, general treatment measures are taken to minimize shock, renal failure and respitory failure. Other than administering calcium-EDTA in the vicinity of the bite and excising the wound area, there are no known means of localized treatment that result in toxin neutralization and prevention of toxic uptake into the blood stream. Even these localized treatments are of questionable significance and are usually reserved for individuals sensitive to horse serum (Russell, F. E. (1983) *Snake Venom Poisoning,* Schollum International, Inc. Great Neck, N.Y.).

The term "individual" as defined herein refers to an animal or a human.

Most of the antivenoms in current use are problematic in that they can produce harmful side effects in addition to allergic reactions in patients sensitive to horse serum (up to 5% of the patients). Nonallergic reactions include pyrogenic shock, and complement depletion (Chippaur, J.-P. et al. (1991) *Reptile Venoms and Toxins,* A. T. Tu, ed., Marcel Dekker, Inc., pp. 529–555).

It has been shown that thioredoxin, in the presence of NADPH and thioredoxin reductase reduces the bacterial neurotoxins tetanus and botulinum A in vitro (Schiavo, G. et al. (1990) *Infection and Imununity* 58:41364141; Kistner, A. et al. (1992) *Naunyn-Schmiedeberg's Arch Pharmacol* 345:227–234). Thioredoxin was effective in reducing the interchain disulfide link of tetanus toxin and such reduced tetanus toxin was no longer neurotoxic (Schiavo et al., supra.). However, reduction of the interchain disulfide of botulinum A toxin by thioredoxin was reported to be much more sluggish (Kistner et al., supra.). In contrast to the snake neurotoxin studied in the course of this invention, the tetanus research group (Schiavo et al., supra.) found no evidence in the work done with the tetanus toxin that reduced thioredoxin reduced toxin intrachain disulfide bonds. There was also no evidence that thioredoxin reduced intrachain disulfides in the work done with botulinum A. The tetanus and botulinum A toxins are significantly different proteins from the snake neurotoxins in that the latter (1) have a low molecular weight; (2) are rich in intramolecular disulfide bonds; (3) are resistant to trypsin and other animal proteases; (4) are active without enzymatic modification, e.g., proteolytic cleavage; (5) in many cases show homology to animal proteins, such as phospholipase $A_2$ and Kunitz-type proteases; (6) in most cases lack intermolecular disulfide bonds, and (7) are stable to agents such as heat and proteases.

Reductive inactivation of snake toxins in vitro by incubation with 1% β-mercaptoethanol for 6 hours and incubation with 8M urea plus 300 mM β-mercaptoethanol has been reported in the literature (Howard, B. D. et al. (1977) *Biochemistry* 16:122–125; Yang, C. C. (1967) *Biochim. Biophys. Acta.* 133:346–355). These conditions, however, are far from physiological. As defined herein the term "inactivation" with respect to a toxin protein means that the toxin is no longer biologically active in vitro, in that the toxin is unable to link to a receptor. Also as used herein, "detoxification" is an extension of the term "inactivation" and means that the toxin has been neutralized in an individual as determined by animal toxicity tests.

Bee venom is a complex mixture with at least 40 individual components, that include major components as melittin and phospholipase $A_2$, representing respectively 50% and 12% of the total weight of the venom, and minor components such as small proteins and peptides, enzymes, amines, and amino acids.

Melittin is a polypeptide consisting of 26 amino acids with a molecular weight of 2840. It does not contain a disulfide bridge. Owing to its high affinity for the lipid-water interphase, the protein permeates the phospholipid bilayer of the cell membranes, disturbing its organized structure. Melittin is not by itself a toxin but it alters the structure of membranes and thereby increases the hydrolitic activity of phospholipase $A_2$, the other major component and the major allergen present in the venom.

Bee venom phospholipase $A_2$ is a single polypeptide chain of 128 amino acids, is cross-linked by four disulfide bridges, and contains carbohydrate. The main toxic effect of the bee venom is due to the strong hydrolytic activity of phospholipase $A_2$ achieved in association with melittin.

The other toxic proteins in bee venom have a low molecular weight and contain at least two disulfide bridges that seem to play an important structural role. Included are a protease inhibitor (63–65 amino acids), MCD or 401-peptide (22 amino acids) and apamin (18 amino acids).

Although there are thousands of species of bees, only the honey bee, *Apis mellifera,* is a significant cause of allergic reactions. The response ranges from local discomfort to systemic reactions such as shock, hypotension, dyspnea, loss of consciousness, wheezing and/or chest tightness that can result in death. The only treatment that is used in these cases is the injection of epinephrine.

The treatment of bee stings is important not only for individuals with allergic reactions. The "killer" or Africanized bee, a variety of honey bee is much more agressive than European honey bees and represents a danger in both South and North America. While the lethality of the venom from the Africanized and European bees appears to be the same (Schumacher, M. I. et al. (1989) *Nature* 337:413), the behaviour pattern of the hive is completely different. It was reported that Africanized bees respond to colony disturbance more quickly, in greater numbers and with more stinging (Collins, A. M. et al. (1982) *Science* 218:72–74). A mass attack by Africanized bees may produce thousands of stings on one individual and cause death. The "killer" bees appeared as a result of the interbreeding between the African bee (*Apis mellifera scutellata*) and the European bee (*Apis mellifera mellifera*). African bees were introduced in 1956 into Brazil with the aim of improving honey production being a more tropically adapted bee. Africanized bees have moved from South America to North America, and they have been reported in Texas and Florida.

In some areas of the world such as Mexico, Brazil, North Africa and the Middle East, scorpions present a life hazard to humans. However, only the scorpions of family Buthidae (genera, *Androctonus, Buthus, Centruroides, Leiurus* and *Tityus*) are toxic for humans. The chemical composition of the scorpion venom is not as complex as snake or bee venom. Scorpion venom contains mucopolysaccharides, small amounts of hyaluronidase and phospholipase, low molecular-weight molecules, protease inhibitors, histamine releasers and neurotoxins, such as serotonin. The neurotoxins affect voltage-sensitive ionic channels in the neuromuscular junction. The neurotoxins are basic polypeptides with three to four disulflde bridges and can be classified in two groups: peptides with from 61 to 70 amino acids, that block sodium channel, and peptides with from 36 to 39 amino acids, that block potassium channel. The reduction of disulfide bridges on the neurotoxins by nonphysiological reductants such as DTT or β-mercaptoethanol (Watt, D. D. et al. (1972) *Toxicon* 10:173–181) lead to loss of their toxicity.

Symptoms of animals stung by poisonous scorpions inclure hyperexcitability, dyspnea, convulsions, paralysis and death. At present, antivenin is the only antidote for scorpion stings. The availability of the venom is a major problem in the production of antivenin. Unlike snake venom, scorpion venom is very difficult to collect, because the yield of venom per specimen is limited and in some cases the storage of dried venom leads to modification of its toxicity. An additional problem in the production of antivenins is that the neurotoxins are very poor antigens.

The reductive inactivation of snake, bee and scorpion toxins under physiological conditions has never been reported nor has it been suggested that the thiol redox agents, such as reduced lipoic acid, DTT, or reduced thioredoxin could act as an antidote to these venoms in an individual.

Food allergies also represent a long-standing problem important both nationally and internationally. Up to 5% of children under age 12 and 1% of adults are clinically affected in the U.S. population (Adverse Reactions to Foods—AAAI and NIAD Report, 1984, NIH Pub. No. 84–2442, pp. 2, 3). In some countries, the figures are higher, and, throughout the world, the problem is considered to be increasing, especially in infants (T. Matsuda and R. Nakamura 1993 Molecular structure and immunological properties of Food Allergens, Trends in Food Science & Technology 4, 289–293). The problem extends to a wide range of foods. Food allergies in general have recently achieved an increased profile as a result of the concern about transgenic foods.

Milk represents a significant problem, especially in infants. Wheat and soy allergies are of growing importance as new populations adopt these foods and are of increased concern in pet (especially dog) foods. Beef, rice and egg also cause serious allergies in many individuals and again are of significant concern with respect to pet food.

Many of the major allergenic proteins in the above mentioned foods have intramolecular disulfide (S—S) bonds but so far two treatments have been applied commercially to minimize food allergies: (1) heat, and (2) enzymatic proteolysis. In both cases, success has been only partial. While lowering allergenicity, heat treatment has not eliminated the problem, even in the best of cases, because the responsible proteins are typically heat stable. Moreover, heat lowers product quality by destroying nutritionally important amino acids such as lysine, cysteine and arginine. Enzymatic proteolysis is more successful in reducing allergenicity, but desirable food properties such as flavor are usually lost and treatment is costly. Therefore a physiologically safe system that would bring about a decrease in or loss of allergenicity when applied to allergenic foods without a resulting loss in flavor and nutrition would be extremely valuable.

SUMMARY OF THE INVENTION

It is an object herein to provide a method for reducing a non thionin cystine containing protein.

It is a second object herein to provide methods utilizing a thiol redox protein alone or in combination with a reductant or reduction system to reduce glutenins or gliadins present in flour or seeds.

It is also an object herein to provide methods using a thiol redox protein alone or in combination with a reductant or reduction system to improve dough strength and baked goods characteristics such as better crumb quality, softness of the baked good and higher loaf volume.

It is a further object herein to provide formulations containing a thiol redox protein useful in practicing such methods.

Still a further object herein is to provide a method for producing a dough from rice, corn, soybean, barley, oat, cassava, sorghum or millet flour.

Yet, another object is to provide a method for producing an improved gluten or for producing a gluten-like product from cereal grains other than wheat and rye.

It is further an object herein to provide a method of reducing an enzyme inhibitor protein having disulfide bonds.

Still another object herein is to provide yeast cells genetically engineered to express or overexpress thioredoxin.

Still yet another object herein is to provide yeast cells genetically engineered to express or overexpress NADP-thioredoxin reductase.

Still yet a further object herein is to provide a method for improving the quality of dough or a baked good using such genetically engineered yeast cells.

Yet still another object herein is to provide a method of reducing the intramolecular disulfide bonds of a non-thionin, non chloroplast protein containing more than one intramolecular cystine comprising adding a thiol redox protein to a liquid or substance containing the cystines containing protein, reducing the thiol redox protein and reducing the cystines containing protein by means of the thiol redox protein.

Another object herein is to provide an isolated pullulanase inhibitor protein having disulfide bonds and a molecular weight of between 8 to 15 kDa.

Still another object herein is to provide a method of increasing the activity of pullulanase derived from barley or wheat endosperm comprising adding thioredoxin to a liquid or substance containing the pullulanase and reducing the thioredoxin thereby increasing the pullulanase activity.

Still another object herein is to provide a method of reducing an animal venom toxic protein having one or more intramolecular cystines comprising contacting the cystine containing protein with an amount of a thiol redox (SH) agent effective for reducing the protein, and maintaining the contact for a time sufficient to reduce one or more disulfide bridges of the one or more intramolecular cystines thereby reducing the neurotoxin protein. The thiol redox (SH) agent may be a reduced thioredoxin, reduced lipoic acid in the presence of a thioredoxin, DTT or DTT in the presence of a thioredoxin and the snake neurotoxin protein may be a presynaptic or postsynaptic neurotoxin.

Still a further object of the invention is to provide a composition comprising a snake neurotoxin protein and a thiol redox (SH) agent.

Still yet another object of the invention is to provide a method of reducing an animal venom toxic protein having one or more intramolecular cystines comprising contacting the protein with amounts of NADP-thioredoxin reductase, NADPH or an NADPH generator system and a thioredoxin effective for reducing the protein, and maintaining the contact for a time sufficient to reduce one or more disulfide bridges of the one or more intramolecular cystines thereby reducing the protein.

Yet another object herein is to provide a method of inactivating, in vitro, a snake neurotoxin having one or more intramolecular cystines comprising adding a thiol redox (SH) agent to a liquid containing the toxin wherein the amount of the agent is effective for reducing the toxin.

Yet a further object herein is to provide a method of treating venom toxicity in an individual comprising administering, to an individual suffering from venom toxicity, amounts of a thiol redox (SH) agent effective for reducing or alleviating the venom toxicity.

In accordance with the objects of the invention, methods are provided for improving dough characteristics comprising the steps of mixing a thiol redox protein with dough ingredients to form a dough and baking said dough.

Also, in accordance with the objects of the invention, a method is provided for inactivating an enzyme inhibitor protein in a grain food product comprising the steps of mixing a thiol redox protein with the seed product, reducing the thiol redox protein by a reductant or reduction system and reducing the enzyme inhibitor by the reduced thiol redox protein, the reduction of the enzyme inhibitor inactivating the enzyme inhibitor.

The thiol redox proteins in use herein can include thioredoxin and glutaredoxin. The thioredoxin includes but is not exclusive of *E. coli* thioredoxin, thioredoxin h, f and m and animal thioredoxins. A reductant of thioredoxin used herein can include lipoic acid or a reduction system such as NADPH in combination with NADP thioredoxin reductase (NTR). The reductant of glutaredoxin can include reduced glutathione in conjunction with the reduction system NADPH and glutathione reductase. NADPH can be replaced with an NADPH generator or generator composition such as one consisting of glucose 6-phosphate, NADP and glucose 6-phosphate dehydrogenase from a source such as yeast. The NADPH generator is added together with thioredoxin and NADP-thioredoxin reductase at the start of the dough making process.

It should be noted that the invention can also be practiced with cysteine containing proteins. The cysteines can first be oxidized and then reduced via thiol redox protein.

Further in accordance with the objects of the invention, a method is provided for decreasing the allergenicity of an allergenic food protein comprising the steps of contacting the protein with an amount of thioredoxin, NTR and NADPH or an amount of DTT in the presence of thioredoxin effective for decreasing the allergenicity of the protein and administering the contacted protein in step (a) to an animal, thereby decreasing the allergenic symptoms in said animal that would otherwise occur if the animal received the untreated protein.

Another object of the invention is to provide a hypoallergenic ingestible food. The food was made hypoallergenic by prior treatment with thioredoxin in the presence of NTR and NADPH. The food can be beef, milk, soy, egg, rice or wheat.

A further object of the invention is to provide a method for improving the proteolysis and therefore the digestibility of food proteins and consequently to also provide more digestible foods. The foods are made more susceptible to proteolysis and more digestible by prior treatment with thioredoxin in the presence of reductants of thioredoxin such as those described above. Appropriate foods include soy, nuts, milk, whey, beef, egg, bread, other wheat products, and other grain products.

BRIEF DESCRIPTION OF THE DRAWINGS

FIG. 1 is a bar graph showing the mitigation of a skin test response to soy allergen by treating soy allergenic extract with reduced thioredoxin.

FIG. 9 is a photograph of a protein stained SDS polyacrylamide electrophoretic gel showing the effect of thioredoxin-linked reduction on pepsin digestion of bovine β-lactoglobulin.

DETAILED DESCRIPTION OF THE INVENTION

Figure 2:
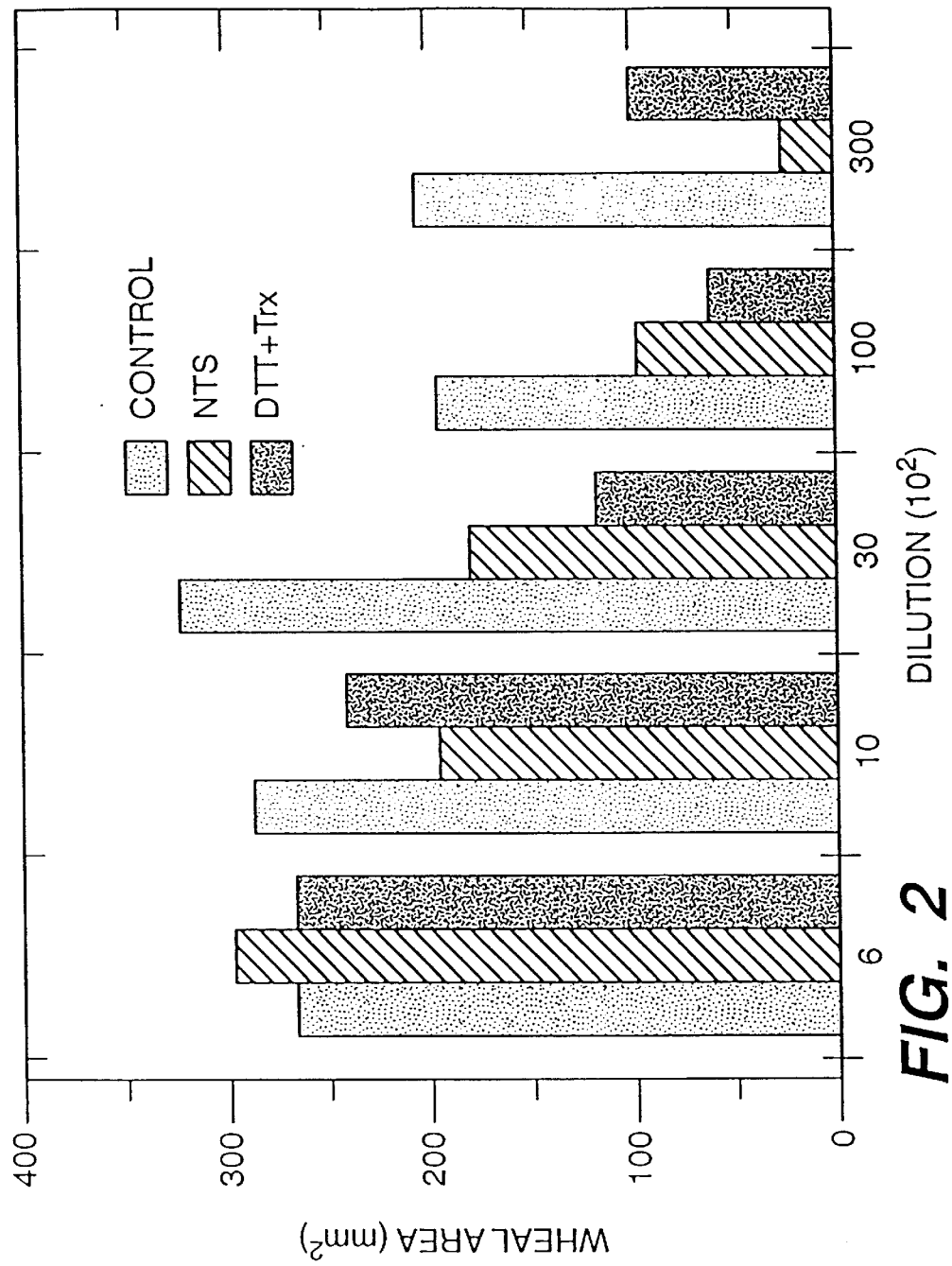
FIG. 2 is a bar graph showing the mitigation of a skin test response to milk allergen by treating milk allergenic extract with reduced thioredoxin.
Figure 3:
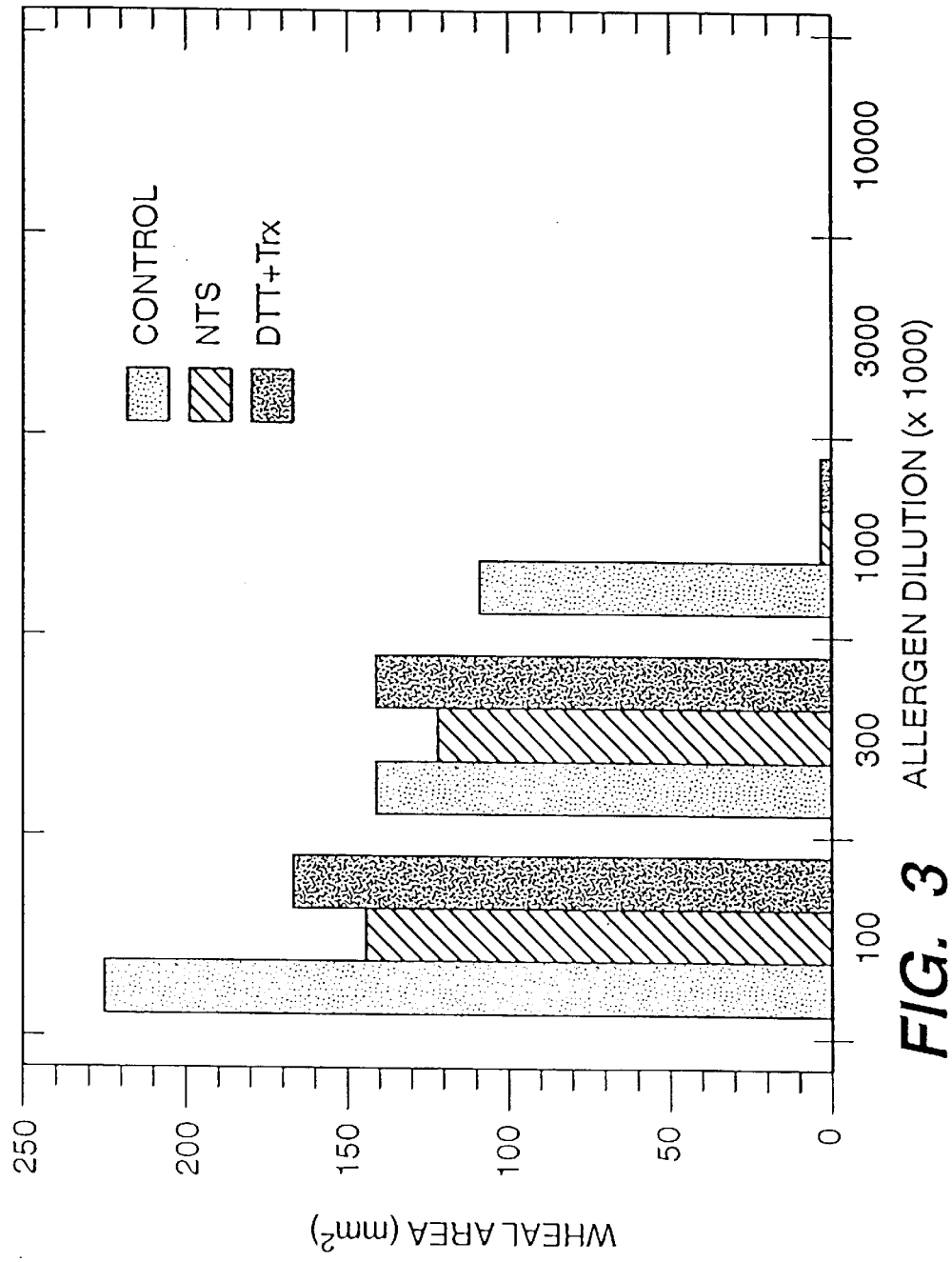
FIG. 3 is a bar graph showing the mitigation of a skin test response to wheat allergen by treating wheat allergenic extract with reduced thioredoxin.
Figure 4:
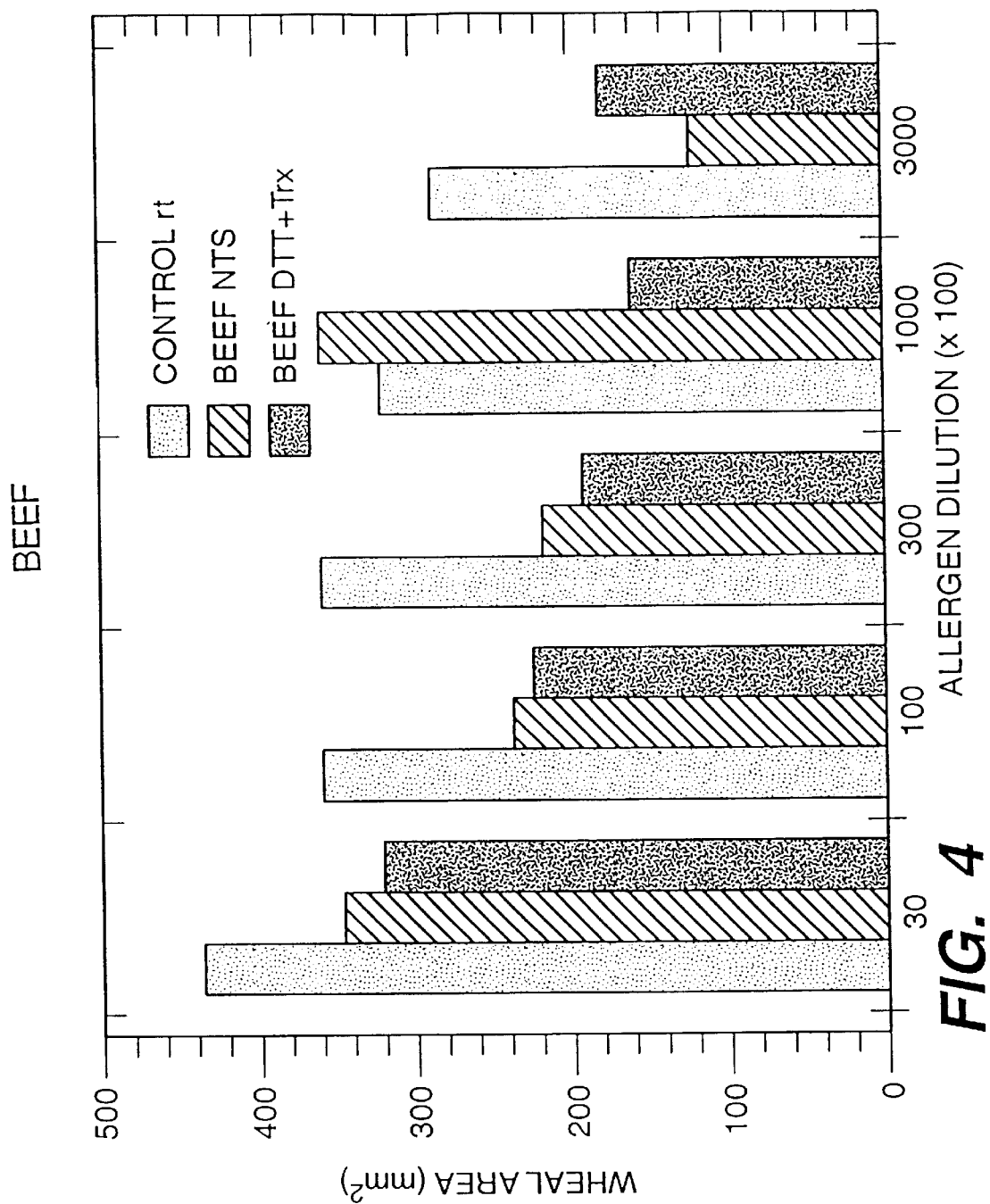
FIG. 4 is a bar graph showing the mitigation of a skin test response to beef allergen by treating beef allergenic extract with reduced thioredoxin at room temperature.
Figure 5:
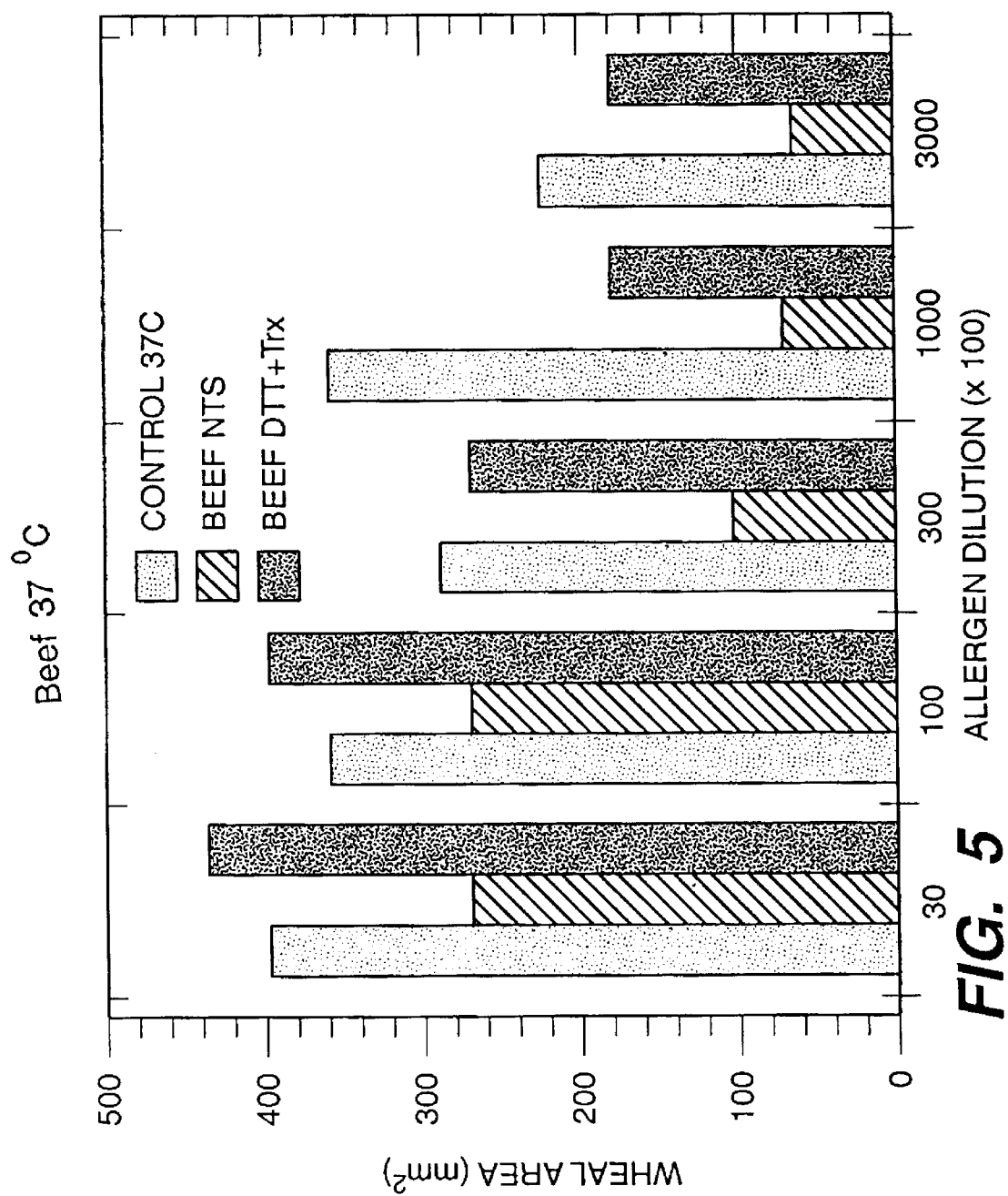
FIG. 5 is a bar graph showing the mitigation of a skin test response to beef allergen by treating beef allergenic extract with reduced thioredoxin at 37° C.

In accordance with this detailed description, the following definitions and abbreviations apply:

CM—certain bread wheat α-amylase inhibitors
DSG—certain α-amylase inhibitors isolated from durum wheat
DTNB—2'5'-dithiobis (2-nitrobenzoic acid)
NTR—NADP-thioredoxin reductase
mBBr—monobromobimane
NADP-MDH—NADP-malate dehydrogenase
FBPase—fructose-1,6-bisphosphatase
SDS—sodium dodecyl sulfate
DTT—dithiothreitol
Cereal—millet, wheat, oat, barley, rice, sorghum, or rye BBTI—Bowman-Birk soybean trypsin inhibitor
KTI—Kunitz soybean trypsin inhibitor
PAGE—polyacrylamide gel electrophoresis
TCA—trichloroacetic acid Enzyme Inhibitor Protein Experiments Starting Materials Materials Seeds of bread wheat *Triticum aestivum* L, cv. Talent) and durum wheat (*Triticum durum.* Desf., cv. Mondur) were obtained from laboratory stocks.

Reagents

Chemicals and fine chemicals for enzyme assays and sodium dodecyl sulfate (SDS)-polyacrylamide gel electrophoresis were purchased from Sigma Chemical Co. and BioRad Laboratories, respectively. Monobromobimane (mBBr, tradename Thiolite) was purchased from Calbiochem. Other chemicals were obtained from commercial sources and were of the highest quality available.

Enzymes

Thioredoxin and NTR from *E. coli* ware purchased from American Diagnostics, Inc. and were also isolated from cells transformed to overexpress each protein. The thioredoxin strain containing the recombinant p]asmid, pFP1, was kindly provided by Dr. J.-P. Jacquot (de la Motte-Guery, F. et al. (1991) *Eur. J. Biochem.* 196:287–294). The NTR strain containing the recombinant plasmid, pPMR21, was kindly provided by Drs. Marjorie Russel and Peter Model (Russel, M. et al. (1988) *J. Biol. Chem.* 263:9015–9019). The Isolation procedure used for these proteins was as described in those studies with the following changes: cells were broken in a Ribi cell fractionator at 25,000 psi and NTR was purified as described by Florencio et al. (Fiorencio, F. J. et al. (1988) *Arch. Biochem. Biophys.* 266:496–507) without the red agarose step. Thioredoxin and NTR from *Saccharomyces cerevisiae* (baker's yeast type 1) were isolated by the procedure developed by Florencio et al. for spinach leaves with the following changes: suspended cells [1 part cells:5 parts buffer (w/v)], were broken in a Ribi cell fractionator at 40,000 psi with three passes.

Thioredoxin h and NTR were isolated from wheat germ by the procedure developed for spinach leaves (Florencio, F. J. et al. (1988), *Arch. Biochem. Biophys.* 266:496–507). NADP-malate dehydrogenase (NADP-MDH) and fructose-1,6-bisphosphatase (FBPase) were purified from leaves of corn (Jacquot, J.-P. et al. (1981), *Plant Physiol.* 68:300–304) and spinach (Crawford, N. A. et al. (1989), *Arch. Biochem. Biophys.* 271:223–239) respectively. *E. coli* glutaredoxin and calf thymus thioredoxin were obtained from Professor A. Holmgren.

α-Amylase and Trypsin Inhibitors

CM-1 protein was isolated from the albumin-globulin fraction of bread wheat flour as described previously (Kobrehel, K. et al. (1991), *Cereal Chem.* 68:1–6). A published procedure was also used for the isolation of DSG proteins (DSG-1 and DSG-2) from the glutenin fraction of durum wheat (Kobrehel, K. et al. (1989), *J. Sci. Food Agric.* 48:441–452). The CM-1, DSG-1 and DSG-2 proteins were homogeneous in SDS-polyacrylamide gel electrophoresis. Trypsin inhibitors were purchased from Sigma Chemical Co., except for the one from corn kernel which was from Fluca. In all cases, the commercial preparations showed a single protein component which migrated as expected in SDS-PAGE (Coomassie Blue stain), but in certain preparations, the band was not sharp.

Other Proteins

Purothionin α from bread wheat and purothionins α-1 and β from durun wheat were kind gifts from Drs. D. D. Kasarda and B. L. Jones, respectively. The purothionin a sample contained two members of the purothionin family when examined with SDS-polyacrylamide gel electrophoresis. The purothionin α-1 and β samples were both homogeneous in SDS-polyacrylamide gel electrophoresis.

Routine Method Steps

Enzyme Activation Assays

The NADP-MDH, FBPase, NTR and Thioredoxin h assay methods were according to Florencio, F. J. et al. (1988), *Arch. Biochem. Biophys.* 266:496–507 with slight modifications as indicated. For enzyme activation assays, the preincubation time was 20 min unless specified otherwise.

mBBr Fluorescent Labeling and SDS-polyacrylamide Gel Electrophoresis Analyses

Direct reduction of the proteins under study was determined by a modification of the method of Crawford et al. (Crawford, N. A. et al. (1989), *Arch. Biochem. Biophys.* 271:223–239). The reaction was carried out in 100 mM potassium phosphate buffer, pH 7.1, containing 10 mM EDTA and 16% glycerol in a final volume of 0.1 ml. As indicated, 0.7 μg (0.1 μM) NTR and 1 μg (0.8 μM) thioredoxin (both routinely from *E. coli* were added to 70 μl of the buffer solution containing 1 mM NADPH and 10 μg (2 to 17 μM) of target protein. When thioredoxin was reduced by dithiothreitol (DTT, 0.5 mM), NADPH and NTR were omitted. Assays with reduced glutathione were performed similarly, but at a final concentration of 1 mM. After incubation for 20 min, 100 nmoles of mBBr were added and the reaction was continued for another 15 min. To stop the reaction and derivatize excess mBBr, 10 μl of 10% SDS and 10 μl of 100 mM β-mercaptoethanol were added and the samples were then applied to the gels. In the case of reduction by glutaredoxin, the thioredoxin and NTR were replaced by 1 μg (0.8 μM) *E. coli* glutaredoxin, 1.4 μg (0.14 μM) glutathione reductase purified from spinach leaves (Florencio, F. J. et al. (1988), *Arch. Biochem. Biophys.* 266:496–507) and 1.5 mM NADPH was used. Gels (17.5% w/v, 1.5 mm thickness) were prepared according to Laemmli (Laemmli, U. K. (1970), *Nature* 227:680–685) and developed for 16 hr. at constant current (9 mA). Following electrophoresis, gels were placed in a solution of 40% methanol and 10% acetic acid, and soaked for 4 to 6 hours with several changes of the solution. Gels were then examined for fluorescent bands with near ultraviolet light and photographed (exposure time 25 sec) according to Crawford et al. (Crawford, N. A. et al. (1989), *Arch. Biochem. Biophys.* 271:223–239). Finally, gels were stained with Coomassie Blue and destained as before (Crawford, N. A. et al. (1989), *Arch. Biochem. Biophys.* 271:223–239).

Quantification of Labeled Proteins

To obtain a quantitative indication of the extent of reduction of test proteins by the NADP/thioredoxin system, the intensities of their fluorescent bands seen in SDS-polyacrylamide gel electrophoresis were evaluated, using a modification of the procedure of Crawford et al. (Crawford, N. A. et al. (1989), *Arch. Biochem. Biophys.* 271:223–239). The photographic negatives were scanned using a Pharmacia Ultrascan laser densitometer, and the area underneath the peaks was quantitated by comparison to a standard curve determined for each protein. For the latter determination, each protein (at concentrations ranging from 1 to 5 μg) was reduced by heating for 3 min at 100° C. in the presence of 0.5 mM DTT. Labeling with mBBr was then carried out as described above except that the standards were heated for 2 min at 100° C. after the reaction was stopped with SDS and excess mBBr derivatized with β-mercaptoethanol. Because the intensity of the fluorescent bands was proportional to the amounts of added protein, it was assumed that reduction was complete under the conditions used.

EXAMPLE 1

Thioredoxin-linked Reduction of α-Amylase Inhibitors

Enzyme Activation Assays

The capability to replace a specific thioredoxin in the activation of chloroplast enzymes is one test for the ability of thiol groups of a given protein to undergo reversible redox change. Even though not physiological in the case of extra-plastidic proteins, this test has proved useful in several studies. A case in point is purothionin which, when reduced by thioredoxin $\underline{h}$ activates chloroplast FBPase (Wada, K. et al. (1981), *FEBS Lett.* 124:237–240, and Johnson, T. C. et al. (1987), *Plant Physiol.* 85:446–451). The FBPase, whose physiological activator is thioredoxin $\underline{f}$, is unaffected by thioredoxin $\underline{h}$. In this Example, the ability of cystine-rich proteins to activate FBPase as well as NADP-MDH was tested as set forth above. The α-amylase inhibitors from durum wheat (DSG-1 and DSG-2) were found to be effective in enzyme activation; however, they differed from purothionin in showing a specificity for NADP-MDH rather than FBPase (Table I). The α-amylase inhibitors were active only in the presence of reduced thioredoxin $\underline{h}$, which itself did not significantly activate NADP-MDH under these conditions. DSG-1 and DSG-2 activated NADP-malate dehydrogenase in the presence of DTT-reduced thioredoxin $\underline{h}$ according to the reaction sequence (DTT Thioredoxin DSG NADP-MDH).

The complete system for activation contained in 200 μl of 100 mM Tris-HCl buffer, pH 7.9 was 10 mM DTT, 0.7 μg corn leaf NADP-MDH, 0.25 μg wheat thioredoxin $\underline{h}$ and 10 μg of DSG-1 or DSG-2. In one study 20 mM β-mercaptoethanol (β-MET) was used instead of DTT. Following preincubation, NADP-MDH was assayed spectrophoto-metrically.

In the enzyme activation assays, thioredoxin $\underline{h}$ was reduced by DTT; as expected, monothiols such as β-mercaptoethanol (β-MET), which do not reduce thioredoxin at a significant rate under these conditions (Jacquot, J.-P. et al. (1981), *Plant Physiol.* 68:300–304; Nishizawa, A. N. et al. (1982), "Methods in Chloroplast Molecular Biology", (M. Edelman, R. B. Hallick and N.-H. Chua, eds.) pp. 707–714, Elsevier Biomedical Press, New York, and Crawford, N. A. et al. (1989), *Arch. Biochem. Biophys.* 271:223–239), did not replace DTT.

NADP-MDH activity was proportional to the level of added DSG-1 and DSG-2 at a constant thioredoxin $\underline{h}$ concentration. The same DTT formula was used as set forth above. Except for varying the DSG-1 or DSG-2 concentrations, conditions were identical to those previously described. When tested at a fixed DSG concentration, NADP-MDH showed enhanced activity with increasing thioredoxin $\underline{h}$. Except for varying the thioredoxin $\underline{h}$ concentration, conditions were as described above.

CM-1—the bread wheat protein that is similar to DSG proteins but has a lower molecular weight—also activated NADP-MDH and not FBPase when 20 μg of CM-1 were used as shown in Table I. The results indicate that thioredoxin $\underline{h}$ reduces a variety of α-amylase inhibitors, which, in turn, activate NADP-MDH in accordance with equations 4–6. These proteins were ineffective in enzyme activation when DTT was added in the absence of thioredoxin.

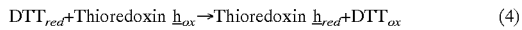

$$DTT_{red}+\text{Thioredoxin } \underline{h}_{ox} \rightarrow \text{Thioredoxin } \underline{h}_{red}+DTT_{ox} \quad (4)$$

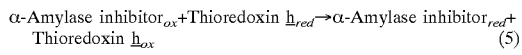

$$\alpha\text{-Amylase inhibitor}_{ox}+\text{Thioredoxin } \underline{h}_{red} \rightarrow \alpha\text{-Amylase inhibitor}_{red}+\text{Thioredoxin } \underline{h}_{ox} \quad (5)$$

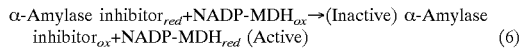

$$\alpha\text{-Amylase inhibitor}_{red}+\text{NADP-MDH}_{ox} \rightarrow (\text{Inactive}) \alpha\text{-Amylase inhibitor}_{ox}+\text{NADP-MDH}_{red} (\text{Active}) \quad (6)$$

TABLE I

Effectiveness of Thioredoxin-Reduced Trypsin Inhibitors, Thionins, and α-Amylase Inhibitors in Activating Chloroplast NADP-Malate Dehydrogenase and Fructose Bisphosphatase (DTT→Thioredoxin→Indicated Protein→Target Enzyme)
Activation of NADPH-MDH was carried out as described above in this Example except that the quantity of DSG or the other proteins tested was 20 μg. FBPase activation was tested using the standard DTT assay with 1 μg of *E. coli* thioredoxin and 20 μg of the indicated proteins. The above values are corrected for the limited activation seen with *E. coli* thioredoxin under these conditions.

| *ACTIVITY, nkat/mg Protein | $M_r$, kDa | No. of S—S Groups | NADP-MDH | FBPase |
|---|---|---|---|---|
| α-Amylase Inhibitors | | | | |
| **DSG-2 | 17 | 5 | 2 | 0 |
| **DSG-1 | 14 | 5 | 2 | 0 |
| ‡CM-1 | 12 | 5 | 12 | 0 |
| Trypsin Inhibitors | | | | |
| Cystine-rich (plant) | | | | |
| Corn kernel | 12 | 5 | 5 | 0 |
| Soybean Bowman-Birk | 8 | 7 | 3 | 0 |
| Other types | | | | |
| Ovomucoid | 28 | 9 | 2 | 0 |
| Soybean Kunitz | 20 | 2 | 2 | 0 |
| Ovoinhibitor | 49 | 14 | 1 | 0 |
| Bovine lung (Aprotinin) | 7 | 3 | Trace | 2 |
| Thionins | | | | |
| **Purothionin-$\alpha_1$ | 6 | 4 | 1 | 39 |
| **Purothionin-β | 6 | 4 | Trace | 5 |
| ‡Purothionin-α | 6 | 4 | 0 | 14 |

*These values compare to the corresponding values of 40 and 550 obtained, respectively, with spinach chloroplast thioredoxin $\underline{m}$ (NADP-MDH) and thioredoxin f.
**From Durum wheat
‡From bread wheat

EXAMPLE 2

DTNB Reduction Assays

A second test for thiol redox activity is the ability to catalyze the reduction of the sulfhydryl reagent, 2',5'-dithiobis(2-nitrobenzoic acid) (DTNB), measured by an increase in absorbance at 412 nm. Here, the protein assayed was reduced with NADPH via NTR and a thioredoxin. The DTNB assay proved to be effective for the α-amylase inhibitors from both durum (DSG-1 and 2) and bread wheat (CM-1). When reduced by the NADP/thioredoxin system (in this case using NTR and thioredoxin from *E. coli*), either DSG-1 or DSG-2 markedly enhanced the reduction of DTNB (NADPH→NTR→Thioredoxin→DSG→DTNB). The DTNB reduction assay was carried out with 10 μg thioredoxin and 10 μg NTR and 20 μg of DSG-1 or DSG-2. CM-1 was also effective in the DTNB reduction assay, and, as with NADP-MDH activation (Table I), was detectably more active than the DSG proteins The conditions for the CM-1 assay were the same as for the DSG/DTNB assay except that the DSG proteins were omitted and purothionin α, 20 µg or CM-1, 20 µg was used). The results thus confirmed the enzyme activation experiments in Example 1 and showed that the α-amylase inhibitors can be reduced physiologically by the NADP/thioredoxin system. The role of the α-amylase inhibitors in promoting the reduction of DTNB under these conditions is summarized in equations 7–9:

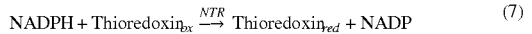  (7)

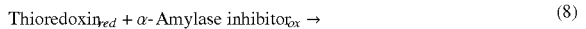 (8)

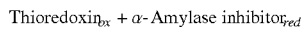

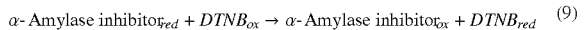 (9)

EXAMPLE 3

Protein Reduction Measurements

The availability of monobromobimane (mBBr) and its adaptation for use in plant systems has given a new technique for measuring the sulfhydryl groups of plant proteins (Crawford, N. A. et al. (1989), *Arch. Biochem. Biophys.* 271:223–239). When coupled with SDS-polyacrylamide gel electrophoresis, mBBr can be used to quantitate the change in the sulfhydryl status of redox active proteins, even in complex mixtures. This technique was therefore applied to the inhibitor proteins to confirm their capacity for reduction by thioredoxin. Here, the test protein was reduced with thioredoxin which itself had been previously reduced with either DTT or NADPH and NTR. The mBBr derivative of the reduced protein was then prepared, separated from other components by SDS-polyacrylamide gel electrophoresis and its reduction state was examined by fluorescence. In the experiments described below, thioredoxin from *E. coli* was found to be effective in the reduction of each of the targeted proteins. Parallel experiments revealed that thioredoxin h and calf thymus thioredoxins reduced, respectively, the proteins from seed and animal sources.

In confirmation of the enzyme activation and dye reduction experiments, DSG-1 was effectively reduced in the presence of thioredoxin. Following incubation the proteins were derivatized with mBBr and fluorescence visualized after SDS-polyacrylamide gel electrophoresis. Reduction was much less with DTT alone and was insignificant with GSH. A similar requirement for thioredoxin was observed for the reduction of CM-1 and DSG-2 (data not shown). While the thioredoxin used was from *E. coli* similar results were obtained with wheat thioredoxin h. Thioredoxin was also required when DTT was replaced by NADPH and NTR (data not shown).

EXAMPLE 4

Thioredoxin-linked Reduction of Cystine-Rich Plant Trypsin Inhibitors

Whereas the major soluble cystine-rich proteins of wheat seeds can act as inhibitors of exogenous α-amylases, the cystine-rich proteins of most other seeds lack this activity, and, in certain cases, act as specific inhibitors of trypsin from animal sources. While these proteins can be reduced with strong chemical reductants such as sodium borohydride (Birk, Y. (1985), *Int. J. Peptide Protein Res.* 25:113–131, and Birl, Y. (1976), *Meth. Enzymol.* 45:695–7390), there is little evidence that they can be reduced under physiological conditions. It was therefore of interest to test trypsin it inhibitors for the capacity to be reduced by thioredoxin. The cystine-rich representatives tested included the soybean Bowman-Birk and corn kernel trypsin inhibitors. The results in both cases were positive: each inhibitor activated NADP-MDH (but not FBPase) when added in the presence of DTT-reduced thioredoxin (Table I) and each reduced DTNB in the presence of NADPH, NTR and thioredoxin (data not shown).

As found for the α-amylase inhibitors, the thioredoxin-dependent reduction of the cystine-rich trypsin inhibitors could be directly monitored by the mBBr/SDS-polyacrylamide gel electrophoresis technique. Thus, significant reduction by DTT was observed only in the presence of reduced thioredoxin with both the Bowman-Birk (BBTI) inhibitor which showed a highly fluorescent fast moving band and corn kernel (CKTI) trypsin inhibitor which showed a highly fluorescent band migrating behind thioredoxin.

EXAMPLE 5

Thioredoxin-linked Reduction of Other Tryosin Inhibitors and Purothionins

In view of the finding that cystine-rich trypsin inhibitors from seeds can undergo specific reduction by thioredoxin, the question arose as to whether other types of trypsin inhibitor proteins share this property. In the course of this study, several such inhibitors—soybean Kunitz, bovine lung aprotinin, egg white ovoinhibitor and ovomucoid trypsin inhibitors—were tested. While the parameters tested were not as extensive as with the cystine-rich proteins described above, it was found that the other trypsin inhibitors also showed a capacity to be reduced specifically by thioredoxin as measured by both the enzyme activation and mBBr/SDS-polyacrylamide gel electrophoresis methods. As was the case for the cystine-rich proteins described above, the trypsin inhibitors tested in this phase of the study (soybean Kunitz and animal trypsin inhibitors) activated NADP-MDH but not FBPase (Table I). Bovine lung aprotinin was an exception in that it activated FBPase more effectively than NADP-MDH. It might also be noted that aprotinin resembles certain of the seed proteins studied here in that it shows a high content of cystine (ca. 10%) (Kassel, B. et al. (1965), *Biochem. Biophys. Res. Commun.* 20:463–468).

The fluorescence evidence for the thioredoxin-linked reduction of one of these proteins, the Kunitz inhibitor, was shown by a highly fluorescent slow moving band in an mBBr/SDS-polyacrylamide electrophoretic gel. In its reduced form, the Kunitz inhibitor also yielded a fluorescent fast moving band. The nature of this lower molecular mass species is not known. Its position on the gel suggests that it could represent Bowman-Birk inhibitor present as a contaminant in the Kunitz preparation; however, such a component was not evident in Coomassie Blue stained SDS gels. The animal inhibitors which yielded a single fluorescent band of the expected molecular weight, also showed a thioredoxin requirement for reduction (data not shown).

In confirmation of earlier results, thioredoxin-reduced purothionin consistently activated FBPase and the type tested earlier, purothionin-α, failed to activate NADP-MDH (Table I) (Wada, K. et at. (1981), *FEBS Lett.* 124:237–240). However, in contrast to purothionin-α from bread wheat, two purothionins previously not examined (purothionins α-1 and β from durum wheat) detectably activated NADP-MDH (Table I). The two durum wheat purothionins also differed in their ability to activate FBPase. The activity differences between these purothionins were unexpected in view of the strong similarity in their amino acid sequences (Jones, B. L. et al. (1977), *Cereal Chem.* 54:511–523) and in their ability to undergo reduction by thioredoxin. A requirement for thioredoxin was observed for the reduction of purothionin (here the α-type) by the SDS-PAGE fluorescence procedure.

EXAMPLE 6

Quantitation of Reduction

The above Examples demonstrate that thioredoxin reduces a variety of proteins, including α-amylase, such as the CM and DSG inhibitors, and trypsin inhibitors from seed as well as animal sources. While clear in the qualitative sense, the above results give no quantitative indication of the extent of reduction. Therefore, an experiment was conducted following the protocol of Crawford et al. (Crawford, N. A. et al. (1989), *Arch. Biochem. Biophys.* 271:223–239).

As shown in Table II, the extent of reduction of the seed inhibitor proteins by the *E. coli* NADP/thioredoxin system was time-dependent and reached, depending on the protein, 15 to 48% reduction after two hours. The results, based on fluorescence emitted by the major protein component, indicate that thioredoxin acts catalytically in the reduction of the α-amylase and trypsin inhibitors. The ratio of protein reduced after two hours to thioredoxin added was greater than one for both the most highly reduced protein (soybean Bowman-Birk trypsin inhibitor) and the least reduced protein (corn kernel trypsin inhibitor)—i.e., respective ratios of 7 and 2 after a two-hour reduction period. It should be noted that the values in Table II were obtained under standard assay conditions and no attempt was made to optimize reduction by modifying those conditions.

TABLE II

Extent of Reduction of Seed Proteins by the NADP/Thioredoxin System Using the mBBr/SDS-Polyacrylamide Gel Electrophoresis Procedure
The following concentrations of proteins were used (nmoles): thioredoxin, 0.08; NTR, 0.01; purothionin-β, 1.7; DSG-1, 0.7; corn kernel trypsin inhibitor, 1.0; Bowman-Birk trypsin inhibitor, 1.3; and Kunitz trypsin inhibitor, 0.5. Except for the indicated time difference, other conditions were as in Examples 1–4.

| Protein | % Reduction After | |
|---|---|---|
| | 20 min | 120 min |
| Purothionin-β | 15 | 32 |
| DSG-1 | 22 | 38 |
| Corn kernel trypsin inhibitor | 3 | 15 |
| Bowman-Birk trypsin inhibitor | 25 | 48 |
| Kunitz trypsin inhibitor | 14 | 22 |

EXAMPLE 7

*E. coli* Glutaredoxin as Reductant

Bacteria and animals are known to contain a thiol redox protein, glutaredoxin, that can replace thioredoxin in reactions such as ribonucleotide reduction (Holmgren, A. (1985), *Annu. Rev. Biochem.* 54:237–271). Glutaredoxin is reduced as shown in equations 10 and 11.

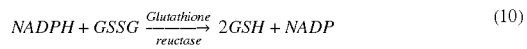

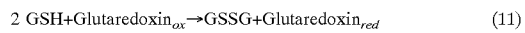

So far there is no evidence that glutaredoxin interacts with proteins from higher plants. This ability was tested, using glutaredoxin from *E. coli* and the seed proteins currently under study. Reduction activity was monitored by the mBBr/SDS polyacrylamide gel electrophoresis procedure coupled with densitometric scanning. It was observed that, under the conditions previously described, glutaredoxin could effectively replace thioredoxin in some, but not all cases. Thus, glutaredoxin was found to be active in the reduction of the following (the numbers indicate the percentage reduction relative to *E. coli* thioredoxin): DSG-1 and CM-1 α-amylase inhibitors (147 and 210%, respectively); corn kernel trypsin inhibitor (424%); and purothionin (82, 133, and 120% for the α, α1 and β forms, respectively). Glutaredoxin was ineffective in the reduction of the DSG-2 α-amylase inhibitor and the soybean Bowman-Birk and Kunitz trypsin inhibitors. The trypsin inhibitors from animal sources also showed a mixed response to glutaredoxin. Egg white ovoinhibitor was effectively reduced (55% reduction relative to *E. coli* thioredoxin) whereas egg white ovomucoid inhibitor and bovine lung aprotinin were not affected. Significantly, as previously reported (Wolosiuk, R. A. et al. (1977), *Nature* 266:565–567), glutaredoxin failed to replace thioredoxin as the immediate reductant in the activation of thioredoxin-linked enzymes of chloroplasts, FBPase and NADP-MDH (data not shown).

The above Examples demonstrate that some of the enzyme inhibitor proteins tested can be reduced by glutaredoxin as well as thioredoxin. Those specific for thioredoxin include an α-amylase inhibitor (DSG-2), and several trypsin inhibitors (Kunitz, Bowman-Birk, aprotinin, and ovomucoid inhibitor). Those proteins that were reduced by either thioredoxin or glutaredoxin include the purothionins, two α-amylase inhibitors (DSG-1, CM-1), a cystine-rich trypsin inhibitor from plants (corn kernel inhibitor), and a trypsin inhibitor from animals (egg white ovoinhibitor). These results raise the question of whether glutaredoxin occurs in plants. Glutaredoxin was reported to be present in a green alga (Tsang, M. L.-S. (1981), *Plant Physiol.* 68:1098–1104) but not in higher plants.

Although the activities of the NADP-MDH and FBPase target enzymes shown in Table I are low relative to those seen following activation by the physiological chloroplast proteins (thioredoxin $\underline{m}$ or $\underline{f}$), the values shown were found repeatedly and therefore are considered to be real. It seems possible that the enzyme specificity shown by the inhibitor proteins, although not relevant physiologically, reflects a particular structure achieved on reduction. It remains to be seen whether such a reduced structure is related to function within the seed or animal cell.

The physiological consequence of the thioredoxin (or glutaredoxin) linked reduction event is of considerable interest as the function of the targeted proteins is unclear. The present results offer a new possibility. The finding that thioredoxin reduces a wide variety of inhibitor proteins under physiological conditions suggests that, in the absence of compartmental barriers, reduction can take place within the cell.

EXAMPLE 8

Inactivation of Soybean Trypsin Inhibitor in Soybean Meal

The goal of this Example is to inactivate the Bowman-Birk and Kunitz trypsin inhibitors of soybeans, The following protocol applies to animal feed preparations. To 10 g of soybean meal are added 0.2 μg thioredoxin, 0.1 μg NADP-thioredoxin reductase and 500 nanamoles NADPH together with 1 M Tris-HCl buffer, pH 7.9, to give 5.25 ml of 30 mM Tris-HCl. The above mixture is allowed to sit for about 30 min at room temperature. Direct reduction of the soybean trypsin inhibitor is determined using the mBBr fluorescent labeling/SDS-polyacrylamide gel electrophoresis method previously described (Kobrehel, K. et al. (1991), *J. Biol. Chem.* 266:16135–16140). An analysis of the ability of the treated flour for trypsin activity is made using modifications of the insulin and BAEE (Na-benzoyl-L-arginine ethyl ester) assays (Schoellmann, G. et al. (1963), *Biochemistry* 252:1963; Gonias, S. L. et al. (1983), *J. Biol. Chem.* 258:14682). From this analysis it is determined that soybean meal so treated with the NADP/thioredoxin system does not inhibit trypsin.

EXAMPLE 9

Inactivation of α-Amylase Inhibitors in Cereals

To 10 g of barley malt are added 0.2 μg thioredoxin, 0.1 μg NADP-thioredoxin reductase and 500 nanamoles NADPH together with 1 M Tris-HCl buffer, pH 7.9, to give 5.25 ml of 30 mM Tris-HCl. The above mixture is allowed to sit for about 30 min at room temperature. Direct reduction of the α-amylase inhibitors is determined using the mBBr fluorescent labeling/SDS-polyacrylamide gel electrophoresis method previously described (Kobrehel, K. et al. (1991), *J. Biol. Chem.* 266:16135–16140). α-Amylase activity is monitored by following the release of maltose from starch (Bernfeld, P. (1955), *Methods in Enzymol.* 1:149). From this analysis it is determined that barley so treated with the NADP/thioredoxin system does not inhibit α-amylase.

Reduction of Cereal Proteins

Materials and Methods

Plant Material

Seeds and semolina of durum wheat (*Triticum durum*, Desf. cv. Monroe) were kind gifts of Dr. K. Kahn.

Germination of Wheat Seeds

Twenty to 30 seeds were placed in a plastic Petri dish on three layers of Whatman #1 filter paper moistened with 5 ml of deionized water. Germination was carried out for up to 4 days at room temperature in a dark chamber.

Reagents/Fine Chemicals

Biochemicals and lyophilized coupling enzymes were obtained from Sigma Chemical Co. (St. Louis, Mo.). *E. coli* thioredoxin and NTR were purchased from American Diagnostica, Inc. (Greenwich, Conn.). Wheat thioredoxin h and NTR were isolated from germ, following the procedures developed for spinach leaves (Florencio, F. J. et al. (1988), *Arch. Biochem. Biophys.* 266:496–507). *E. coli* glutaredoxin was a kind gift of Professor A. Holmgren. Reagents for SDS-polyacrylamide gel electrophoresis were purchased from Bio-Rad Laboratories (Richmond, Calif.). Monobromobimane (mBBr) or Thiolite was obtained from Calbiochem Co. (San Diego, Calif.). Aluminum lactate and methyl green were products of Fluka Chemicals Co. (Buchs, Switzerland).

Gliadins and Glutenins

For isolation of insoluble storage proteins, semolina (0.2 g) was extracted sequentially with 1 ml of the following solutions for the indicated times at 25° C.: (1) 50 mM Tris-HCl, pH 7.5 (20 min); (2) 70% ethanol (2 hr); and (3) 0.1 M acetic acid (2 hr). During extraction, samples were placed on an electrical rotator and, in addition, occasionally agitated with a vortex mixer. After extraction with each solvent, samples were centrifuged (12,000 rpm for 5 min) in an Eppendorf microfuge and, supernatant fractions were saved for analysis. In between each extraction, pellets were washed with 1 ml of water, collected by centrifugation as before and the supernatant wash fractions were discarded. By convention, the fractions are designated: (1) albumin/globulin; (2) gliadin; and (3) glutenin.

In vitro mBBr Labelling of Proteins

Reactions were carried out in 100 mM Tris-HCl buffer, pH 7.9. As indicated, 0.7 μg NTR and 1 μg thioredoxin (both from *E. coli* unless specified otherwise) were added to 70 μl of this buffer containing 1 mM NADPH and 10 μg of target protein. When thioredoxin was reduced by dithiothreitol (DTT), NADPH and NTR were omitted and DTT was added to 0.5 mM. Assays with reduced glutathione were performed similarly, but at a final concentration of 1 mM. After incubation for 20 min, 100 nmoles of mBBr were added and the reaction was continued for another 15 min. To stop the reaction and derivatize excess mBBr, 10 μl of 10% SDS and 10 μl of 100 mM β-mercaptoethanol were added and the samples were then applied to the gels. For reduction by glutaredoxin, the thioredoxin and NTR were replaced by 1 μg *E. coli* glutaredoxin, 1.4 μg glutathione reductase (purified from spinach leaves) and 1.5 mM NADPH.

In vivo mBBr Labelling of Proteins

At the indicated times, the dry seeds or germinating seedlings (selected on the basis of similar radical length) were removed from the Petri dish and their embryos or germinated axes were removed. Five endosperms from each lot were weighed and then ground in liquid $N_2$ with a mortar and pestle. One ml of 2.0 mM mBBr in 100 mM Tris-HCl, pH 7.9, buffer was added just as the last trace of liquid $N_2$ disappeared. The thawed mixture was then ground for another minute and transferred to a microfuge tube. The volume of the suspension was adjusted to 1 ml with the appropriate mBBr or buffer solution. Protein fractions of albumin/globulin, gliadin and glutenin were extracted from endosperm of germinated seedlings as described above. The extracted protein fractions were stored at −20° C. until use. A buffer control was included for each time point.

SDS-Polyacrylamide Gel Electrophoresis

SDS-polyacrylamide electrophoresis of the mBBr-derivatized samples was performed in 15% gels at pH 8.5 as described by Laemmli, U.K. (1970), *Nature* 227:680–685. Gels of 1.5 mm thickness were developed for 16 hr. at a constant current of 9 mA.

Native Gel Electrophoresis

To resolve the different types of gliadins, native polyacrylamide gel electrophoresis was performed in 6% gels (a procedure designed to separate gliadins into the four types) as described by Bushuk and Zillman (Bushuk, W. et al. (1978), *Can. J. Plant Sci.* 58:505–515) and modified for vertical slab gels by Sapirstein and Bushuk (Sapirstein, H. D. et al. (1985), *Cereal Chem.* 62:372–377). A gel solution in 100 ml final volume contained 6.0 g acrylamide, 0.3 g bisacrylamide, 0.024 g ascorbic acid, 0.2 mg ferrous sulfate heptahydrate and 0.25 g aluminum lactate. The pH was adjusted to 3.1 with lactic acid. The gel solution was degassed for 2 hr. on ice and then 0.5 ml of 3% hydrogen peroxide was added as a polymerization catalyst. The running buffer, also adjusted to pH 3.1 with lactic acid, contained 0.5 g aluminum lactate per liter. Duration of electrophoresis was approximately 4 hr., with a constant current of 50 mA. Electrophoresis was terminated when the solvent front, marked with methyl green tracking dye, migrated to about 1 cm from the end of the gel.

mBBr Removal/Fluorescence Photography

Following electrophoresis, gels were placed in 12% (w/v) trichloroacetic acid and soaked for 4 to 6 hr. with one change of solution to fix the proteins; gels were then transferred to a solution of 40% methanol/10% acetic acid for 8 to 10 hr. to remove excess mBBr. The fluorescence of mBBr, both free and protein bound, was visualized by placing gels on a light box fitted with an ultraviolet light source (365 nm). Following removal of the excess (free) mBBr, gels were photographed with Polaroid Positive/Negative Landfilm, type 55, through a yellow Wratten gelatin filter No. 8 (cutoff=460 nm) (exposure time ranged from 25 to 60 sec at f4.5) (Crawford, N. A. et al. (1989), *Arch. Biochem. Biophys.* 271:223–239).

Protein Staining/Destaining/Photography

SDS-gels were stained with Coomassie Brilliant Blue R-250 in 40% methanol/10% acetic acid for 1 to 2 hr. and destained overnight as described before (Crawford, N. A. et al. (1989), *Arch. Biochem. Biophys.* 271:223–239). Aluminum lactate native gels were stained overnight in a filtered solution containing 0.1 g Coomassie Brilliant Blue R-250 (dissolved in 10 ml 95% ethanol) in 240 ml 12% trichloroacetic acid. Gels were destained overnight in 12% trichloroacetic acid (Bushuk, W. et al. (1978), *Can. J. Plant Sci.* 58:505–515, and Sapirstein, H. D. et al. (1985), *Cereal Chem.* 62:372–377).

Protein stained gels were photographed with Polaroid type 55 film to produce prints and negatives. Prints were used to determine band migration distances and loading efficiency.

The Polaroid negatives of fluorescent gels and prints of wet protein stained gels were scanned with a laser densitometer (Pharmacia-LKB UltroScan XL). Fluorescence was quantified by evaluating peak areas after integration with GelScan XL software.

Enzyme Assays

The following activities were determined in crude extracts with previously described methods: hexokinase (Baldus, B. et at. (1981), *Phytochem.* 20:1811–1814), glucose-6-phosphate dehydrogenase, 6-phosphogluconate dehydrogenase (Schnarrenberger, C. et al. (1973), *Arch. Biochem. Biophys.* 154:438–448), glutathione reductase, NTR and thioredoxin h (Florencio, F. J. et al. (1988), *Arch. Biochem. Biophys.* 266:496–507).

Protein Determination

Protein concentrations were determined by the Bradford method (Bradford, M. (1976) *Anal. Biochem.* 72:248–256), with Bio-Rad reagent and bovine serum albumin as a standard.

Subunit Molecular Weight Determination

The subunit molecular weight of gliadins and glutenins was estimated on SDS-PAGE gels by using two sets of molecular weight standards (kDa). The first set consisted of BSA (66), ovalbumin (45), soybean trypsin inhibitor (20.1), myoglobin (17), cytochrome c (12.4) and aprotinin (6.5). The other set was the BioRad Prestained Low SDS-PAGE standards: phosphorylase b (110), BSA (84), ovalburnin (47), carbonic anhydrase (33), soybean trypsin inhibitor (24) and lysozyme (16).

EXAMPLE 10

Reduction of Gliadins

As a result of the pioneering contributions of Osborne and coworkers a century ago, seed proteins can be fractionated on the basis of their solubility in aqueous and organic solvents (20). In the case of wheat, preparations of endosperm (flour or semolina) are historically sequentially extracted with four solutions to yield the indicated protein fraction: (i) water, albumins; (ii) salt water, globulins; (iii) ethanol/water, gliadins; and (iv) acetic acid/water, glutenins. A wide body of evidence has shown that different proteins are enriched in each fraction. For example, the albumin and globulin fractions contain numerous enzymes, and the gliadin and glutenin fractions are in the storage proteins required for germination.

Examples 1, 4 and 5 above describe a number of water soluble seed proteins (albumins/globulins, e.g., α-amylase inhibitors, cystine-rich trypsin inhibitors, other trypsin inhibitors and thionines) that are reduced by the NADP/thioredoxin system, derived either from the seed itself or *E. coli*. The ability of the system to reduce insoluble storage proteins from wheat seeds, viz., representatives of the gliadin and glutenin fractions, is described below. Following incubation with the indicated additions, the gliadin proteins were derivatized with mBBr and fluorescence was visualized after SDS-polyacrylamide gel electrophoresis. The lanes in this first gliadin gel were as follows: 1. Control: no addition. 2. GSH/GR/NADPH: reduced glutathione, glutathione reductase (from spinach leaves) and NADPH. 3. NGS: NADPH, reduced glutathione, glutathione reductase (from spinach leaves) and glutaredoxin (from *E. coli*). 4. NTS: NADPH, NTR, and thioredoxin (both proteins from *E. coli*). 5. MET/T(Ec): β-mercaptoethanol and thioredoxin (*E. coli*). 6. DTT. 7. DTT/T(Ec): DTT and thioredoxin (*E. coli*). 8. DTT/T(W): Same as 7 except with wheat thioredoxin h. 9. NGS,-Gliadin: same as 3 except without the gliadin protein fraction. 10. NTS,-Gliadin: same as 4 except without the gliadin protein fraction. Based on its reactivity with mBBr, the gliadin fraction was extensively reduced by thioredoxin. The major members undergoing reduction showed a Mr ranging from 25 to 45 kDa. As seen in Examples 1, 4 and 5 with the seed α-amylase and trypsin inhibitor proteins, the gliadins were reduced by either native h or *E. coli* type thioredoxin (both homogeneous); NADPH (and NTR) or DTT could serve as the reductant for thioredoxin. Much less extensive reduction was observed with glutathione and glutaredoxin—a protein able to replace thioredoxin in certain *E. coli* and mammalian enzyme systems, but not known to occur in higher plants.

The gliadin fraction is made up of four different protein types, designated α, β, γ and ω, which can be separated by native polyacrylamide gel electrophoresis under acidic conditions (Bushuk, W. et al. (1978), *Can. J. Plant Sci.* 58:505–515; Kasarda, D. D. et al. (1976), *Adv. Cer. Sci. Tech.* 1:158–236; Sapirstein, H. D. et al. (1985), *Cereal Chem.* 62:372–377; and Tatham, A. S. et al. (1990), *Adv. Cer. Sci. Tech.* 10:1–78). Except for the ω gliadins, each species contains cystine (S—S) groups and thus has the potential for reduction by thioredoxin. In this study, following incubation with the indicated additions, proteins were derivatized with mBBr, and fluorescence was visualized after acidic-polyacrylamide gel electrophoresis. The lanes in the second gliadin gel in this study were as follows: 1. Control: no addition. 2. GSH: reduced glutathione. 3. GSH/GR/NADPH: reduced glutathione, glutathione reductase (from spinach leaves) and NADPH. 4. NGS: NADPH, reduced glutathione, glutathione reductase (from spinach leaves) and glutaredoxin (from *E. coli*). 5. NGS+NTS: combination of 4 and 6. 6. NTS: NADPH, NTR, and thioredoxin (both proteins from *E. coli*). 7. MET/T(Ec): β-mercaptoethanol and thioredoxin (*E. coli*). 8. DTT/T(Ec): DTT and thioredoxin (*E. coli*). 9. NTS(-T): same as 6 except without thioredoxin. 10. NGS+NTS,-Gliadin: same as 5 except without the gliadin fraction.

When the thioredoxin-reduced gliadin fraction was subjected to native gel electrophoresis, the proteins found to be most specifically reduced by thioredoxin were recovered in the a fraction. There was active reduction of the β and γ gliadins, but as evident from the densitometer results summarized in Table III, the reduction within these groups was nonspecific, i.e., relatively high levels of reduction were also achieved with glutathione and glutaredoxin. There was especially strong reduction of the γ gliadins by DTT-reduced thioredoxin. As anticipated, there was no reduction of the ω gliadins. The evidence indicates that thioredoxin (either native h or *E. coli*) specifically reduces certain of the gliadins, especially the α type.

TABLE III

Reductant Specificity of the Different Types of Gliadins
The area under α, β, γ and aggregate peaks following reduction by the NADP/thioredoxin system were: 4.33, 8.60, 5.67 and 0.74 Absorbance units times millimeters, respectively. These combined areas were about 65% of those observed when thioredoxin was reduced by DTT with the second gel, with the reaction conditions as in Example 10.

| Reductant | Gliadin, % Relative Reduction | | | |
|---|---|---|---|---|
| | α | β | γ | Aggregate* |
| None | 22.4 | 30.4 | 24.3 | 29.2 |
| Glutathione | 36.4 | 68.1 | 60.6 | 60.1 |
| Glutaredoxin | 43.5 | 83.3 | 79.7 | 61.5 |
| Thioredoxin | 100.0 | 100.0 | 100.0 | 100.0 |

*Proteins not entering the gel

EXAMPLE 11

Reduction of Glutenins

The remaining group of seed proteins to be tested for a response to thioredoxin—the glutenins—while the least water soluble, are perhaps of greatest interest. The glutenins have attracted attention over the years because of their importance for the cooking quality of flour and semolina (MacRitchie, F. et al. (1990), *Adv. Cer. Sci. Tech.* 10:79–145). Testing the capability of thioredoxin to reduce the proteins of this group was, therefore, a primary goal of the current investigation.

Several glutenins were reduced specifically by thioredoxin when the mBBr/SDS-page technique was applied and the conditions were as in Example 10 with the first gel. The most extensive reduction was observed in the low molecular mass range (30–55 kDa). The reduction observed in the higher molecular mass range was less pronounced, but still obvious—especially in the 100 kDa region and above. Though not shown reduction a may also occur in the 130 kDa range. Like the gliadins, certain of the glutenins were appreciably reduced by glutathione and glutaredoxin. However, in all cases, reduction was greater with thioredoxin and, in some cases, specific to thioredoxin (Table IV, note proteins in the 30–40 and 60–110 kDa range). As observed with the other wheat proteins tested, both the native h anal *E. coli* thioredoxins were active and could be reduced with either NADPH and the corresponding NTR or with DTT. Thus as found for the gliadins, certain glutenins were reduced in vitro specifically by thioredoxin, whereas others were also reduced, albeit less effectively, by glutathione and glutaredoxin.

TABLE IV

Reductant Specificity of Glutenins
Reaction conditions as in the Example 1 study of the effect of thioredoxin h concentration on the activation of NADP-MDH by DSG-1 or -2 α-amylase inhibitors.

| Reductant | Glutenin, % Relative Reduction* | | |
|---|---|---|---|
| | 60–110 kDa | 40–60 kDa | 30–40 kDa |
| None | 8 | 23 | 16 |
| Glutathione | 31 | 51 | 29 |
| Glutaredoxin | 50 | 72 | 40 |
| Thioredoxin* | 100 | 100 | 100 |

*Area under the three molecular weight classes (from high to low) following reduction by the NADP/thioredoxin system were: 1.5, 5.67 and 5.04 Absorbance units times millimeters, respectively.

EXAMPLE 12

In vivo Reduction Experiments

The above Example demonstrates that thioredoxin specifically reduces components of the wheat gliadin and glutenin fractions when tested in vitro. The results, however, provide no indication as to whether these proteins are reduced in vivo during germination—a question that, to our knowledge, had not been previously addressed (Shutov, A. D. et al. (1987), *Phytochem.* 26:1557–1566).

To answer this question, the mBBr/SDS-PAGE technique was applied to monitor the reduction status of proteins in the germinating seed. We observed that reduction of components in the Osborne fractions increased progressively with time and reached a peak after 2 to 3 days germination.

The observed increase in reduction ranged from 2-fold with the gliadins, to 3-fold with the albumin/globulins and 5-fold with the glutenins. The results suggest that, while representatives of the major wheat protein groups were reduced during germination, the net redox change was greatest with the glutenins.

Although providing new evidence that the seed storage proteins undergo reduction during germination, the results give no indication as to how reduction is accomplished, i.e., by glutathione or thioredoxin. To gain information on this point, the in vivo reduction levels of the principal thioredoxin-linked gliadins (30–50 kDa) and glutenins (30–40, 40–60 kDa) was compared with the reduction determined from in vitro measurements (cf. Table IV). For this purpose, the ratio of fluorescence to Coomassie stained protein observed in vivo during germination and in vitro with the appropriate enzyme reduction system was calculated. The results (principal thioredoxin linked gliadins were those in the Mr range from 25 to 45 kDa, and glutenins were those in the Mr range from 30 to 60 kDa) suggest that, while glutathione could account for a significant part of the in vivo reduction of the gliadin fraction (up to 90%), this was not the case with the glutenins whose reduction seemed to require thioredoxin. The level of reduction that could be ascribed to glutathione (or glutaredoxin) was insufficient to account for the levels of reduced glutenin measured in the germinating seed.

EXAMPLE 13

Enzyme Measurements

The source of NADPH needed for the NTR linked reduction of thioredoxin h was also investigated. Semolina was analyzed for enzymes that function in the generation of NADPH in other systems, notably dehydrogenases of the oxidative phosphate pathway. The results summarized in Table V confirm earlier evidence that endosperm extracts contain the enzymes needed to generate NADPH from glucose via this pathway: hexokinase, glucose 6-phosphate dehydrogenase and 6-phosphogluconate dehydrogenase (Tatham, A. S. et al. (1990), *Adv. Cer. Sci. Tech.* 10:1–78). It is noteworthy that the glucose 6-phosphate dehydrogenase activity seen in Table V was insensitive to reduced thioredoxin (data not shown). In this respect the endospermn enzyme resembles its cytosolic rather than its chloroplast counterpart from leaves (Fickenscher, K. et al. (1986), *Arch. Biochem. Biophys.* 247:393402; Buchanan, B. B. (1991), *Arch. Biochem. Biophys.* 288:1–9; Scheibe, R. et al. (1990), *Arch. Biochem. Biophys.* 274:290–297).

As anticipated from earlier results with flour (Johnson, T. C. et al. (1987), *Planta* 171:321–331; Suske, G. et al. (1979), *Z. Naturforsch. C* 34:214–221), semolina also contained thioredoxin h and NTR (Table V). Interestingly, based on activity measurements, NTR appeared to be a rate-limiting component in preparations from the cultivar examined.

TABLE V

Activities of Enzymes Effecting
the Reduction of Thioredoxin h in Semolina
(Glucose→Glu-6-P→6-P-Gluconate→NADP→Thioredoxin h)

| Protein | Activity (nkat/mg protein) |
| --- | --- |
| Hexokinase | 0.28 |
| Glucose-6-P dehydrogenase | 0.45 |
| 6-P-Gluconate dehydrogenase | 0.39 |
| NTR | 0.06 |
| Thioredoxin h | 0.35 |

The present results suggest that thioredoxin h functions as a signal to enhance metabolic processes associated with the germination of wheat seeds. Following its reduction by NTR and NADPH (generated via the oxidative pentose phosphate pathway), thioredoxin h appears to function not only in the activation of enzymes, but also in the mobilization of storage proteins.

EXAMPLE 14

Improvement of Dough Quality

Dough quality was improved by reducing the flour proteins using the NADP/thioredoxin system. Reduced thioredoxin specifically breaks sulfur-sulfur bonds that cross-link different parts of a protein and stabilize its folded shape. When these cross-links are cut the protein can unfold and link up with other proteins in bread, creating an interlocking lattice that forms the elastic network of dough. The dough rises because the network traps carbon dioxide produced by yeast in the fermenting process. It is proposed that the reduced thioredoxin activated the gliadins and glutenins in flour letting them recombine in a way that strengthened the dough. Reduced thioredoxin strengthened the protein network formed during dough making. For these tests (using 10 gm of either intermediate quality wheat flour obtained from a local miller in Montpellier, France, or poor quality wheat also obtained from a local miller in Montpellier, France, this poor quality wheat being mainly of the Apollo cultivar), 0.2 $\mu$g *E. coli* thioredoxin, 0.1 $\mu$g *E. coli* NADP-thioredoxin reductase and 500 nanomoles NADPH were added together with 1 M Tris-HCl, pH 7.9 buffer to give 5.25 ml of a 30 mM Tris-HCl enzyme system mixture. The reaction was carried out by mixing the enzyme system mixture with the 10 gm of the flour in a micro-farinograph at 30° C. The resulting farinograph measurements showed a strengthening of the dough by the added NADP/thioredoxin system. With a flour of poor quality, the farinograph reading was stable for at least 4 min after the dough was formed in the presence of the reduction system, whereas the reading dropped immediately after dough formation in the control without this addition. The improving effect was persistent and was maintained throughout the run. Expressed another way, the micro-farinograph reading is 375 Brabender units, 7 min after dough formation with the poor quality wheat control (no added enzyme system) versus 450 Brabender units for the same poor quality wheat treated with components of the NADP/thioredoxin system (NADPH, thioredoxin and NADP-thioredoxin reductase).

Another farinograph study was carried out as above with 10 gm of Apollo flour only the concentration of NADPH was 500 $\mu$moles instead of nanomoles. The farinograph measurements showed that this amount of NADPH also resulted in a definite improvement in the quality of the dough.

Higher farinograph measurements of dough correspond to improved dough strength and improved baked good characteristics such as better crumb quality, improved texture and higher loaf volume. Also, based on in vivo analyses with the isolated proteins, the native wheat seed NADP/thioredoxin system will also be effective in strengthening the dough.

For purposes of baking and other aspects of this invention, ranges of about 0.1 to 3.0 $\mu$g of a thioredoxin (preferably *E. coli* or thioredoxin h) and from about 0.1 to 2.0 $\mu$g reductase and about 30 to 500 nanomoles of NADPH are added for about every 10 gm of flour. The optimal levels of thioredoxin and reductase depend on flour quality. In general, the higher the flour quality, the higher the level of thioredoxin and reductase required. Thioredoxin can also be reduced by lipoic acid instead of by the NADPH/NADP-thioredoxin reductase reduction system. The other dough ingredients such as milk or water are then added. However, the liquid may first be added to the NTR/thioredoxin system and then added to the flour.

It is preferred that yeast for purposes of leavening be added after the reduced thioredoxin has had a chance to reduce the storage proteins. The dough is then treated as a regular dough proofed, shaped, etc. and baked.

NADPH can be replaced in this Example as well as in the following Examples with an NADPH generator such as one consisting of 100 $\mu$M glucose 6-phosphate, 100 $\mu$M NADP and 0.05 units (0.2 $\mu$gram) glucose 6-phosphate dehydrogenase from a source such as yeast. The NADPH generator is added together with thioredoxin and NADP-thioredoxin reductase at the start of the dough making process.

A higher farinograph measurement was obtained when 10 gm of Apollo cultivar (CV) wheat were reacted with 20 $\mu$l NADP (25 mM), 20 $\mu$l G6P (25 mM), 0.25 $\mu$g G6PDase, 0.1 $\mu$g NTR and 0.2 $\mu$g thioredoxin h contained in 4.25 ml $H_2O$ and 0.90 ml Tris-HCl (30 mM, pH 7.9). A higher farinograph measurement was also obtained when 10 gm of Apollo wheat were reacted with this same reaction mixture but without any NTR or thioredoxin.

EXAMPLE 15

Wheat Bread Baking Studies

The baking tests were carried out by using a computer monitored PANASONIC baking apparatus.

| Composition of bread: | | |
|---|---|---|
| Control: | Flour*: | 200 gm (dry) |
| | Water: | 70% hydratation |
| | Salt (NaCl): | 5.3 g |
| | Yeast: | 4.8 g |
| | | (*Saccharomiyces cerevisiae*, SafInstant) |
| | | (dry yeast powder) |

*Flour samples were obtained from pure bread wheat cultivars having contrasting baking quality (including animal feed grade and other grades having from poor to good baking quality).

Assays

The dough for the assays contained all the components of the control plus as indicated varying amounts of the NADP Thioredoxin System (NTS) and/or the NADP generating System.

Experimental Conditions

Flour and salt are weighed and mixed

The volume of water needed to reach a hydratation of 70% was put into the baking pan.

The mixture of flour and salt was added to the water and the baking program monitored by the computer was started. The complete program lasted 3 hrs 9 min and 7 secs.

In the case of the assays, enzyme system components are added to the water before the addition of the flour-salt mixture.

Yeast was added automatically after mixing for 20 min and 3 secs.

The program monitoring the Panasonic apparatus was:

| Segments | Duration | Mixing Conditions | Heating |
|---|---|---|---|
| Mixing | 00:00:03 | T1 | off |
| Mixing | 00:05:00 | T2 | off |
| Mixing | 00:05:00 | T1 | off |
| Rest | 00:10:00 | T0 | off |
| Mixing | 00:17:00 | T2 | off |
| Mixing | 00:07:00 | T1 | off |
| Rest | 00:30:00 | T0 | to reach 32° C. |
| Mixing | 00:00:04 | T1 | 32° C. |
| Rest | 01:15:00 | T0 | 32° C. |
| Baking | 00:14:00 | T0 | to reach 180° C. |
| Baking | 00:26:00 | T0 | 180° C. |

Mixing Conditions:
T0 = no mixing (motor at rest)
T1 = normal mixing
T2 = alternately 3 second mixing, 3 second rest Bread loaf volume was determined at the end of the baking, when bread loaves reached room temperature.

Cultivar THESEE Assay

The french wheat cultivar Thesee is classified as having good breadmaking quality. Table VI below sets forth the results of the assay.

TABLE VI

| | NADPH ($\mu$moles) | NTR ($\mu$g) | Th ($\mu$g) | Loaf Volume (cm3) | Relative Units |
|---|---|---|---|---|---|
| Control | 0 | 0 | 0 | 1690 | 100 |
| Samples | 6.0 | 30 | 60 | 1810 | 107 |
| | 6.0 | 30 | 0 | 1725 | 102 |
| | 6.0 | 0 | 60 | 1720 | 102 |
| | 6.0 | 0 | 0 | 1550 | 92 |
| | 0 | 30 | 60 | 1800 | 107 |
| *NADPH Generating syst. | | 30 | 60 | 1620 | 96 |
| *NADPH Generating syst. plus ATP, glucose | | 30 | 60 | 1630 | 96 |
| NTR and Th from yeast | 6.0 | 9.4 | 20 | 1750 | 104 |

| Volume Added | |
|---|---|
| NADP, 25 mMolar | 700 $\mu$l (17.5 $\mu$moles) |
| Glucose-6-phosphate, 25 mMolar | 700 $\mu$l (17.5 $\mu$moles) |
| Glucose-6-phosphate dehydrogenase (50 $\mu$g/ml) | 175 $\mu$l (8.75 $\mu$g) |
| ATP, 25 mMolar | 700 $\mu$l (17.5 $\mu$moles) |
| Glucose, 25 mMolar | 700 $\mu$l (17.5 $\mu$moles) |

*Composition of the NADPH generating system, ATP and glucose.

As shown in Table VI, an increased loaf volume was obtained when the complete NTS at concentrations of 6.0 $\mu$moles NADPH, 30 $\mu$g NTR and 60 $\mu$g Th was used to bake loaves from 200 g of Thesee flour with the amounts and conditions described above in this Example. Unless otherwise stated, the NTR and thioredoxin (th) were from *E. coli*. No similar increase occurred when the generating system was used or when either NTR or Th were omitted. Also no significant effect on loaf volume occurred when amounts of the components in the system were about half or less than half of the amounts of above.

Cultivar APOLLO Assay

This French wheat cultivar is classified as having poor breadmaking quality. The NTR and thioredoxin used in this assay were from *E. coli*. Table VII below sets forth the results of this assay using 200 gm of Apollo flour. Again unless otherwise stated the amounts and conditions are those described above at the beginning of the Example.

TABLE VII

| | NADPH ($\mu$moles) | NTR ($\mu$g) | Th ($\mu$g) | Loaf Volume (cm3) | Relative Units |
|---|---|---|---|---|---|
| Control | 0 | 0 | 0 | 1400 | 100 |
| Samples | 6.0 | 30 | 60 | 1475 | 105 |
| *NADPH Generating syst. plus ATP, glucose | | 30 | 60 | 1530 | 109 |
| *NADPH Generating syst. plus ATP, glucose | | 0 | 0 | 1430 | 102 |
| *NADPH Generating syst. | | 6 | 0 | 1430 | 102 |
| *NADPH Generating syst. | | 6 | 7 | 1440 | 103 |

*The composition of the generating system, ATP and glucose is as in Table VI.

Cultivar ARBON Assay

The French wheat cultivar Arbon is used for feed and is classified as non suitable for breadmaking. Tables VIII and IX below show that an improved bread loaf volume can be obtained from Arbon using the NTS or NADPH and NTR with the dough components and conditions described at the beginning of the Example. The amounts of NTR, thioredoxin, NADPH and the NADPH generating system components used in the assay are set forth in Tables VIII and IX. The improvement in Arbon bread quality using the complete NTS as set forth in Table IX was clearly visible when compared to the control.

TABLE VIII

|  | NADPH (μmoles) | NTR (μg) | Th (μg) | Loaf Volume (cm3) |
|---|---|---|---|---|
| Control | 0 | 0 | 0 | 1350 |
| Samples | 0.1–0.6 | 3–4 | 3–4 | up to 20% higher than the control |
|  | >2.0 | >20 | >20 | less than the control |

TABLE IX

|  | Loaf Volume | |
|---|---|---|
| Treatment | (cm3) | Relative Units |
| Complete NTS | 1650 | 122 |
| minus Thioredoxin | 1690 | 125 |
| minus NTR | 1520 | 113 |
| minus Thioredoxin, NTR | 1540 | 114 |
| minus NADPH | 1440 | 107 |
| minus NADPH, plus *NADPH generating system | 1560 | 116 |
| minus NTS (control) | 1350 | 100 |

NADPH, 0.6 μmoles
Thioredoxin, 3.5 μg
NTR, 3 μg
*Generating System:
3.5 μmoles NADP
3.5 μmoles glucose-6-phosphate
1.75 μg glucose-6-phosphate dehydrogenase

EXAMPLE 16

Triticale Bread Baking Study

Triticale is a wheat/rye hybrid and is generally used for chicken feed. It is more nutritious than wheat but is not generally considered appropriate for breadmaking, especially in the more developed nations. The effect of the NTS system and variations thereof on loaves baked from Triticale flour was consequently studied. Unless otherwise stated, the baking conditions and dough ingredient were as described for wheat flour in Example 15. As shown in Table X there is an improvement in loaf volume when the triticale dough contained thioredoxin, NTR and the NADPH generating system in the amounts set forth in that Table. However, no corresponding improvement was seen when the NTS (i.e., thioredoxin, NTR and NADPH) was used. An improvement in the texture of the bread, making it more cohesive and stable, also occurred when NTR, Th and the NADPH generating system as set forth in Table X were used.

TABLE X

Effect of the NADP/Thioredoxin System (NTS) on Loaves Baked from Triticale Flour (cv. Juan)

|  | Loaf Volume | |
|---|---|---|
| Treatment | (cm3) | Relative Units |
| Complete NTS | 1230 | 94 |
| minus NTS (control) | 1310 | 100 |
| minus NADPH, plus *NADPH | 1390 | 106 |

NADPH, 0.6 μmoles
Thioredoxin, 3.5 μg
NTR, 3.0 μg
Generating System:
4.5 μmoles NADP
4.5 μmoles glucose-6-phosphate
4.5 μg glucose-6-phosphate dehydrogenase

EXAMPLE 17

The effect of the NADPH/thioredoxin system on flour from sorghum, corn and rice was also determined. The baking conditions were as described for wheat flour in Example 15. The amounts of the components of the NTS as used in this assay were as follows: 8 μmoles NADPH, 40.5 μg NTR and 54 μg thioredoxin. Both the thioredoxin and NTR were from *E. coli*. The breads in this study containing the NTS, especially corn and sorghum exhibited improved texture and stability.

EXAMPLE 18

Reduction of Ethanol-Soluble and Myristate-Soluble Storage Proteins from Triticale, Rye, Barley, Oat, Rice, Sorghum, Corn and Teff Unless otherwise stated, the materials and methods used in this Example are according to those set forth above in the section tided "Reduction of Cereal Proteins, Materials and Methods."

Triticale, Rye, Barley, Oat and Teff

The reactions were carried out in 30 mM Tris-HCl buffer, pH 7.9. As indicated, 0.7 μg of NTR and 1 μg of thioredoxin from *E. coli* or 2 μg of thioredoxin from yeast, as identified, were added to 70 μL of this buffer containing 1 mM NADPH and 25 to 30 μg of extracted storage protein. The ethanol extracted storage proteins were obtained by using 50 ml of 70% ethanol for every 10 gm of flour and extracting for 2 hr. In the case of teff, 200 mg of ground seeds were extracted. The myristate extracted proteins were obtained by extracting 1 gm of flour with 8 mg sodium myristate in 5 ml of distilled $H_2O$ for 2 hrs. The combination of NADPH, NTR and thioredoxin is known as the NADP/thioredoxin system (NTS). As indicated, glutathione (GSH), 2.5 mM, was added as reductant in either the absence (GSH) or presence of 1.5 mM NADPH and 1.4 μg of spinach leaf glutathione reductase (GR/GSH/NADPH). After incubation for 20 min, 100 nmol of mBBr was added and the reaction was continued for another 15 min. To stop the reaction and derivatize excess mBBr, 10 μL of 10% SDS and 10 μL of 100 mM 2-mercaptoethanol were added, and the samples were then applied to the gels. The procedure for SDS-polyacrylamide gel electrophoresis was as described by N. A. Crawford et al. (1989 *Arch. Biochem. Biophys.* 271:223–239).

Rice, Sorghum and Corn

The reactions were carried out in 30 mM Tris-HCl buffer, pH 7.9. When proteins were reduced by thioredoxin, the following were added to 70 μL of buffer: 1.2 mM NADPH, 10 to 30 μg of seed protein fraction, 0.5 μg E. coli NTR and 1 μg E. coli thioredoxin. For reduction with glutathione, thioredoxin and NTR were replaced with 2.5 mM reduced glutathione and 1 μg glutathione reductase (baker's yeast, Sigma Chemical Co.). For reduction with dithiothreitol, NADPH, thioredoxin, and NTR were omitted and 0.5 mM dithiothreitol was added. In all cases, incubation time was 20 min. Then 10 μl of a 10 mM mBBr solution was added and the reaction continued for an additional 15 min. To stop the reaction and derivatize excess mBBr, 10 μl of 10% SDS and 10 μl of 100 mM 2-mercaptoethanol were added and the samples applied to the gels. In each case, to obtain the extracted protein, 1 g ground seeds was extracted with 8 mg of sodium myristate in 5 ml distilled water. With the exception of the initial redox state determination of the proteins, samples were extracted for 2 hr at 22° C. and then centrifuged 20 min at 16,000 rpm prior to the addition of the mBBr. With the initial redox state determination, the mBBr was added under a nitrogen atmosphere along with the myristate followed by extraction.

Separate SDSS-polyacrylamide electrophoretic gels of the reduction studies of myristate-extracted proteins from flour of oat, triticale, rye, barley and teff were prepared. A gel showing the extent of thioredoxin linked buffer and ethanol-extracted proteins for teff was also prepared. In all of the oat, triticale, rye, barley, teff/myristate extractions studies, the flour was first extracted with buffer, 50 mM Tris-HCl, pH 7.5 for 20 min and then with 70% ethanol for 2 hr. In addition, gels were prepared for the myristate-extracted proteins from corn, sorghum and rice. With corn, sorghum and rice, the ground seeds were extracted only with myristate. Therefore, with corn, sorghum and rice, the myristate extract represents total protein, whereas with oat, triticale, rye, barley and teff, the myristate extract represents only the glutenin-equivalent fractions since these flours had been previously extracted with buffer and ethanol. The results, depicted in the gels, show that the NTS is most effective, as compared to GSH or GSH/GR/NADPH, with myristate-extracted (glutenin-equivalent) proteins from oat, triticale, rye, barley and teff. The NTS is also most effective with the total proteins from rice. Reduced glutathione is more effective with the total proteins from corn and sorghum.

Conclusions from the Corn, Sorghum and Rice

In the first gel relating to the effect of NTS vs. glutathione reductase on the reduction status of the myristate-extracted proteins, in treatment (1), extraction with myristate in the presence of mBBr was carried out under a nitrogen atmosphere; in treatment (2), to the myristate extracted proteins mBBr was added without prior reduction of the proteins; in treatment (3), the myristate extracted proteins were reduced by the NADP/thioredoxin system (NTS); in treatment (4) the myristate extracted proteins were reduced by NADPH, glutathione and glutathione reductase. In the second gel relating to the in vivo reduction status and thioredoxin linked in vitro reduction of the myristate-extracted proteins, treatment (1) is like treatment (2) in the first gel; in treatment (2) the seeds were extracted with myristate in the presence of mBBr under nitrogen; in treatment (3), seeds were extracted with myristate and reduced by the NTS and then mBBr was added; and in treatment (4) conditions as in (3) except that proteins were reduced by DTT. Treatment (1) in the first gel and treatment (2) in the second gel showed the initial redox state of the proteins in the grains. For all three cereals, the proteins in the seed were highly reduced. If extracted in air, the proteins became oxidized especially the sorghum and rice. The oxidized proteins can be re-reduced, maximally with NTS in all cases. With rice, the reduction was relatively specific for thioredoxin; with corn, glutathione is as effective as thioredoxin and with sorghum glutathione is slightly more effective than thioredoxin. Dithiothretol showed varying effectiveness as a reductant. These experiments demonstrated that the storage proteins of these cereals are less specific than in the case of wheat and suggest that thioredoxin should be tested both in the presence and absence of glutathione when attempting to construct a dough network.

Gels were also prepared resulting from the reduction studies of wheat glutenins and gliadins, respectively, by a yeast NADP/thioredoxin system. The glutenins were obtained by using 50 ml of 0.1 M acetic acid for every 10 gm of flour and extracting for 2 hr. The gliadins were obtained by using 50 ml of 70% ethanol for every 10 gm of flour and extracting for 2 hr. The gels showed that the yeast system is highly active in reducing the two major groups of wheat storage proteins.

Gels for the reduction of ethanol-extracted proteins from flour of triticale, rye, oat and barley, respectively, were also prepared. The results showed that the NTS is most effective with the ethanol-extracted proteins from triticale, rye and oat. The ethanol-extracted barley proteins were reduced in the control and thioredoxin or glutathione had little effect.

EXAMPLE 19

Effect of Thioredoxin-linked Reduction on the Activity and Stability of the Kunitz and Bowman-Birk Soybean Trypsin Inhibitor Proteins Materials and Methods Plant materials Durum wheat (*Triticum durum*, Desf. cv. Monroe) was a kind gift of Dr. K. Kahn. Wheat germ was obtained from Sigma Chemical Co. (St. Louis, Mo.).

Chemicals and Enzymes

Reagents for sodium dodecyl sulfate-polyacrylamide gel electrophoresis (SDS-PAGE) were obtained from Bio-Rad Laboratories (Richmond, Calif.), and DTT was from Boehringer Mannheim Biochemicals (Indianapolis, Ind.). L-1-Tosylamide-2-phenylethyl chloromethyl ketone (TPCK)-treated trypsin (type XIII, T8640), subtilisin (type VIII: bacterial subtilisin Carbsberg, P5380), KTI (T9003), BBTI (T9777), azocasein, and other chemicals were purchased from Sigma Chemical Co. (St. Louis, Mo.). *E. coli* thioredoxin and NTR were isolated from cells transformed to overexpress each protein. The thioredoxin strain containing the recombinant plasmid, pFPI, was kindly provided by Dr. J.-P. Jacquot (de La Motte-Guery et al., 1991). The NTR strain containing the recombinant plasmid, pPMR21, was kindly provided by Drs. Marjorie Russel and Peter Model (Russel and Model, 1988). The isolation procedures used for these proteins were as described in those studies with the following changes: cells were broken in a Ribi cell fractionator at 25,000 psi and NTR was purified as described by Florencio et al. (1988) without the red agarose step. The *E. coli* thioredoxin and NTR were, respectively, 100% and 90% pure as determined by SDS-polyacrylamide gel electrophoresis. Wheat thioredoxin h was purified as previously described (Johnson et al., 1987).

Germination of Wheat Seeds

Wheat seeds were sterilized by steeping in 50% (v/v) of Generic Bleach for 1 h at room temperature, followed by a thorough wash with distilled water. The sterilized seeds were placed in a plastic Petri dish on two layers of Whatman filter paper moistened with distilled water containing 100 μg/ml of chloramphenicol. Germination was continued at room temperature in a dark chamber for up to 5 days.

Preparation of Wheat Proteases

The endosperm (10–15 g fresh weight) isolated from 5-day germinated wheat seeds by excising the roots and shoots was extracted for 30 minutes at 4° C. with 5 volumes of 200 mM sodium acetate, pH 4.6, containing 10 mM β-mercaptoenthanol. The homogenate was centrifuged for 20 minutes at 48,000 g, 4° C. The pellet was discarded and the supernatant fluid was fractionated with 30–70% ammonium sulfate. This fraction, which represented the protease preparation, was resuspended in a minimum volume of 20 mM sodium acetate, pH 4.6, containing 10 mM β-mercaptoenthanol, and dialyzed against this buffer overnight at 4° C. When assayed with azocasein as substrate, the protease preparation had an optimal pH of about 4.6 and was stable for at least one week at 4° C.

Reduction and Proteolytic Susceptibility of Trypsin Inhibitors

Unless indicated, the reduction of the trypsin inhibitors (0.4 mg/ml) was carried out in 0.1 ml of 20 mM sodium phosphate buffer, pH 7.9 containing 10 mM EDTA at 30° C. for 2 hours. The concentrations of thioredoxin, NTR, and NADPH were 0.024 mg/ml, 0.02 mg/ml, and 0.25 mM, respectively. With DTT as reductant, EDTA and components of the NADP/thioredoxin system were omitted. Following reduction, aliquots of the inhibitor mixture were withdrawn either for determination of trypsin inhibitory activity or proteolytic susceptibility. In the subtilisin tests, the inhibitor mixture (50 µl) was directly mixed with subtilisin and incubated at room temperature for 1 hour. With the wheat protease preparation, the pH of the inhibitor mixture (50 µl) was first adjusted to 4.7 by mixing with 35 µl of 200 mM sodium acetate, pH 4.6; 10 µl of the wheat protease preparation was then added and incubation was continued for 2 hours at 37° C. To stop digestion with subtilisin, 2 µl of 100 mM phenylmethylsulfonyl fluoride (PMSF) and 10 µl of 10% SDS were added to the digestion mixture. With the plant protease preparation, digestion was stopped by adding an equal volume of SDS sample buffer [0.125 M Tris-HCl, pH 6.8, 4% (w/v) SDS, 20% (v/v) glycerol, 10% (v/v) β-mercaptoethanol, and 0.02% (w/v) bromophenol blue]. Proteolytic products were analyzed by electrophoresis with 12% or 16% SDS polyacrylamide slab gels (Laemmli, 1970). The dried slab gels were scanned with a laser densitometer (Pharmacia-LKB UltraScan XL) and the peak area of the KTI or BBTI protein band was obtained by integration with a Pharmacia GelScan XL software program.

Assays

Thioredoxin and NTR were assayed as previously described by Florencio et al. (1988). Trypsin activity was measured in 50 mM Tris-HCl, pH 7.9, by following the increase in absorbance at 253 nm with N-benzoyl-L-arginine ethyl ester as substrate (Mundy et al., 1984) or by the release of azo dye into the trichloroacetic acid (TCA)-soluble fraction from azocasein substrate (see below). For trypsin inhibition assays, trypsin (5 to 10 µg) was preincubated with appropriate amounts of KTI or BBTI for 5 minutes at room temperature in 50 mM Tris-HCl, pH 7.9 and proteolytic activity was then determined. While the two substrates yielded similar data, results are presented with only one substrate.

Wheat protease activity was measured by following the release of azo dye into TCA solution from azocasein substrate at pH 4.7. Fifty µl of wheat protease in a solution of 20 mM sodium acetate, pH 4.6, and 10 mM β-mercaptoethanol were added to 50 µl of 200 mM sodium acetate, pH 4.6, and 100 µl of 2% azocasein (in 20 mM sodium phosphate, pH 7.0). Following 1-hour incubation at 37° C., 1 ml of 10% TCA was added and the mixture was allowed to stand for 10 minutes at room temperature. After centrifugation for 5 minutes in a microfuge (8000 g), 1 ml of the supernatant solution was withdrawn and mixed with 1 ml of 1 N NaOH. The absorbance was read at 440 nm. Protein concentration was determined with Bio-Rad reagent using bovine serum albumin as a standard (Bradford, 1976).

Results

Trypsin Inhibitory Activity

The 20 kDa Kunitz and 8 kDa Bowman-Birk trypsin inhibitors of soybean contain 2 and 7 disulfide groups, respectively (Birk, 1976; Wilson, 1988). Although their physiological functions have not been established, the two types of inhibitors have been extensively investigated owing to their wide distribution in legume seeds and their potential to cause nutritional disorders, e.g., hypertrophy and associated malfunctions of the pancreas. As shown in Tables I and II and described in previous Examples, KTI and BBTI are reduced specifically by the NADP/thioredoxin system from either E. coli or plants. The reduced forms of glutathione and glutaredoxin (a thiol protein capable of replacing thioredoxin in certain animal and bacterial systems, but not known to occur in plants (Holmgren, 1985)) were without effect.

To determine the consequence of reduction by thioredoxin, the trypsin inhibitory activity of the oxidized and reduced forms of KTI and BBTI was compared. As shown in Table XI, preincubation with the NADP/thioredoxin system (NTS) for 2 hours at 30° C. resulted in a substantial loss of trypsin inhibitory activity (i.e., there was an increase in trypsin activity relative to the uninhibited control). More specifically, the NADP/thioredoxin system effected a 3- and 6-fold increase in trypsin activity for KTI and BBTI, respectively. Similar results were obtained with DTT, a nonphysiological substitute for thioredoxin, and with thioredoxin reduced by lipoic acid, a naturally occurring dithiol. Extended incubation with DTT alone (overnight at room temperature) led to complete or almost complete inactivation of both inhibitors (data not shown). Unlike DTT, lipoic acid did not reduce (inactivate) KTI and BBTI significantly in the absence of thioredoxin.

TABLE XI

Changes in the Ability of Soybean Trypsin Inhibitors to Inhibit Trypsin Following Reduction by the NADP/Thioredoxin System, DTT or Reduced Lipoic Acid

| Treatment | Relative Trypsin Activity* | |
|---|---|---|
| | KTI | BBTI |
| No inhibitor | 100 | 100 |
| Inhibitor | | |
| Oxidized | 17.0 | 11.5 |
| Reduced by NTS[1] | 55.6 | 70.6 |
| Reduced by DTT[2] | 68.6 | 88.9 |
| Reduced by LA/Trx h[3] | 40.5 | 87.8 |

*The specific activity of the uninhibited control trypsin was 0.018 $\Delta A_{253nm}$/µg/min using N-benzoyl-L-arginine ethyl ester as substrate.
[1]Reduction by E. coli NTS (NADP/thioredoxin system) was conducted at 30° C. for 2 hours.
[2]Reduction by DTT (1 mM) was conducted at 30° C. for 1 hour.
[3]Reduction by lipoic acid (LA, 0.4 mM) and wheat thioredoxin h (Trx h) was conducted at 30° C. for 1 hour. In the presence of lipoic acid alone (0.4 mM), trypsin activity was 20.0% for KTI and 12.5% for BBTI.

Friedman and colleagues observed that heating soybean flour in the presence of sulfur reductants (sodium sulfite, N-acetyl-L-cysteine, reduced glutathione, or L-cysteine) inactivated trypsin inhibitors, presumably as a result of the reduction or interchange of disulfide groups with other proteins in soy flour (Friedman and Gumbmann, 1986; Friedman et al., 1982, 1984). Inactivation of the trypsin inhibitors by these reductants improved the digestibility and nutritive value of flours in tested rats (Friedman and Gumbman, 1986). Taken together with these earlier observations, the present findings demonstrate that disulfide bonds of both KTI and BBTI targeted by thioredoxin are important to maintenance of trypsin inhibitory activity.

Heat Stability

Protease inhibitor proteins are typically stable to inactivation treatments such as heat. This stability is attributed, at least in part, to the cross-linking of disulfide bonds (Birk, 1976; Ryan, 1981). It is known that breaking the disulfide bonds by reduction decreases heat stability (Friedman et al., 1982). The question arises as to whether reduction by thioredoxin yields similar results.

The results as shown in TABLE XII provide a positive answer to this question. When heated at 80° C. for 15 minutes, the thioredoxin-reduced form of KTI completely lost its ability to inhibit trypsin, whereas its oxidized counterpart retained about half of the original activity (Table XII). Oxidized BBTI was even more stable, retaining the bulk of its trypsin inhibitory activity after heating at 100° C. for 25 minutes. Nonetheless, as with KTI, the reduced form of BBTI was fully inactivated by heat (Table XII). These results are consistent with prior observations (i) that KTI and BBTI show increased sensitivity to heat on reduction; and (ii) that pure BBTI in solution is more heat-stable than pure KTI in solution. The reverse is true for flour (i.e., KTI is more heat-stable than BBTI (Friedman et al., 1982 and 1991; and DiPietro and Liener, 1989)).

TABLE XII

Heat Stability of the Kunitz and Bowman-Birk Trypsin Inhibitors: Oxidized and Following Reduction by the *E. coli* NADP/thioredoxin System

| Treatment | Relative Trypsin Activity* | |
|---|---|---|
| | KTI | BBTI |
| No inhibitor | 100 | 100 |
| Inhibitor, unheated | | |
| Oxidized | 26.6 | 9.4 |
| Reduced | 76.4 | 82.4 |
| Inhibitor, heated 15 min at 80° C. | | |
| Oxidized | 52.3 | nd[1] |
| Reduced | 98.7 | nd |
| Inhibitor, heated 25 min at 100° C. | | |
| Oxidized | nd | 17.2 |
| Reduced | nd | 98.4 |

*The specific activity of trypsin was 0.319 $\Delta A_{440nm}$/mg/min using azocasein as substrate. The temperatures used for inactivation were determined in initial experiments designed to show the heat stability of the trypsin inhibitors under our conditions.
[1]nd: not determined.

Protease Susceptibility

To test whether the reduced forms of KTI and BBTI show decreased stability to proteases other than trypsin, both the reduced and oxidized forms of KTI and BBTI were incubated with a wheat protease preparation or with subtilisin and the proteolytic products were analyzed by SDS-PAGE. The extent of proteolysis was determined by measuring the abundance of intact protein on SDS gels by laser densitometer. When tested with a protease preparation from 5-day germinated wheat seeds, the oxidized form of the Kunitz inhibitor was almost completely resistant to digestion whereas the thioredoxin-reduced form was susceptible to protease. As shown in Table XIII, about 80% of KTI was degraded in a reaction that depended on all components of the NADP/thioredoxin system (NTS). BBTI showed the same pattern except that the oxidized protein showed greater proteolytic susceptibility relative to KTI. Similar effects were observed with both inhibitors when the plant protease preparation was replaced by subtilisin (data not shown). The nature of the prdteolytic reaction was not investigated, but it is noted that peptide products were not detected on SDS gels.

TABLE XIII

Effect of Thioredoxin-linked Reduction on the Susceptibility of Kunitz and Bowman-Birk Trypsin Inhibitors to Proteolysis by a Plant Protease Preparation[1]

| Treatment | Relative Abundance[2] | |
|---|---|---|
| | KTI | BBTI |
| No protease | 100 | 100 |
| Protease | | |
| No reduction system | 97.9 | 67.2 |
| *E. coli* NTS[3] | 22.1 | 16.0 |
| NTS minus thioredoxin | 90.2 | nd[4] |
| NTS minus NADPH | 97.7 | nd |
| NTS minus NTR | 97.9 | nd |

[1]Following reduction by *E. coli* thioredoxin system at 30° C. for 2 hours, pH was adjusted to 4.7 by addition of 200 mM sodium acetate, pH 4.6. Wheat protease preparation was then added and incubated at 37° C. for 2 hours, followed by SDS-PAGE analyses.
[2]Determined by laser densitometer.
[3]NTS: NADP/thioredoxin system.
[4]nd: not determined.

This Example shows that reduction by thioredoxin, or dithiothreitol (DTT), leads to inactivation of both proteins and to an increase in their heat and protease susceptibility. The results indicate that thioredoxin-linked reduction of the inhibitor proteins is relevant both to their industrial processing and to seed germination.

These results confirm the conclusion that disulfide bonds are essential for the trypsin inhibitory activity of KTI and BBTI (Birk, 1985; Friedman and Gumbmann, 1986; Friedman et al., 1982,1984). These studies also show that reduction (inactivation) can take place under physiological conditions (i.e., at low temperature with NADPH-reduced thioredoxin). The ability to inactivate the trypsin inhibitors at lower temperatures provides a potential method for full inactivation of both trypsin inhibitors, thereby improving the quality of soybean products and saving energy. The need for a method for the complete inactivation of KIT is significant since 20% of its activity is consistently retained in soy flour under conditions in which BBTI is fully inactivated (Friedman et al., 1991).

The present results also add new information on the protease susceptibility of KTI and BBTI. Their increase in protease susceptibility following reduction suggests that, if exposed to the protease inhibitors during seed germination, the NADP/thioredoxin system could serve as a mechanism by which the inhibitor proteins are modified (inactivated) and eventually degraded (Baumgartner and Chrispeels, 1976; Chrispeels and Baumgartner, 1978; Orf et al., 1977;

Wilson, 1988; Yoshikawa et al., 1979). As stated previously, there is evidence that the NADP-thioredoxin system plays a similar role in mobilizing proteins during the germination of wheat seeds.

EXAMPLE 20

Reduction of Castor Seed 2S Albumin Protein by Thioredoxin

The results of the following study of sulfhydryl agents to reduce the 2S protein from castor seed (Sharief and Li, 1982; Youle and Huang, 1978) shows that thioredoxin actively reduces intramolecular disulfides of the 2S large subunit but not the intermolecular disulfides joining the two subunits.

Materials and Methods
Materials

Seeds of castor (*Ricinus communes* L. var *Hale*) were obtained from Bothwell Enterprises, Plainview, Tex.). Biochemicals were obtained from Sigma Chemical Co. (St. Louis, Mo.). *E. coli* thioredoxin and NTR were isolated from cells transformed to overexpress each protein. The thioredoxin strain containing the recombinant plasmid pFPI, was kindly provided by Dr. J.-P. Jacquot (de La Mott-Guery et al. 1991). The strain containing the recombinant plasmid, pPMR21, was kindly provided by Drs. Marjorie Russel and Peter Model (Russel and Model, 1988). Thioredoxin and NTR were purified by the respective procedures of de La Mott-Guery et al. (1991) and Florencio et al. (1988). Reagents for SDS-polyacrylamide gel electrophoresis were purchased from Bio-Rad Laboratories (Richmond, Calif.). Monobromobimane (mBBr) or Thiolite was obtained from Calbiochem (San Diego, Calif.). Other chemicals were obtained from commercial sources and were of the highest quality available. NADP-malate dehydrogenase and fructose-1,6-bisphosphatase were purified from leaves of corn (Jacquot et al. 1981) and spinach (Nishizawa et al. 1982), respectively. Thioredoxin h was isolated from wheat seeds by following the procedure devised for the spinach protein (Florencio et al. 1988). Glutathione reductase was prepared from spinach leaves (Florencio et al. 1988).
Isolation of Protein Bodies Protein bodies were isolated by a nonaqueous method (Yatsu and Jacks, 1968). Shelled dry castor seeds, 15 g, were blended with 40 ml of glycerol for 30 sec in a Waring blender. The mixture was filtered through four layers of nylon cloth. The crude extract was centrifuged at 272×g for 5 min in a Beckman J2-21M centrifuge using a JS-20 rotor. After centrifugation, the supernatant fraction was collected and centrifuged 20 min at 41,400×g. The pellet, containing the protein bodies, was resuspended in 10 ml glycerol and centrifuged as before (41,400×g for 20 min) collecting the pellet. This washing step was repeated twice. The soluble ("matrix") fraction was obtained by extracting the pellet with 3 ml of 100 mM Tris-HCl buffer (pH 8.5). The remaining insoluble ("crystalloid") fraction, collected by centrifugation as before, was extracted with 3 ml of 6M urea in 100 mM Tris-HCl buffer (pH 8.5).
2S Protein Purification Procedure The 2S protein was prepared by a modification of the method of Tully and Beevers (1976). The matrix protein fraction was applied to a DEAE-cellulose (DE-52) column equilibrated with 5 mM Tris-HCl buffer, pH 8.5 (Buffer A) and eluted with a 0 to 300 mM NaCl gradient in buffer A. Fractions containing the 2S protein were pooled and concentrated by freeze drying. The concentrated fraction was applied to a Pharmacia FPLC Superose-12 (HR 10/30) column equilibrated with buffer A containing 150 mM NaCl. The fraction containing 2S protein from the Superose-12 column was applied to an FPLC Mono Q HR 515 column equilibrated with buffer A. The column was eluted sequentially with 3 ml of buffer A, 20 ml of a linear gradient of 0 to 300 mM NaCl in buffer A and finally with buffer A containing 1 M NaCl. The 2S protein purified by this method was free of contaminants in SDS polyacrylamide gels stained with Coomassie blue (Kobrehel et al., 1991).
Analytical Methods Reduction of proteins was monitored by the monobromobimnane (mBBr)/SDS polyacrylamide gel electrophoresis procedure of Crawford et al. (1989). Labeled proteins were quantified as described previously in the "Reduction of Cereal Proteins, Materials and Methods" section. Protein was determined by the method of Bradford (1976).
Enzyme Assays/Reduction Experiments The Wada et al., 1981 protocol was used for assaying NADP-malate dehydrogenase and fructose 1,6 bisphosphatase in the presence of thioredoxin and 2S protein. Assays were conducted under conditions in which the amount of added thioredoxin was sufficient to reduce the castor 2S protein but insufficient to activate the target enzyme appreciably. All assays were at 25° C. Unless otherwise indicated, the thioredoxin and NTR used were from *E. coli*. The 2S protein was monitored during purification by mBBr/SDS-polyacrylamide gel electrophoresis following its reduction by dithiothreitol and *E. coli* thioredoxin (Crawford et al., 1989; Kobrehel et al., 1991).

The reduction of the matrix and crystalloid proteins from castor seed were determined by the mBBr/SDS-polyacrylamide gel electrophoresis procedure. The lanes for the gels (not shown) were as follows, 1 and 7, Control: no addition; 2 and 8, GSH/GR/NADPH: reduced glutathione, glutathione reductase (from spinach leaves) and NADPH; 3 and 9, NGS: NADPH, reduced glutathione, glutathione reductase (from spinach leaves) and glutaredoxin from *E. coli*; 4 and 10, NTS: NADPH, NTR, and thioredoxin (both proteins from *E. coli*); 5 and 11, NADPH; 6 and 12, NADPH and *E. coli* NTR. Reactions were carried out in 100 mM Tris-HCl buffer, pH 7.8. As indicated, 0.7 $\mu$g NTR and 1 $\mu$g thioredoxin were added to 70 $\mu$l of this buffer containing 1 mM NADPH and target protein: 8 $\mu$g matrix protein for treatments 1–6 and 10 $\mu$g crystalloid protein for treatments 7–12. Assays with glutathione were performed similarly, but at a final concentration of 2 mM, 1.4 $\mu$g glutathione reductase, 1 $\mu$g glutaredoxin, and 1.5 mM NADPH. Reaction time was 20 min.

The mBBr/SDS-Page technique was also used to determine the specificity of thioredoxin for reducing the disulfide bonds of castor seed 2S protein. The lanes for the gel (not shown) were as follows, (1) Control (no addition); (2) Control+NTS (same conditions as with the matrix and crystalloid proteins); (3) Control (heated 3 min at 100° C.); (4) Control+2 mM DTT (heated 3 min at 100° C.). The samples containing 5 $\mu$g 2S protein and the indicated additions were incubated for 20 min in 30 mM Tris-HCl (pH 7.8). mBBr, 80 nmol, was then added and the reaction continued for another 15 min prior to analysis by the mBBr/SDS polyacrylamide gel electrophoresis procedure.

Results

The castor storage proteins, which are retained within a protein body during seed maturation, can be separated into two fractions on the basis of their solubility. The more soluble proteins are housed in the protein body outer section ("matrix") and the less soluble in the inner ("crystalloid"). In the current study, the matrix and crystalloid components were isolated to determine their ability to undergo reduction by cellular thiols, viz., glutathione, glutaredoxin and thioredoxin. Glutaredoxin, a 12 kDa protein with a catalytically active thiol group, can replace thioredoxin in certain enzymic reactions of bacteria and animals (Holmgren et al. 1985) but is not known to occur in plants.

The results showed that, while a number of storage proteins of castor seed were reduced by the thiols tested, only a low molecular weight protein, corresponding to the large subunit of the 2S protein of the matrix, showed strict specificity for thioredoxin. Certain higher molecular weight proteins of the crystalloid fraction underwent reduction, but in those cases there was little difference between glutaredoxin and thioredoxin. The castor seed 2S large subunit thus appeared to resemble cystinecontaig proteins previously discussed in undergoing thioredoxin-specific reduction. These experiments were designed to confirm this specificity and to elucidate certain properties of the reduced protein. As expected, owing to lack of disulfide groups, the 2S small subunit showed essentially no reaction with mBBr with any of the reductants tested.

When its fluorescent band was monitored by laser densitometry, the reduction of the castor seed 2S large subunit was found to depend on all Ao components of the NADP/thioredoxin system (NADPH, NTR and thioredoxin) (Table XIV). As for other thioredoxin-linked proteins (including chloroplast enzymes), the thioredoxin active in reduction of the 2S large subunit could be reduced either chemically with dithiothreitol (DTT) or enzymatically with NADPH and NTR. The extent of reduction by the NADP thioredoxin system, DTT alone, and DTT+thioredoxin was 84%, 67% and 90%, respectively, after 20 min at 25° C. Similar, though generally extensive reduction was observed with the disulfide proteins discussed above (Johnson et al. 1987). As with the other seed proteins, native wheat thioredoxin h and *E. coli* thioredoxins could be used interchangeably in the reduction of the 2S protein by DTT (data not shown).

TABLE XIV

Extent of reduction of the castor castor seed 2S protein by different sulfhydryl reductants. Reaction conditions as with the matrix and crytalloid protein determination. A reduction of 100% corresponds to that obtained when the 2S protein was heated for 3 min in the presence of 2% SDS and 2.5% β-mercaptoethanol. NTS: NADPH, NTR, and thioredoxin (both proteins from *E. coli*); GSH/GR/NADPH: reduced glutathione, glutathione reductase (from spinach leaves) and NADPH; NGS: NADPH, reduced glutathione, glutathione reductase (from spinach leaves) and glutaredoxin (from *E. coli*).

| Treatment | Relative Reduction (%) |
|---|---|
| Control | 0 |
| NADP/thioredoxin system, complete | 84 |
| NADP minus thioredoxin | 0 |
| NADP minus NADPH | 0 |
| NADP minus NTR | 0 |
| Reduced glutathione | 0 |
| NADP/glutaredoxin system, complete | 0 |
| DTT | 67 |
| DTT + thioredoxin | 90 |

The capability of thioredoxin to reduce the castor seed 2S protein was also evident in enzyme activation assays. Here, the protein targeted by thioredoxin (in this case 2S) is used to activate a thioredoxin-linked enzyme of chloroplasts, NADP-malate dehydrogenase or fructose 1,6-bisphosphatase. As with most of the proteins examined so far, the 2S protein more effectively activated NADP-malate dehydrogenase and showed little activity with the fructose bisphosphatase (2.6 vs. 0.0 nmoles/min/mg protein).

The castor seed 2S protein contains inter- as well as intramolecular disulfides. The 2S protein thus provides an opportunity to determine the specificity of thioredoxin for these two types of bonds. To this end, the castor seed 2S protein was reduced (i) enzymically with the NADP/thioredoxin system at room temperature, and (ii) chemically with DTT at 100° C. Following reaction with mBBr the reduced proteins were analyzed by SDS-polyacrylamide gel electrophoresis carried out without additional sulfhydryl agent. The results indicate that while thioredoxin actively reduced intramolecular disulfides, it was much less effective with intermolecular disulfides.

The present results extend the role of thioredoxin to the reduction of the 2S protein of castor seed, an oil producing plant. Thioredoxin specifically reduced the intramolecular disulfides of the large subunit of the 2S protein and showed little activity for the intermolecular disulfides joining the large and small subunits. Based on the results with the trypsin inhibitors of soybean, it is clear that reduction of intramolecular disulfides by thioredoxin markedly increases the susceptibility of disulfide proteins to proteolysis (Jiao et al. 1992a). It, however, remains to be seen whether reduction of the 2S protein takes place prior to its proteolytic degradation (Youle and Huang, 1978) as appears to be the case for the major storage proteins of wheat. A related question raised by this work is whether the 2S protein of castor, as well as other oil producing plants such as brazil nut (Altenbach et al., 1987; Ampe et al., 1986), has a function in addition to that of a storage protein.

EXAMPLE 21

Thioredoxin-Dependent Deinhibition of Pullulanase of Cereals by Inactivation of a Specific Inhibitor Protein Assay or Pullulanase 1. Standard Curve of Maltotriose A series of concentrations of maltotriose (0 to 2 mg) in 0.1 to 0.2 ml water or buffer were made in microfuge tubes. To this was added 0.2 ml of dinitrosalicylic acid (DA) reagent (mix 1 g of DA, 30 g of sodium potassium tartrate, and 20 ml of 2N NaOH with water to final volume of 100 ml). The reagents were dissolved in a warm water bath. The mixture was heated at 100° C. for 5 min and cooled down in a water bath (room temperature). Each sample was transferred to a glass tube that contained 2 ml of water. Read $A_{493}$ vs water. $\Delta A_{493}$ [$A_{493}$ of sample containing maltotriose was subtracted from $A_{493}$ of the blank (no maltotriose)] was plotted against maltotriose concentrations.

2. Pullulanase Activity Assay

Pullulanase activity is measured as the release of reducing sugar from the substrate pullulan. Typically 10–100 μl of pullulanase sample (in 20 mM Tris-HCl, pH 7.5, or in 5–20 acetate-NA, pH 4.6) was mixed with 25–100 μl of 200 mM Acetate-NA, pH 5.5 (this buffer serves to bring final pH of the assay to 5.5) and 10–20 μl of 2% (w/v) pullulan. The mixture was incubated at 37° C. for 30 to 120 min, depending on the activity of pullulanase. The reaction was stopped by adding 200 μl of DA reagent. Reducing sugar was then determined as above.

Note

1. When a crude extract of pullulanase obtained by the dialysis of crude extracts or pullulanase obtained from a dialyzed 30–60% ammonium sulfate fraction is used as a pullulanase source, it must be thoroughly dialysed before assay because there are reduced sugars in the crude extract. In other words the backroun of crude pullulanase samples from dialysed crude extracts or a dialysed 30–60% ammonium sulfate fraction is very high. In this case, the blank is made as follows: 200 μl of DA reagent are added first, followed by the addition of enzyme sample, pullulan and buffer.

2. When final concentrations of DTT (or β-mercaptoethanol (MET) or GSH) are higher than 2 mM in the assay mixture, the $OD_{493}$ values will be greater than those of the minus-DTT (MET, GSH) samples. DTT (MET, GSH) should be added to the blank, samples without DTT during assay at the end of the reaction. Care should be taken to make sure the final concentration of DTT in the assay mixture is below 2 mM.

Purification of Pullulanase Inhibitor Extraction and Ammonium Sulfate Fractionation 200 g of barley malt was ground to fine powder with an electric coffee grinder and extracted with 600 ml of 5% (w/v) NaCl for 3 h at 30° C. Following centrifugation at 30,000 g and at 4° C. for 25 min, the supernatant was fractionated by precipitation with solid ammonium sulfate. Proteins precipitated between 30% and 60% saturated ammonium sulfate were dissolved in a minimum volume of 20 mM Tris HCl, pH 7.5, and dialyzed against this buffer at 4° C. overnight.

DE52 Chromatography

The dialyzed sample was centrifuged to remove insoluble materials and the supernatant adjusted to pH 4.6 with 2N formic acid. After pelleting the acid-denatured protein, the supernatant was readjusted to pH 7.5 with $NH_4OH$ and loaded onto a DE52 column (2.5×26 cm) equilibrated with 20 mM Tris-HCl, pH 7.5. Following wash with 80 ml of the above buffer, the column was eluted with a linear 0–500 mM Tris-HCl, pH 7.5. Fractions of By 6.7 ml were collected. Pullulanase was eluted at about 325 mM NaCl and its inhibitor came off at about 100 mM NaCl. Pullulanase was further purified through CM32 (20 mM sodium acetate, pH 4.6) and Sephacryl-200 HR (30 mM Tris-HCl, pH 7.5, containing 200 mM NaCl and 1 mM EDTA) chromatography. Pullulanase inhibitor protein was purified as described below.

CM32 Chromatography

The pullulanase inhibitor sample (about 90 ml) from the DE52 step was placed in a 150-ml flask and incubated at 70° C. water-bath for 20 min. Following centrifugation, the clarified sample was then adjusted to pH 4.6 with 2N formic acid and dialyzed against 20 mM sodium acetate, pH 4.6. The precipitate formed during dialysis was removed by centrifugation and the supernatant was chromatographed on a CM32 column (2.5×6 cm) equilibrated with 20 mM sodium acetate, pH 4.6. Proteins were eluted with a linear 0–0.4 M NaCl in 200 ml of 20 mM sodium acetate, pH 4.6. Fractions (5.0 ml/fraction) containing pullulanase inhibitory activity were pooled, dialyzed, and rechromatographed on a CM32 column (2.5×6 cm) with a linear 0.2–1 M NaCl gradient in 200 ml of 20 mM sodium acetate, pH 4.0.

Sephadex G-75 Filtration

Pullulanase inhibitor fractions from the second CM32 chromatography step were concentrated in a dialysis bag against solid sucrose and then separated by a Sephadex G-75 column (2.5×85 cm) equilibrated with 30 mM Tris-HCl, pH 7.5, containing 200 mM NaCl and 1 mM EDTA. Fractions (3.6 ml/fraction) showing pullulanase inhibitory activity were pooled, concentrated by dialysis against solid sucrose, and then dialysed against 10 mM Tris-HCl,pH 7.5.

Identification and Purification of Pullulanase Inhibitor

During gemination, starch is converted to glucose by α, β-amylases, and pullulanase (also called debranching enzyme, Renzyme). While extensive studies have been conducted for the regulation of amylases, little is known about the regulation of pullulanase in seeds. Yamada (Yamada, J. (1981) *Carbohydrate Research* 90:153–157) reported that incubation of cereal flours with reductants (e.g., DTT) or proteases (e.g., trypsin) led to an activation of pullulanase activity, suggesting that reduction or proteolysis might be a mechanism by which pullulanase is activated during germination. Like in rice flour, pullulanase extracts from germinated wheat seeds or from barley malt showed lower activity, and were activated 3 to 5-fold by preincubation with DTT for 20 to 30 min. However, following purification of the crude extract (a dialysate of 30–60% ammonium sulfate fraction) by anion or cation exchange chromatography, the total pullulanase activity increased 2 to 3-fold over that of the sample applied to the column when assayed without preincubation with DTT, and DTT has no or little effect on pullulanase.

One possibility was that pullulanase might be activated by proteolysis during the process of purification, since germinated wheat seeds or barley malt show high protease activity. If this was the case, addition of protease inhibitor cocktail would prevent pullulanase activation during purification. In contrast to this point, many experiments with protease inhibitors failed to prove this. Another possibility was that there is an inhibitor that is precipitated by ammonium sulfate and inhibits pullulanase. The role of DTT is to reduce and thus inactivate this protein inhibitor, leading to activation of pullulanase. Along this line, the 30–60% ammonium sulfate fraction from barley malt was applied to a DE52 column (2.5×26 cm) equilibrated with 20 mM Tris-CHl, pH 7.5. Following elution with a linear salt gradient, "deinhibited" ("activated") pullulanase was identified as a protein peak coming off at about 325 mM NaCl (from fraction numbers 44 to 60). Assay of pullulanase activity in the preincubation mixture consisting of 50 μl of the peak pullulanase activity fraction (fraction number 45) with 50 μl of other protein fracitons indicated that a protein peak that showed pullulanase inhibitory activity was eluted from the DES2 column by about 100 mM NaCl between fraction numbers 8 to 25.

The pullulanase inhibitor sample was further purified by two consecutive cation exchange chromatography steps with CM32 at pH 4.6 and 4.0, and filtration with Sephdex G-75.

Properties of Pullulanase Inhibitor

Preliminary experiments showed that pullulanase inhibitor protein is resistant to treatment of 70° C. for 10 min and pH 4.0. Based on the profile of Sephadex G-75 gel filtration and SDS-PAGE, pullulanase inhibitor has a molecular weight between 8 to 15 kDa±2 kDa. The study further showed that the protein contains thioredoxin-reducible (S—S) bonds.

These studies, as shown in Table XV, found that the ubiquitous dithiol protein, thioredoxin, serves as a specific reductant for a previously unknown disulfide-containing protein that inhibits pullulanase of barley and wheat endosperm.

TABLE XV

Activity Change in Pullulanase Inhibitor Protein
Following Reduction by NADP/Thioredoxin System

| Treatment | Relative Pullulanase Activity |
| --- | --- |
| No inhibitor | 100 |
| Inhibitor | |
| Oxidized | 30.1 |
| Reduced by DTT | 46.1 |
| Reduced by E. coli Trx/DTT | 95.1 |
| Reduced by E. coli NTS | 40.4 |
| Reduced by GSH/NADPH/GR | 33.6 |

Reduction of the inhibitor protein eliminated its ability to inhibit pullulanase, thereby rendering the pullulanase enzyme active. These studies as shown in Table XV illustrate that it is possible to render the pullulanase enzyme active with a physiological system consisting of NADPH, NADP-thioredoxin reductase (NTR) and thioredoxin (the NADP/thioredoxin system) as well as with thioredoxin (Trx) and dithiothreitol. These findings also elucidate how reductive activation of pullulanase takes place (i.e., that a specific (previously unknown) inhibitor is reduced and thereby inactivated, so that the enzyme becomes active). The thioredoxin active in this reaction can be obtained from several sources such as E. coli or seed endosperm (thioredoxin h). The role of thioredoxin in reductively inactivating the inhibitor protein (I) and deinhibiting the pullulanase enzyme (E) is given in Equations 1 and 2.

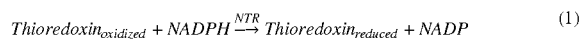
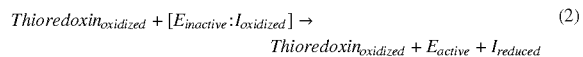

$$Thioredoxin_{oxidized} + NADPH \xrightarrow{NTR} Thioredoxin_{reduced} + NADP \quad (1)$$

$$Thioredoxin_{oxidized} + [E_{inactive} \colon I_{oxidized}] \rightarrow \\ Thioredoxin_{oxidized} + E_{active} + I_{reduced} \quad (2)$$

In summary, the crude endosperm extracts were fractionated by column chromatography procedures. These steps served to separate the protein inhibitor from the pullulanase enzyme. The inhibitor protein was then highly purified by several steps. By use of the mBBr/SDS-PAGE procedure, it was determined that disulfide group(s) of the new protein are specifically reduced by thioredoxin and that the reduced protein loses its ability to inhibit pullulanase. Like certain other disulfide proteins of seeds (e.g., the Kunitz and Bowman-Birk trypsin inhibitors of soybean), the pullulanase inhibitor protein showed the capability to activate chloroplast NADP-malate dehydrogenase. In these experiments, dithiothreitol was used to reduce thioredoxin, which in turn reduced inhibitor and thereby activated the dehydrogenase enzyme.

EXAMPLE 22

Engineering of Yeast Cells to Overexpress Thioredoxin and NADP-Thioredoxin Reductase The two *Saccharomyces cerevisiae* thioredoxin genes (Muller, E. G. D. (1991), *J. Biol. Chem.* 266:9194–9202), TRX1 and TRX2, are cloned in high copy number episomal vectors, an example of which is YEp24, under the control of strong constitutive promoter elements, examples of which are the glycolytic promoters for the glyceraldehyde-3-P dehydrogenase, enolase, or phosphoglycerate kinase genes. Recombinant constructs are assessed for the overexpression of thioredoxin by quantitative Western blotting methods using an antithioredoxin rabbit antiserum (Muller, E. G. D. et al. (1989), *J. Biol. Chem.* 264:4008–4014), to select the optimal combination of thioredoxin genes and promoter elements. The cells with the optimal thioredoxin overexpression system are used as a source of thioredoxin for dough improvement.

The NADP-thioredoxin reductase gene is cloned by preparing an oligonucleotide probe deduced from its amino terminal sequence. The enzyme is prepared from yeast cells by following a modification of the procedure devised for spinach leaves (Florencio, F. J. et al. (1988), *Arch. Biochem. Biophys.* 266:496–507). The amino terminus of the pure reductase enzyme is determined by microsequencing by automated Exman degradation with an Applied Biosystems gas-phase protein sequencer. On the basis of this sequence, and relying on codon usage in yeast, a 20-base 24-bold degenerate DNA probe is prepared. The probe is hybridized to isolated yeast DNA cleaved with EcoRI and PstI by Southern blot analysis. The most actively region is extracted from the agarose gels and introduced into a pUC19 plasmid vector (Szekeres, M. et al. (1991), *J. Bacteriol.* 173:1821–1823). Following transformation, plasmid-containing *E. coli* colonies are screened by colony hybridization using the labeled oligonucleotide probe (Vogeli, G. et al. (1987), *Methods Enymol.* 152:407–415). The clone is identified as carrying the gene for NADP-thioredoxin reductase by sequencing the DNA as given in Szekeres et al. above. Once identified, the NADP-thioredoxin reductase gene is overexpressed in yeast as described above for the TRX1 and TRX2 yeast thioredoxin genes. The yeast cells which overexpress NADP-thioredoxin reductase are used as a source of reductase to improve dough quality.

EXAMPLE 23

Improvement in Dough Quality Using Genetically Engineered Yeast Cells

*Saccharomyces cerevisiae* cells engineered to overexpress the two yeast thioredoxins and the yeast NADP-thioredoxin reductase as set forth in Example 23 are lysed by an established procedure such as sonication and then freeze dried. The dried cells from the cultures overexpressing thioredoxin and NADP-thioredoxin reductase are combined and then used to supplement flour to improve its dough quality. Two-tenths gram of the combined lysed dried cells are added together with about 300 to about 500 nanomoles NADPH to 1 M Tris-HCl buffer, pH 7.9, to give 5.25 ml of 30 mM Tris-HCl. The reaction is carried out in a microfarinograph at 30° C. as described in Example 14. An improvement in dough quality is observed which is similar to the improvement shown in Example 14.

EXAMPLE 24

Improvement of Gluten

The positive effects of the NADP/thioredoxin system on dough quality presents the option of applying this system to flour in the preparation of gluten. The purpose is to alter the yield and the properties of gluten, thereby enhancing its technological value: (1) by obtaining stronger glutens (increased elasticity, improved extensibility); (2) by increasing gluten yield by capturing soluble proteins, reduced by the NADP-thioredoxin system, in the protein network, thereby preventing them from being washed out during the production of gluten. In this procedure (using 10 g flour), 0.2

μg E. coli thioredoxin, 0.1 μg E. coli NADP-thioredoxin reductase and 300 to 500 nanomoles NADPH are added together with 1 M Tris-HCl, pH 7.9, buffer to give 5.25 ml of 30 mM Tris-HCl. The gluten is made at room temperature according to the common lixiviation method. The yield of the gluten is determined by weight and the strength of the gluten is determined by the classical manual stretch method. The gluten product which are obtained by this treatment with the NADP/thioredoxin system is used as an additive in flour or other grain.

EXAMPLE 25

Method of Producing Dough from a Non-wheat or Rye Flour

For this test (using 10 gm of milled flour from corn, rice or sorghum), 0.2 μg E. coli thioredoxin, 0.1 μg E. coli NADP-thioredoxin reductase and 500 nanomoles NADPH are added together with 1 M Tris-HCl, pH 7.9, buffer to give 5.25 ml of 30 mM Tris-HCl. The reaction is carried out by mixing the 10 gm of milled flour with the enzyme system in a micro-farinograph at 30° C. The farinograph measurements show wheat-like dough characteristics by the added NADP-thioredoxin system. In the controls without the enzyme system, no microfarinograph reading is possible because the mixture fails to form a dough. The dough which is formed is persistent and its consistency is maintained throughout the run. The end product is similar to the network formed in dough derived from wheat.

Reduction of Animal Toxins

The invention provides a method for chemically reducing toxicity causing proteins contained in bee, scorpion and snake venome and thereby altering the biological activity of the venoms well as reducing the toxicity of animal toxins specifically snake neurotoxins by means of thiol redox (SH) agents namely a reduced thioredoxin, reduced lipoic acid in the presence of a thioredoxin or DTT. The reduction of the thioredoxin occurs preferably via the NADP-thioredoxin system (NTS). As stated previously, the NTS comprises NADPH, NADP-thioredoxin reductase (NTR) and a thioredoxin.

The term "thiol Redox agent" has been used sometimes in the literature to denote both an agent in the nonreduced state and also in the reduced or sulfhydryl (SH) state. As defined herein the term "thiol redox (SH) agent" means a reduced thiol redox protein or synthetically prepared agent such as DTT.

The reduction of the neurotoxin may take place in a medium that is liquid such as blood, lymph or a buffer, etc. or in a medium that is solid such as cells or other living tissue. As used herein the term "liquid" by itself does not refer to a biological fluid present in an individual.

Presumably the proficiency of the thiol redox (SH) agents to inactivate the venom in vitro and to detoxify the venom in individuals depends upon the ability of the agents of the invention to reduce the intramolecular disulfide bonds in these toxicity causing venom components.

All snake neurotoxins, both presynaptic and postsynaptic can be reduced and at least partially inactivated in vitro by the thiol redox (SH) agents of the invention. Snake neurotoxins inactivated in vitro according to the invention are useful as antigens in the preparation of antivenoms. The neurotoxins are inactivated preferably by incubation with a thiol redox (SH) agent in an appropriate buffer. The preferred buffer is Tris-HCl buffer but other buffers such as phosphate buffer may be used. The preferred thiol redox (SH) agent is a reduced thioredoxin.

Effective amounts for inactivating snake neurotoxins range from about 0.1 μg to 5.0 μg, preferably about 0.5 μg to 1.0 μg, of a reduced thioredoxin; from about 1 nanomole to 20 nanomoles, preferrably from 5 nanomoles to 15 nanomoles, of reduced lipoic acid in the presence of about 1.0 μg of a thioredoxin and from about 10 nanomoles to 200 nanomoles, preferrably 50 nanomoles to 100 nanomoles, of reduced DTT (preferably in the presence of about 1.0 μg of a thioredoxin) for every 10 μg of snake neurotoxin in a volume of 100 μl.

The effective amounts for inactivating a snake neurotoxin using the components in the NADP-thioredoxin system range from about 0.1 μg to 5.0 μg, preferably about 0.5 μg to 1.0 μg, of thioredoxin; from about 0.1 μg to 2.0 μg, preferrably from 0.2 μg to 1.0 μg, of NTR and from about 0.05 micromoles to 0.5 micromoles, preferrably about 0.1 micromoles to 0.25 micromoles, of NADPH for every 10 μg of snake neurotoxin in a volume of 100 μl.

Upon inactivation the buffer containing the inactivated neurotoxin and thiol redox (SH) agent, etc. may be injected into an animal such as a horse to produce an antivenom or prior to injection it may be further treated with heat or formaldehyde.

The thiol redox (SH) agents of the invention may also be used to treat individuals who are suffering the effects of neurotoxicity caused by a venomous snake bite. The preferred method of administering the reduced thiol redox (SH) agent to the individual is by multiple subcutaneous injections around the snake bite.

Of course the correct amount of a thiol redox (SH) agent used to detoxify a neurotoxin in an individual will depend upon the amount of toxin the individual actually recived from the bite. However, effective amounts for detoxifying or reducing the toxicity of snake neurotoxins in mice usually range from about 0.01 μg to 0.3 μg, preferably about 0.02 μg to 0.05 μg, of a reduced thioredoxin; from about 0.1 nanomole to 3.0 nanomoles, preferably from 0.2 nanomole to 1.0 nanomole, of reduced lipoic acid in the presence of about 0.05 μg of a thioredoxin; from about 1.0 nanomole to 30 nanomoles, preferably from 2.0 nanomoles to 5.0 nanomoles, of DTT, preferrably in the presence of 0.05 μg of a thioredoxin, for every gm of mouse body weight.

The effective amounts for detoxifying a snake neurotoxin in a mouse using the components of the NADP-thioredoxin system range from about 0.01 μg to 0.3 μg, preferably about 0.02 μg to 0.05 μg of a thioredoxin; from about 0.005 μg to 0.12 μg, preferably from 0.01 μg to 0.025 μg, of NTR and from about 5 nanomoles to 30 nanomoles, preferrably 10 nanomoles to 15 nanomoles, NADPH for every gm of mouse body weight.

The preferred method of administering the NTS to an individual is also by multiple subcutaneous injections. The preferred thiol redox agent for human use is human thioredoxin administered via the NADP-thioredoxin system or with lipoic acid or DTT.

A partial list of the venomous snakes which produce the neurotoxins which can be inactivated or detoxified by the methods of this invention appears on pages 529–555 of Chippaur, J.-P. et al. (1991) *Reptile Venoms and Toxins,*

A. T. Tu, ed., Marcel Dekker, Inc., which is herein incorporated by reference.

Other features and advantages of the invention with respect to inactivating and detoxifying venome can be ascertained from the following examples.

EXAMPLE 26

Reduction Studies of Bee, Scorpion and Snake Venoms and Labeling with mBBr

Reactions were carried out with 50 μg venom (final volume of 100 μl) in 30 mM Tris-CH1 buffer pH 7.9 containing the following protease inhibitors: phenylmethylsulfonyl fluoride (PMSF), leupeptin and pepstatin (final concentrations used in the assay respectively: 100 μM, 1 μM and 1 μM). With NADPH as a reductant, the mixture also contained 4 μg thioredoxin, 3.5 μg NTR (both from $E.$ $coli$) and 12.5 mM NADPH. When thioredoxin (4 μg, $E.$ $coli$ or human) was reduced by DTT, NADPH and NTR were omitted and DTT was added to 0.5 mM. Assays with GSH were performed similarly but at a final concentration of 5 mM and in the presence of 1.5 μg glutathione reductase and 12.5 mM NADPH. The mixture was incubated for 20 min at room temperature, mBBr was then added to 1.5 mM and the reaction was continued for 15 min at room temperature. The reaction was stopped and excess mBBr derivitized by adding 10 μl of 100 mM β-mercaptoethanol, 5 μl of 20% SDS and 10 μl of 50% glycerol. Samples were then analyzed by SDS-polyacrylamide gel electrophoresis as previously described.

The same experiment with the NADP-thioredoxin system was performed without adding protease inhibitors.

After 20 min incubation at room temperature with different reductants and in the presence of protease inhibitors, the samples were derivatized with mBBr and separated by electrophoresis and fluorescence was determined. It was shown that in all cases thioredoxin ($E.$ $coli$ or human) specifically reduced components of the venoms. The gel also showed that thioredoxin reduces venom components in a similar way when the reaction was performed in the absence of protease inhibitors.

The reduction of bee, scorpion and snake venoms by the NADP-Thioredoxin system with and without protease inhibitors was also shon using the SDS-Polyacrylamide gel mBBr procedure. After 20 min incubation at room temperature with NTS in the presence or absence of any protease inhibitors, the samples were derivatized with mBBr, separated by electrophoresis, and fluorescence was determined as previously described.

Materials

Venoms: Been venom from $Apis$ $mellifera$, scorpion venom from $Androctonus$ $australis$, and snake venom from $Bungarus$ $multicinctus$ were purchased from Sigma chemical Co. (St. Louis, Mo.).

Protease Inhibitors: Phenylmethylsulfonyl fluoride (PMSF), Leupeptin and Pepstatin were purchased from Sigmal Chemical Co. (St. Louis, Mo.).

Venom Detoxification

Detoxification of bee, scorpion and snake venoms is determined by subcutaneous injection into mice. Assays are done in triplicate. Prior to injection, the venom is diluted in phosphate-saline buffer (0.15 M NaCl in 10 mM $Na_2HPO_4$/$NaH_2PO_4$ pH 7.2) at concentrations ranging up to twice the $LD_{50}$ (per g mouse): bee venom from $Apis$ $mellifera$, 2.8 μg; scorpion venom from $Androcionus$ $australis$, 0.32 μg; and snake venom from $Bungarus$ $multicinctus$, 0.16 μg. At 5, 10, 30, 60 minutes and 4, 12 and 24 hr after injection, separate groups of challenged mice are injected (1) intravenously and (2) subcutaneously (multiple local injections around the initial injection site). The thioredoxin is reduced with: (1) $E.$ $coli$ NADP-thioredoxin system, using 0.08 μg thioredoxin, 0.07 μg NTR and 25 nmoles NADPH; (2) Thioredoxin reduced by DTT or reduced lipoic acid (0.08 μg $E.$ $coli$ or human thioredoxin added to 1 nmole dithiothreitol or 1 nmole of reduced lipoic acid). Concentrations are per μg venom injected into the animal; all solutions are prepared in phosphate-saline buffer.

The effect of thioredoxin on detoxification is determined by (1) comparing the $LD_{50}$ with the control group without thioredoxin and (2) following the extent of the local reaction, as evidenced by necrosis, swelling and general discomfort to the animal.

Reduction Studies for Reducing Snake Neurotoxins—Materials and Methods

Toxins

Porcine pancreas phospholipase $A_2$, erabutoxin b and β-bungarotoxin were purchased from Sigma Chemical Co. (St. Louis, Mo). As the phospholipase $A_2$ was provided in 3.2 M $(NH_4)_2SO_4$ solution pH 5.5, the protein was dialysed in 30 mM Tris-HCl buffer, pH 7.9, using a centricon 3 KDa cutoff membrane. α-Bungarotoxin and α-bungarotoxin$^{125}$I were a kind gift from Dr. Shalla Verrall.

Reagents and Fine Chemicals

DL-α-Lipoic acid, L-α-phosphatidylcholine from soybean, NADPH and β-mercaptoethanol were purchased from Sigma Chemical Co. (St Louis, Mo.) and monobromobimane (mBBr, trade name thiolite) from Calbiochem (San Diego, Calif.). Reagents for sodium dodecylsulfate (SDS)-polyacrylamide gel electrophoresis were purchased from Bio-Rad Laboratories (Richmond, Calif.).

Proteins and Enzymes

Thioredoxin and NTR were purified from $E.$ $coli$ as is described by Jiao et al., (1992) $Ag.$ $Food$ $Chem.$ (in press). Thioredoxin h was purified from wheat germ (Florencio, F. J. et al. (1988) $Arch$ $Biochem.$ $Biophys.$ 266:496–507) and thioredoxins f and m from spinach leaves (Florencio, F. J. et al., supra.). Human thioredoxin was a kind gift of Dr. Emanuelle Wollman. NADP-malate dehydrogenase was purified from corn leaves (Jacquot, J.-P. et al. (1981) $Plant$ $Physiol.$ 68:300–304) and glutathione reductase from spinach leaves (Florencio, F. J. et al., supra.). $E.$ $coli$ glutaredoxin was a kind gift of Professor A. Holmgren.

SDS-Polyacrylamide Gel Electrophoresis

SDS-polyacrylamide gel electrophoresis was performed in 10–20% gradient gels of 1.5 mm thickness that were developed for 3 hr at a constant current of 40 mA. Following electrophoresis, gels were soaked for 2 hr in 12% (w/v) trichloroacetic acid and then transferred to a solution containing 40% methanol and 10% acetic acid for 12 hr to remove excess mBBr. The fluorescence of protein-bound mBBr was determined by placing gels on a light box fitted with an ultraviolet light source (365 nm). Gels were photographed with Polaroid positive/negative Landfilm, type 55, through a yellow Wratten gelatin filter No. 8 (cutoff=460 nm) (exposure time 40 sec. at f4.5). Gels were stained for protein for 1 hr in solution of 0.125% (w/v) Coomassie blue R-250 in 10% acetic acid and 40% methanol. Gels were destained in this same solution from which Coomassie blue was omitted.

Polaroid negatives of fluorescent gels and dry stained gels were scanned with a laser densitometer (Pharmacia-LKB Ultroscan XL). The bands were quantified by evaluating areas or height of the peaks with Gelscan XL software.

EXAMPLE 27

Reduction of Toxins and Labeling with mBBr

Reactions were carried out with 10 μg of target toxin in a final volume of 100 μl in 30 mM Tris-HCl buffer, pH 7.9, with 0.8 μg thioredoxin, 0.7 μg NTR (both from $E.$ $coli$) and 2.5 mM NADPH. When thioredoxin was reduced by DTT, NADPH and NTR were omitted and DTT was added to 0.5 mM. Assays with GSH were performed similarly, but at a final concentration of 1 mM. For reduction by glutaredoxin, the thioredoxin and NTR were replaced by 1 μg $E.$ $coli$ glutaredoxin, 0.38 μg glutathione reductase (partially purified from spinach leaves), 1 mM GSH and 2.5 mM NADPH (the combination of these four components is called NADP/ glutaredoxin system). Reduction by the reduced form of lipoic acid, was carried out in a volume of 100 μl at two concentrations, 100 μM and 200 μM, both alone and with 0.8 μg of thioredoxin. The mixture was incubated for 2 hr at 37° C. in the case of erabutoxin b and α-bungarotoxin, 1 hr at room temperature for β-bungarotoxin and 20 min at room temperature for phospholipase $A_2$. After incubation, mBBr was added to 1.5 mM and the reaction continued for 15 min at room temperature. The reaction was stopped and excess mBBr derivatized by adding 10 μl of 100 mM β-mercaptoethanol, 5 μl of 20% SDS and 10 μl 50% glycerol. Samples were then analyzed by SDS-polyacrylamide gel electrophoresis.

Total toxin reduction was accomplished by boiling samples for 3 min in 2 mM DTT. After cooling, the samples were labeled with mBBr and treated as before, except that all samples were again boiled for 2 min prior to loading in the gel. Dithiothreitol (DMT) and the reduced forms of thioredoxin and lipoic acid are dithiol reductants as opposed to monothiol reductants like 2-mercaptoethanol and glutathione. DTT is a synthetically prepared chemical agent, whereas thioredoxin and lipoic acid occur within the cell. Erabutoxin b was significantly reduced by the NTS, DTT and thioredoxin and reduced lipoic acid and thioredoxin. With erabutoxin b lipoic acid was shown to be more specific reductant than dithiothreitol. Dithiothreitol reduced the toxin partly without thioredoxin whereas reduced lipoic acid did not (lane 8). The results also showed that the NTS or DTT plus thioredoxin are specific reductants for α-bungarotoxin and β-bungarotoxin.

EXAMPLE 28

NADP-Malate Dehydrogenase Activation

The ability of snake toxins to activate chloroplast NADP-malate dehydrogenase was carried out by preincubating 5 μg toxin with a limiting thioredoxin concentration (to restrict activation of the enzyme by the thioredoxin): $E.\ coli$ thioredoxin, 0.25 μg; human, 0.9 μg; wheat, 1.15 μg; spinach f and m, 0.375 and 0.125 μg, respectively. Purified corn NADP-malate dehydrogenase, 1.4 μg, was added to a solution containing 100 mM Tris-HCl, pH 7.9, thioredoxin as indicated, and 10 mM DTT (final volume 0.2 ml). After 25 min, 160 μl of the preincubation mixture was injected into a 1 cm cuvette of 1 ml capacity containing (in 0.79 ml) 100 mM Tris HCl, pH 7.9, and 0.25 mM NADPH. The reaction was started by the addition of 50 μl of 50 mM oxalacetic acid. NADPH oxidation was followed by monitoring the change in absorbance at 340 nm with a Beckman spectrophotometer fitted with a four-way channel changer. The results of this experiment showed that the reduction by different reduced thioredoxins of erabutoxin b significantly alters the toxin's biological ability to activate NADP-malate dehydrogenase. The results demonstrate that, although there are differences in effectiveness, all thioredoxins tested function to some extent in limiting the effect of the toxin.

EXAMPLE 29

Proteolysis Assay of Erabutoxin b

Erabutoxin b, 10 μg was incubated for 2 hr at 37° C. with 30 mM Tris-HCl buffer pH 7.9 (total volume, 100 μl). As indicated, the buffer was supplemented with 0.8 μg thioredoxin, 0.7 μg NTR and 2.5 mM NADPH. When thioredoxin was reduced by DTT the NTR and NADPH were omitted and DTT was added to 0.5 mM. Following incubation, samples were digested with 0.4 and 2 μg of trypsin for 10 min at 37° C. DTT, 4.8 μl of 50 mM solution, 5 μl of 20% SDS and 10 μL of 50% glycerol were added, samples were boiled for 3 min, and then subjected to SDS-polyacrylamide gel electrophoresis. Gels were stained with Coomassie blue and the protein bands quantified by densitometric scanning as described above. The results of the assay are shown in Table XVI below. These results show that reduction of a snake neurotoxin (erabutoxin b) renders the toxin more susceptible to proteolysis. An extension of this conclusion would indicate that administration of reduced thioredoxin as a toxin antidote should help to destroy the toxin owing to the increase in proteolytic inactivation by proteases of the venom.

TABLE XVI

Susceptibility of the Oxidized and Reduced Forms of Erabutoxin b to Trypsin

| Treatment | % Erabutoxin b digested | |
|---|---|---|
| | 0.4 μg trypsin | 2 μg trypsin |
| Control | 0.0 | 34.1 |
| Reduced, NTS | 21.1 | 57.8 |
| Reduced, DTT | 3.1 | 40.6 |
| Reduced, DTT + Trx | 28.0 | 71.8 |

Erabutoxin b, 10 μg was preincubated for 2 hours at 37° C. in 30 mM Tris-HCl buffer, pH 7.9, as follows: control, no addition; reduced by $E.\ coli$ NADP/thioredoxin system (NTS), thioredoxin, NTR and NADPH; reduced by DTT, DTT; and reduced by DTT plus thioredoxin, DTT supplemented with $E.\ coli$ thioredoxin. After preincubation 0.4 μg and 2 μg of trypsin were added to the indicated which then were analyzed by SDS-polyacrylamide gel electrophoresis.

EXAMPLE 30

Phospholipase $A_2$ Assay

Activity of the oxidized and reduced forms of the phospholipase $A_2$ component of β-bungarotoxin was determined spectrophotometrically following change in acidity as described by Lobo de Araujo et al. (1987) *Toxicon* 25:1181–1188. For reduction experiments, 10 μg toxin was incubated in 30 mM Tris-HCl buffer, pH 7.9, containing 0.8 μg thidredoxin, 0.7 μg NTR and 7 mM NADPH (final volume, 35 μl). After 1 hr incubation at room temperature, 20 μl of the reaction mixture was added to a 1 cm cuvette containing 1 ml of assay solution (adjusted to pH 7.6) that contained 10 mM $CaCl_2$, 100 mM NaCl, 4 mM sodium cholate, 175 μM soybean phosphatidylcholine and 55 μM phenol red. The reaction was followed by measuring the change in the absorbance at 558 nm in a Beckman Du model 2400 spectrophotometer. The results of this experiment demonstrated that β-bungarotoxin loses most of its phospholipase activity when reduced by thioredoxin. The results are consistent with the conclusion that the administration of reduced thioredoxin following a snake bite would help detoxify the toxin by eliminating phospholipase $A_2$ activity.

EXAMPLE 31

α-Bungarotoxin binding to Acetylcholine Receptor

α-Bungarotoxin binding was assayed with cultured mouse cells by using radiolabeled toxin (Gu, Y. et al. (1985) *J. Neurosci.* 5:1909–1916). Mouse cells, line $C_2$, were grown as described by Gu et al (Gu, Y. et al., supra.) and plated in 24-well plastic tissue culture plates (Falcon) at a density of about 3000 cells per well. Growth medium was replaced by fusion medium after 48 hr and again after 96 hr. Cultures were used for assay after an additional 2 days growth.

α-Bungarotoxin binding was determined with cells subjected to three different treatments: [A] 10 nM α-bungarotoxin[125]I (262 Ci/mmole) was preincubated 2 hr at 37° C. in 200 μl of phosphate-saline buffer (0. 15M NaCi in 10 mM $Na_2HPO_4$/$NaH_2PO_4$ pH 7.2) with 4 μg thioredoxin, 3.5 μg NTR (both from $E.\ coli$) and 6.25 mM NADPH. In certain cases, the NTR and NADPH were replaced by 1.25 mM DTT. After 2 hr incubation, the mixture was transferred to a well containing mouse cells, washed two times with phosphate-saline, and incubated for 2 hours at 37° C. [B] After washing the cells two times with phosphate-saline buffer, 10 nM α-bungarotoxin$^{125}$I (in 200 μl of phosphate-saline) was added per well. Following a 2 hr incubation at 37° C., cells were washed again with phosphate-saline buffer to remove unbound toxin. As indicated, 200 μl saline, supplemented with 0.68 mM CaCl$_2$, 0.49 mM MgCl$_2$, 4 μg thioredoxin, 3.5 μg NTR and 6.25 mM NADPH were added to the well. The plate was incubated 2 hr at 37° C. NTR and NADPH were omitted from treatment with DTT which was added at 1.25 mM. [C] After washing cells twice with phosphate-saline buffer, 200 μl of a solution containing 4 μg thioredoxin, 3.5 μg NTR and 6.25 mM NADPH, were added to each well. In some cases, NTR and NADPH were replaced with 1.25 mM DTT. The plate was incubated for 2 hr at 37° C. Cells were then washed twice with phosphate-saline buffer to remove the added reductant. Phosphate-saline buffer, 200 μl, containing 0.68 mM CaCl$_2$ and 0.49 mM MgCl$_2$ and 10 nM α-bungarotoxin$^{125}$I was added to each well. Incubation was continued for 2 hr at 37° C. The results of this assay are shown in Table XVII. This experiment shows that when reduced by thioredoxin, β-bungarotoxin can no longer bind to the acetylcholine receptor. When extended to the whole animal, the thioredoxin-linked reduction mechanism would result in detoxification by eliminating binding of the toxin to its target receptor.

Each α-bungarotoxin binding assay was done in triplicate. Nonspecific binding was measured by adding 100-fold excess unlabeled α-bungarotoxin to the incubation mixture. After the incubation period, the cells in all cases were washed with phosphate-saline to remove unbound toxin. The amount of toxin bound was determined by solubilizing the cells in 0.1 M NaOH and measuring radioactivity in a gamma counter.

TABLE XVII

Binding of α-Bungarotoxin to the Acetylcholine Receptor of Mouse Cells

| Treatment A | % Binding |
|---|---|
| Toxin + Reductant →(2 hr, 37° C.) cells →(2 hr, 37° C.) STOP | |
| No reductant | 100.0 |
| NTS | 0.0 |
| DTT plus Thioredoxin | 0.0 |
| NTS minus NTR | 63.0 |
| NTS minus Thioredoxin | 78.0 |
| NTS minus NADPH | 101.0 |
| Treatment B | |
| Toxin + Cells →(2 hr, 37° C.) wash cells + reductant →(2 hr, 37° C.) STOP | |
| No reductant | 100.0 |
| NTS | 78.0 |
| DTT plus Thioredoxin | 76.0 |
| Treatment C | |
| Cells + Reductant →(2 hr, 37° C.) wash cells + toxin →(2 hr, 37° C.) STOP | |
| No reductant | 100.0 |
| NTS | 68.7 |
| DTT | 85.0 |
| DTT plus Thioredoxin | 68.8 |

E. coli NTS: thioredoxin, NTR and NADPH

EXAMPLE 32

Example for Detoxification in an Animal

Detoxification of snake neurotoxins is determined by subcutaneous injection into mice. Assays are done in triplicate. Prior to injection, the toxin is diluted in phosphate-saline buffer (0.15 M NaCl in 10 mM Na$_2$HPO$_4$/NaH$_2$PO$_4$ pH 7.2) at concentrations ranging up to twice the LD$_{50}$ dose. (LD$_{50}$ is defined as that dose of toxin that kills 50% of a given group of animals.) For toxicity tests, the following neurotoxin concentrations correspond to the LD$_{50}$ (per g mouse): erabutoxin b, 0.05 μg–0.15 μg; α-bungarotoxin, 0.3 μg; and β-bungarotoxin, 0.089 μg. At 5, 10, 30, 60 minutes and 4, 12 and 24 hr after injection, separate groups of the challenged mice are injected (1) intravenously, and (2) subcutaneously (multiple local injections around the initial injection site). The thioredoxin is reduced with: (1) the E. coli NADP-thioredoxin system, using 0.08 μg thioredoxin, 0.07 μg NTR and 25 nanomoles NADPH; (2) Thioredoxin plus 1–2 nanomoles of reduced lipoic acid, using 0.08 μg E. coli or 0.20 μg human thioredoxin, and (3) using 0.08 μg E. coli or 0.20 μg human thioredoxin with 5 nanomoles dithiothreitol (concentrations are per μg toxin injected into the animal; all solutions are prepared in phosphate-saline buffer).

The effect of thioredoxin on detoxification is determined by (1) comparing the LD$_{50}$ with the control group without thioredoxin; (2) following the extent of the local reaction, as evidenced by necrosis, swelling and general discomfort to the animal; (3) following the serum levels of creatin kinase, an indicator of tissue damage. Creatin kinase, which is released into the blood as a result of breakage of muscle cells, is monitored using the standard assay kit obtained from Sigma Chemical Co. (St. Louis, Mo.).

The symptoms of snake bite are multiple and depend on a variety of factors. As a consequence, they vary from patient to patient. There are, nonetheless, common symptoms that thioredoxin treatment should alleviate in humans. Specifically, the thioredoxin treatment should alleviate symptoms associated with neurotoxic and related effects resulting from snake bite. Included are a decrease in swelling and edema, pain and blistering surrounding the bite; restoration of normal pulse rate; restriction of necrosis in the bite area; minimization of the affected part. A minimization of these symptoms should in turn result in improvement in the general health and state of the patient.

Reduction of Food Proteins and Allergens

The invention provides a method for chemically reducing the disulfide bonds in major food proteins particularly food allergen proteins and for decreasing or eliminating the allergenicity that occurs when foods containing those proteins are ingested. The invention also provides a method for increasing the digestibility of food proteins and therefore food. The disulfide bonds are reduced to the sulfhydryl (SH) level by thioredoxin. The other major cellular thiol reductant, glutathione, was inactive in this capacity. The proteins are allergenically active in the oxidized (S—S) state; when treated with thioredoxin (SH state), they lose allergenicity. Thioredoxin achieves this reduction when activated (reduced) either by NADPH via the enzyme NADP-thioredoxin reductase, (physiological conditions) or by dithiothreitol, a synthetic chemical reductant.

Presumably the proficiency of reduced thioredoxin to decrease or eliminate the allergenicity caused by the food depends upon the ability of the reduced thioredoxin to reduce the intramolecular disulfide bonds in the allergenic proteins in the food.

Food proteins that have intramolecular disulfide bonds can be reduced and the allergenicity of foods containing these proteins can be at least decreased and the digestibility increased by reduced thioredoxin when the food is treated with the thioredoxin for an effective period of time at an effective temperature. The effective temperature for incubating the food is from about 4° C. to 55° C. but any temperature which will allow the reduction of the disulfide bonds is acceptable. The effective time for incubation is from about 20 min to 2 hrs but again any time that allows for reduction of the disculfide bonds without significantly degrading food quality is acceptable. For example, the proteins may also be reduced and remain reduced by incubation at about 4° C. for about 48 hrs.

Examples of the foods that will exhibit reduced allergenicity and increased digestibility upon treatment with reduced thioredoxin are beef, milk, soy, egg, rice, wheat and nuts.

A preferred method for decreasing the allergenicity and increasing the digestibility of food ingested by a mammal is to pretreat or incubate the food using the components in the NADP-thioredoxin system (NTS). In general, the effective amounts of the components range from about 0.01 mg to 4.0 mg, preferably about 0.10 mg to 2 mg of thioredoxin; from about 0.01 mg to 4 mg, preferably from about 0.20 mg to 2 mg of NTR and from about 1 micromole to 250 micromoles, preferably about 25 micromoles to 100 micromoles of NADPH for every 1.0 gm of protein in the food. Of course, the effective amounts of each component will vary depending upon the amount of the other components, the time and temperature of incubation, as well as the particular food and the amount of innate thioredoxin and its reductants in that food. For example, the above amounts of thioredoxin were determined on the basis of using 1 mg NTR and 100 micromoles NADPH per gram of food protein. The range of NADPH was determined on the basis of using 1 mg NTR and 1 mg thioredoxin. The appropriate component amounts may also be affected by prior treatment of the food and the type of animal and its condition.

Other features and advantages of the invention with respect to decreasing the allergenicity and increasing the digestibility of a particular food can be ascertained from the following examples.

EXAMPLE 33

Treatment of Milk, Soy, Wheat and Beef with Thioredoxin

For this study a 1 to 5 physiological saline (PBS) dilution of a stock, 1:20 weight/volume (w/v), cow's milk allergenic extract (Catalogue No. 3390JG, Miles, Inc., Elkhart, Ind.), a 1 to 10 PBS dilution of a stock, 1:10 w/v, soy allergenic extract (Catalogue No. 3597ED, Miles, Inc., Elkhart, Indiana) and a 1 to 5 PBS dilution of a stock; 1:10 w/v, wheat allergenic extract (Catalogue No. 3708ED, Miles, Inc., Elkhart, Ind.) were prepared. A 1 to 5 PBS dilution of a stock, 1:10 w/v, commercial beef allergenic extract (Catalogue No. 3078JF, Miles, Inc., Elkhart, Ind.) was also prepared.

In the case of cow's milk, 0.1 ml of the dilution was treated with the NADP/thioredoxin system (NTS) which comprised incubating the allergen in this instance with 4.8 micrograms thioredoxin, 4.2 micrograms NTR and 1 mM NADPH (final volume, 0.2 ml). A second sample was also prepared using 0.1 ml of the diluted milk allergen incubated with 1.5 mM DTT and 4.8 micrograms thioredoxin (final volume, 0.2). In all the allergen studies, including the studies in this Example and the ones following, the thioredoxin and NTR used were purified as previously described from $E.\ coli$ that had been transformed to overproduce those proteins (de la Motte-Guery, F. et al. (1991) $Eur.\ J.\ Biochem.$ 196:287–294, and Russel, M. et al. (1988) $J.\ Biol.\ Chem.$ 263:9015–9019). For soy and wheat, 0.05 ml of the dilutions were incubated with 2.4 micrograms thioredoxin, 2.1 micrograms NTR and 1 mM NADPH. In addition, an identical treated control sample of PBS was prepared. DTT treated soy and wheat samples were also prepared using 0.05 ml of the separate allergen dilutions incubated with 1.5 mM DTT and 2.4 micrograms thioredoxin. The final volume for the control and all the soy and wheat samples was 0.1 ml. The milk and wheat preparations were incubated at room temperature for 25 min while the soy preparation was incubated at 37° C. for 1 hr and 25 min. With the beef, 0.05 ml of the dilution was incubated with 2.4 micrograms thioredoxin, 2.1 micrograms NTR and 1 mM NADPH (final volume, 0.1 ml) for 25 min at 37° C. Another 0.05 ml sample was treated the same way but at room temperature. Following incubation 1 ml dilutions ranging from $1\times10^3$ to $1\times10^6$ or from $1\times10^3$ to $1\times10^9$ were prepared for each treated food extract preparation. The diluted samples were used for testing within 30 min.

EXAMPLE 34

Determination of the Reduction of Food Allergens by the NADP/Thioredoxin System and Increase in Proteolysis Using the mBBr Fluorescent Labelini/ SDS-Polyacrylamide Gel Electrophoresis Method For this study a 1 to 2.5, 1 to 5 and 1 to 1.5 dilution with PBS of the stock cow's milk, beef and wheat extracts described in Example 33 were respectively prepared. To 50 microliters of these dilutions were added 2.4 micrograms thioredoxin, 2.1 micrograms NTR and 1 mM NADPH (final volume, 0.1 ml). The controls consisted of 50 microliters of the particular diluted extract and 50 microliters of PBS. The preparations were incubated for 25 min at room temperature and also at 37° C. After incubation, 8 μl of 80 mM mBBr was added and the reaction continued for 15 min at room temperature. The reaction was stopped and excess mBBr derivatized by adding 10 μl of 100 mM β-mercaptoethanol, 10 μl of 20% SDS and 10 μl of 50% glycerol. The samples were analyzed by the mBBr/SDS-polyacrylamide gel electrophoresis technique previously described. The results showed that the NTS effectively reduced the proteins in the allergenic extracts at both room temperature and 37° C. In an additional study, where a PBS dilution of the soy stock extract described in Example 33 was similarly treated with the NTS, an analysis using the mBBr labeling/SDS-PAGE method showed that thioredoxin also reduced the soy proteins. However, when soy, cow's milk, wheat, egg and beef allergenic proteins were incubated with glutathione, glutathione reductase and NADPH, there was minimal or no reduction of those treated allergenic proteins.

A PBS dilution of a commercial rice allergenic extract (Catalogue No. 3549ED, Miles, Inc., Elkhart, Ind.) is also similarly incubated with the NTS and analyzed using the mBBr/SDS-PAGE technique to show that reduced thioredoxin reduces rice allergen proteins.

In a separate study, it was also observed that food allergen proteins from the commercial extracts described in Example 33 that had been reduced by the NTS and were further incubated with trypsin had an increased susceptibility to proteolysis over controls that had not been treated with the NTS. The analysis of the reduction was done using the mBBr/SDS-PAGE techniques. Further in this study, when 10 μg of an NTS reduced purified milk allergen protein, β-lactoglobulin (Sigma Chemical Co.), was treated with 2 μg of trypsin, proteolysis was 100% as compared with only 50% for the identically trypsin treated oxidized β-lactoglobulin. When 10 μg of another purified milk allergen, oxidized α-lactalbumin (Sigma Chemical Co.), was similarly treated with 2 μg trypsin, there was no noticeable proteolysis. However, 10 μg of purified α-lactalbumin reduced by the NTS was proteolyzed 80% by trypsin. Also 10 μg of α-lactalbumin reduced by 0.8 μg of thioredoxin and 0.5 mM DTT was 100% proteolyzed by 2 μg of trypsin.

EXAMPLE 35

Reduction of Egg White Proteins

Dried chicken egg white was purchased from Sigma Chemical Co. About 80% of the total proteins in egg white are allergens. A solution of 20 mg/ml egg white was resuspended in PBS. Since not all the material was dissolved, it was centrifuged at 14,000 RPM for 2 min. The soluble egg white proteins were used for the reduction study using mBBr fluorescent labelling and SDS-polyacrylamide gel electrophoresis analysis. The treatments used were the control (no reductant), NTS, DTT plus thioredoxin, reduced glutathione (GSH) and reduced glutathione/glutathione reductase/NADPH. Reactions were carried out in PBS with 23 microliters of the soluble proteins from the 20 mg/ml egg white suspension in a final volume of 100 microliters. In the NTS, 7.5 mM NADPH, 2.4 micrograms thioredoxin and 2.1 micrograms NTR were used. When thioredoxin was reduced by DTT, NADPH and NTR were omitted and DTT was added to 1.5 mM. The GSH concentration used was 3 mM. For reduction by the GSH/GR/NADPH system, 3 mM GSH, 4 micrograms GR and 7.5 mM NADPH were used. The mixture was incubated for 1 hr at room temperature. After incubation, 7 microliters of 80 mM mBBr was added and the reaction continued for 15 min at room temperature. The reaction was stopped and excess mBBr was derivatized by adding 10 microliters of 100 mM mercaptoethanol, 10 microliters of 20% SDS and 10 microliters of 50% glycerol. Samples were then analyzed by SDS-polyacrylamide gel electrophoresis. The results of this experiment showed that the NTS and DTT plus thioredoxin are very effective in reducing egg white proteins which are about 80% allergens. GSH or GSH/GR/NADPH showed the same level of reduction as the control and therefore is an ineffective reductant of egg white proteins.

EXAMPLE 36

Sensitization of Animals for Allergenicity Studies

The animals used in this study were atopic dogs born to different pairs of littermates from an in-bred colony of high IgE-producing spaniels.

A litter of 9 pups (4 males, 5 females) was born to an in-bred IgE-responder bitch sired by her brother. On newborn day 1, for the cow's milk, soy and rice studies, a nine-pup litter was divided into two groups: Group I of 5 pups was injected subcutaneously (SQ) in the right axilla with 1 μg the commercial soybean extract described in Example 33 in 0.2 ml alum; Group II of 4 pups was injected SQ in the right axilla with 1 μg of commercial dried cow's milk extract (described in Example 33) solubilized in 0.2 ml saline and 0.2 ml alum. All 9 pups were also given 1 μg of a stock 1:10 w/v rice allergenic extract (Catalogue No. 3549ED, Miles, Inc. Elkhart, Ind.) in 0.2 ml alum SQ in the left axilla.

At ages 3, 7 and 11 weeks, all pups were vaccinated with 0.5 ml of live attenuated distemper-hepatitis vaccine (Pitman-Moore, Washington's Crossing, Pa.) in the shoulder SQ. Two and 9 days after each vaccination, they were given the same food antigens that they received in the neonatal period, e.g., 5 dogs in Group I received 1 μg soybean extract in 0.2 ml alum, 4 dogs in Group 11 received 1 μg cow's milk in 0.2 ml alum, all 9 pups received 1 μg rice extract in 0.2 alum SQ in the right and left axilla, respectively.

A $^{125}$I-labelled rabbit anti-canine IgE serum (Frick, O. L. et al. (1983) *Am. J. Vet. Res.* 44: 440–445) was used in a RAST assay. Cyanogen-bromide activated filter paper discs were reacted with 100 μg of either soy, cow's milk or rice antigen, as in standard RAST protocol (Wide, L. et al. (1967) *Lancet* 2:1105–1107). A pool of newborn canine cord sera from non-atopic mongrel pups was used as a negative control or baseline cpm.

The pups were nursed for 6 weeks and weaned onto regular Puppy Chow (Ralston-Purina Company, St. Louis, Mo.) which included the sensitizing proteins, soybean meal, dried whey, and rice hulls; they were fed once/day and given water ad lib, under veterinary care and supervision at the University of California, Davis, Animal Resources Services, School of Veterinary Medicine. After 6 months, they were fed regular Field & Farm Dog Chow.

Between 3 and 4 months of age, when it was found that the pups were making IgE antibodies to a particular food antigen, all 9 pups in the litter were given double-blinded, 240 ml of either soy or cow's milk infant formula, tofu, rice gruel, or vanilla-flavored Vivonex protein hydrolysate (Norwich-Eaton Co., Norwich, Conn.) in the early morning. Abdominal girth was measured at umbilical level before the challenge and at 2 hours intervals during the day. They were observed closely by a veterinary technician for clinical signs of itching or rash, vomiting and frequency and character of stools, and for cough or respiratory distress and nasal discharge. They were monitored for such signs of reaction for 4 days. The next challenge feeding was given 7 days later.

All 9 pups in the litter gained weight and developed normally with no medical problems. They had no diarrhea or other gastrointestinal signs unless they were challenged with the food they had been sensitized to. Also no skin or respiratory abnormalities occurred. There were no untoward reactions to the vaccinations or immunizations.

Canine IgE-RASTs to the 3 food proteins were followed at fortnightly intervals with venous blood sampling.

Significantly more IgE-anti-food antibodies were produced by the corresponding milk (p<0.05 when challenged at 4 months) and soy (p<0.0005 for the first 3 months) immunized animals than by controls. The average titer for IgE-anti-rice-antibodies rose at 5–10 week, plateaued and then rose again sharply after 20–30 weeks of age. Also statistically significant reactions of diarrhea and abdominal bloat occurred in the soy and milk immunized animals when they were respectively fed soy and milk in their chow.

Another group of 8 dogs allergic to cow's milk, soy, wheat and beef were also developed in a manner similar to the method described above. Four littermate pups from another litter in the described in-bred colony of high IgE-producing spaniels were injected SQ in the right axilla with 1 μg each of the stock cow's milk, soy, wheat and beef allergenic extracts described in Example 33. Four pups from the same litter acted as controls. All eight pups were also given 1 μg of the rice extract in 0.2 ml alum SQ in left axilla. The pups were vaccinated as above and at two and nine days after each vaccination, were given the same food antigens in the same amount that they received as neonates. As above, they were fed foods which contained the appropriate sensitizing proteins (i.e., cow's milk, soy, beef and wheat) in a similar schedule. As with the previous soy and milk allergic animals, these immunized dogs produced significantly more anti-specific food IgE antibodies (including wheat and beef antibodies) than the controls. Again statistically significant reactions of diarrhea and abdominal bloat occurred in the immunized animals when they were challenged with food containing wheat, beef, soy or cow's milk.

EXAMPLE 37

Skin Test Determinations of the Decrease of Allergenicity in Food Allergens Treated with Reduced Thioredoxin Aliquots of 100 microliters of each dilution of the thioredoxin treated food allergen dilutions described in Example 33 were injected intradermally on the abdominal skin of the appropriate sensitized dogs described in Example 36 (e.g., cow's milk sensitized dogs were injected with the cow's milk dilutions). Prior to the allergen dilution injections, the dogs' forelimb veins were injected with 4 ml of 0.5% Evans blue dye. Dogs exhibiting an allergenic reaction developed blue colored wheals in the area of the allergen injection. After 10 minutes of development the size of the wheal (length and width) were measured. The observed size of the wheal and the dilution end point following injection of a concentration range of each allergen preparation were used as the allergenicity indicator. It was found that thioredoxin treatment gave 50% protection with $1 \times 10^5$ dilution of soy, full protection with a $3 \times 10^4$ dilution of milk, full protection with a $1 \times 10^6$ dilution of wheat and at least partial protection with a $1 \times 10^5$ dilution of beef (see FIGS. 1, 2, 3, 4 and 5 respectively).

EXAMPLE 38

Feeding Test Determinations of the Allergenicity of Food Allergens Treated with Reduced Thioredoxin Approximately one week prior to feeding, dogs sensitized in the manner described in Example 36 were skin tested intradermally as in Example 36 with the appropriate food allergen using the commercial allergenic extracts described in the previous examples. Based on these results, animals were separated into "control" and "thioredoxin-treated" groups. Each group was made up of representatives with complementary sensitivities—i.e., an equal number of strong, medium and weak reactors was selected for each group. Unless indicated otherwise, the groups were comprised of 3 animals (6 animals per experiment). For 3 days before and 5 days after the feeding challenge, dogs were maintained on a Hill's Prescription Diet Canine d/d diet (Hill's Division of Colgate Palmolive Co., Topeka, Kans.). Dogs were observed throughout this period for clinical symptoms such as retching and vomiting. Inaddition, stools were monitored and scored as an indicator of the allergenic response to the food being tested. The dogs' stools were counted for 3 days before and 3 days after the allergenic diet challenge and their consistency was indicated by a number: 1=firm, 2=soft, and 3=runny. The stool score was then calculated by multiplying the number of stools time the consistency factor. As an indicator of the allergenic response to the food allergens being tested, the final net average stool score per day for each group ("control", or "thioredoxin treated") was calculated by subtracting the average stool score per day before from that after the allergenic diet challenge. A higher net average stool score per day represents a stronger allergenic response.

The procedures used for preparing and administering the diets is given below. Unless indicated otherwise, reactions were carried out at room temperature.

Soy

Commercial soy formula (Isomil supplemented with iron, Ross Laboratories, Columbus, Ohio), 1.026 kg, was dissolved in 3 l of water. The solution was separated into two lots of 1.925 l, one used as the control and the other treated with the NADP/thioredoxin system (NTS) as follows. A mixture containing 45 micromoles NADPH, 564 micrograms NADP-thioredoxin reductase (NTR) and 1.125 mg thioredoxin (all dissolved in 30 mM Tris-HCl buffer, pH 7.9) was preincubated for 5 min and then added to one of the 1.925 l formula lots (henceforth the "thioredoxin-treated" lot). After adding the thioredoxin system, incubation was continued for an additional hour with constant stirring. An equal amount of buffer was added to the control lot. After incubation, 600 ml of formula was fed to each of the 3 dogs of the assigned group. The portions fed to the animals were equivalent to 25.0 gm of soy protein prior to incubation.

Wheat

Unbleached flour, 1.5 kg, was added to 3 l of water, previously heated to 37° C., in a gallon-size Waring blender. After 1 min blending, the flour suspension was divided equally into two lots, one was used as the control and the other treated with the NADP/thioredoxin system as follows. A mixture containing 45 micromoles NADPH, 564 micrograms (NTR) and 1.125 mg thioredoxin, all dissolved in 30 mM Tris-HCl buffer, pH 7.9 was preincubated for 5 min and then added to one lot (henceforth the "thioredoxin-treated" lot). An equivalent amount of buffer was added to the control lot. Both preparations were incubated 1 hr at 37° C. with frequent stirring. A volume of 600 ml was removed from each preparation, mixed with one can (15¾ oz) d/d, wheat free, rice/lamb based, dog food and fed to the 3 dogs of the assigned lot. Again these portions were equivalent to 25 gm of wheat protein. In the experiment with 8 dogs, the flour was increased to 2.0 kg and the procedure scaled up accordingly.

Milk

Preparations of dried CARNATION that had been reconstituted with water were similarly incubated with the NADP/thioredoxin system. As before 3 of the dogs received untreated and 3 received the treated milk. The final portions that the dogs received were equivalent to 10 gm of milk protein.

Results

The levels of components of the NADP/thioredoxin systems that were used were significantly higher than in the dough studies described above in Example 15. In this feeding study, preliminary trials indicated that higher levels of these compounds were required to reduce the allergenic proteins as determined in vitro by the mBBr/SDS-polyacrylamide gel procedure. The amounts of each component of the NADP/thioredoxin system used for each dog per gm protein in the feeding trials is indicated below relative to the amounts used in the baking tests:

|  | Wheat Flour, Milk, Soy Formula* |
| --- | --- |
| Thioredoxin | 5-X |
| NTR | 5-X |
| NADPH | 2-X |

*Amounts indicated are relative to those used in the above described baking tests in which 3 micrograms thioredoxin, 1.5 micrograms NTR and 0.3 micromoles NADPH were added per gram of flour protein. In the baking tests, loaves were baked with approximately 200 g flour or approximately 20 gm of flour protein. For the feeding experiments, food preparations were incubated with components of the NADP/thioredoxin system for one hour either at room temperature (milk and soy) or 37° C. (wheat).

Figure 6:
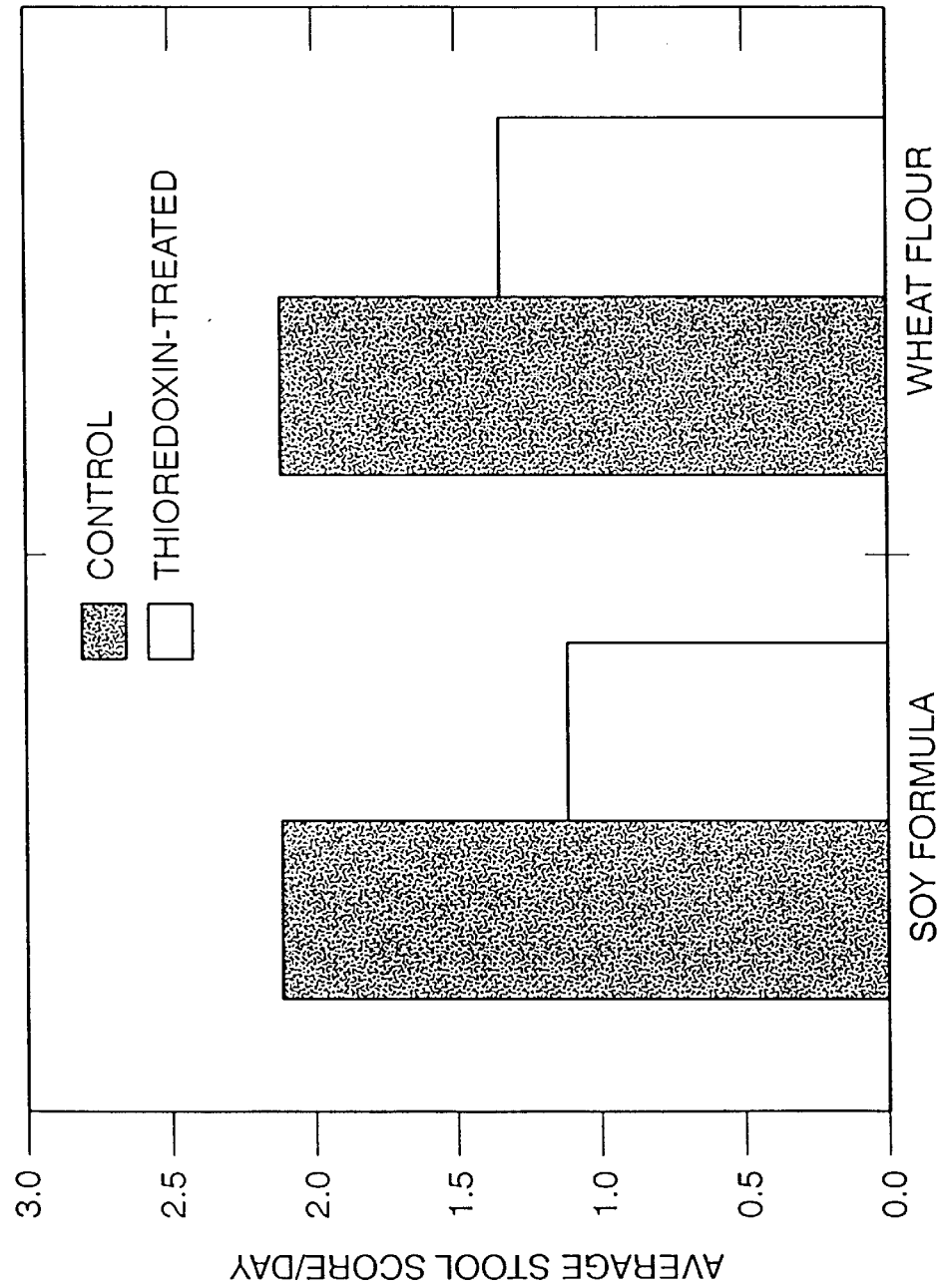
FIG. 6 is a bar graph showing the mitigation of a gastrointestinal allergenic response to soy and wheat by treating diets with reduced thioredoxin.

Based on "bedside symptoms" (vomiting and retching) as well as "stool score" (see FIG. 6), thioredoxin treatment was found to decrease the allergenic response of the dogs to the soy and wheat formulas. The allergenicity of the milk formula may also be decreased by treatment with the NTS. It should be noted that while the thioredoxin and NTR used were from E. coli, thioredoxins from other sources such as yeast and thioredoxin h and m may also be used.

EXAMPLE 39

Determination of the Increased Digestibility and Decreased Allergenicity of Thioredoxin Treated Milk Proteins and Raw Cow's Milk Milk allergy is caused by several proteins—$\alpha$-lactalbumin, serum albumin, caseins, and particularly $\beta$-lactoglobulin (BLG).

This example showed that the disulfide bonds of milk proteins and allergens were selectively and specifically reduced by thioredoxin. Once reduced, the most active of these allergens (BLG) showed not only a decrease in allergenicity, but also a striking increase in digestibility. The susceptibility of other milk disulfide proteins to pepsin also increased to some extent following reduction by thioredoxin.

Materials and Methods

Allergen Source

Raw cows milk was obtained from the experimental farm, University of California at Davis. Pure $\beta$-Lactoglobulin A and B and an 80% mixture of the two forms were purchased from Sigma Chemical Co., St. Louis, Mo.

Animals

Dogs obtained from the same colony of inbred, high IgE-producing atopic dogs used in Examples 36–38 were sensitized and maintained at the Animal Resources Service, School of Veterinary Medicine, University of California, Davis. These dogs, sensitized at birth, have been selected for a genetic predisposition to allergy and have a 15-year history of food and pollen hypersensitivity.

Cliemicals and Enzymes

Reagents for sodium dodecyl sulfatelpolyacrylamide (SDS/PAGE) were obtained from Sigma, Boehringer Mannheim, Indianapolis, Ind. and Biorad Laboratories, Hercules, Calif. DTT was purchased from Boehringer Mannheim and monobromobimane (mBBr), from Calbiochem, San Diego, Calif. Thioredoxin and NTR were purified from E.coli strains overexpressing the proteins. Glutathione reductase was purified from spinach leaves by the same procedure used for spinach NTR. Pepsin from porcine stomach mucosa, NADPH and other biochemical reagents were purchased from Sigma.

Food Sensitization of Atopic Dogs

Newborn pups from two litters of the atopic dog colony, designated CGB and GCB, were injected subcutaneously at day 1 with 1 µg each of wheat, cows milk and beef extract (Miles, Inc., Elkhart, Ind., described in Example 33) in 0.2 ml of alum. A third litter, designated CBB, was injected with a soy extract (Miles, Inc. described in Example 33) in addition to these same allergens. Procedures for the sensitization, testing and maintenance of the pups were substantially the same as those described in Example 36.

Skin Tests

About 3 min prior to skin testing, each dog received 4–5 ml of filtered 0.5% Evans blue dye solution (equivalent to 0.2 ml of 0.5% Evans blue dye per kg of weight) through a cephalic vein to enhance assessment of the cutaneous IgE antibodies. Serial dilutions of 100 µl of each sample were injected intradermally on the abdominal skin to establish the titer. After 15–20 min, the allergic response was determined by measuring the size of the blue wheal reaction (maximum length and width). An appropriate negative control (buffer diluted in physiological saline) was included for each animal tested. Repeated tests with thioredoxin, NTR, NADPH and pepsin alone were consistently negative.

Protein Assay

Protein concentration was determined by the Bradford method using bovine gamma globulin as the standard. Concentration of pure BLG was determined by its absorbance at 278 nm using a calculated molar extinction coefficient of 16800 (Gill, S. C. et al. (1989), Anal. Biochem. 182:319–326).

Protein Modeling

A model of BLG structure, determined by Brownlow et al. at 1.8 Å resolution, was provided by the Protein Data Bank, Brookhaven National Laboratory (Brownlow, S. et al. (1997), "Bovine beta-Lactoglobulin at 1.8 Resolution-Still an Enigmatic Lipocalcin", Structure 5:481–495). A model of the protein with single mutated C160S (partly reduced) and double mutated C160S—C106S (fully reduced), was built by the Swiss-Model program (Peitsch, M. C. (1996), "Pro-Mod and Swiss-Model: Internet-based tools for automated comparative protein modelling", Biochem. Soc. Trans. 24:274–279). A three dimension model of BLG was visualized by the RasMol program v2.6.

Protein Reduction

Reduction of the protein disulfide bonds was performed, in a volume of 100 µl with either: (i) the NADP/thioredoxin system (NTS), consisting of 5 µl of 25 mM NADPH, 8 µl of 0.3 mg/ml E. coli thioredoxin (i.e., 2.4 µg total thioredoxin) and 7 µl of 0.3 mg/ml E. coli NTR; or (ii) the NADP/glutathione system (NGS), composed of 5 µl of 25 mM NADPH, 10 µl of 30 mM reduced glutathione (GSH) and 15 µl of 0.1 mg/ml glutathione reductase. Reactions were carried out in physiological buffered saline solution (PBS; i.e., 10 mM $Na_2HPO_4$, 1.8 mM $KH_2PO_4$, 2.7 mM KCl and 137 mM NaCl, pH 7.4) containing either 10 µg of pure target protein or 50 µg of raw milk. The reaction mixtures were incubated at 4° C. overnight or at 37° C. and 55° C. for 45 min. For complete reduction, samples were incubated in PBS containing 5 µl of 100 mM DTT and boiled 5 min. The reduced proteins were visualized on gels by mBBr labeling and gel electrophoresis as described below. The extent of reduction was determined by scanning the gels.

Pepsin Assay

BLG, 640 µg, or milk, 1 mg protein (i.e., about 30 µl), was incubated with or without the thioredoxin system (NTS) at either 4° C. (to yield fully reduced form) or 55° C. (to yield partly reduced form), under the conditions described above.

The BLG, 320 µg, or milk, 500 µg protein, was then treated in 200 µl of simulated gastric fluid (SGF) as described by Astwood, J. D. et al. (1996), "Stability of food allergens to digestion in vitro", *Nature Biotechnol.* 14:1269–1273. SGF consists of 0.32% pepsin (w/v) and 30 mM NaCl adjusted at pH 1.2 with HCl (Board of Trustees (ed.) 1995, Simulated Gastric Fluid, TS., pp. 2053 in the *United States Pharmacopeia* 23, The National Formulary 18. United States Pharmacopeial Convention, Inc. Rockville, Md.). The reaction mixture was incubated at 37° C. and stopped by adding 0.375-fold volume of 160 mM $Na_2CO_3$ (ca. pH 7) after 0, 0.25, 1, 2, 4, 8, 15, 30 and 60 min incubation. The protein mixture was then subjected to SDS-PAGE (15% gels) and stained for protein with Coomassie blue as described below. As indicated, the allergenicity of the digested samples was determined by skin test analysis.

Feeding Challenges

Reduction of 80% pure BLG (a mixture of the A and B forms) was carried out for each dog in 100 ml of water. Each gram of BLG was treated by adding an aqueous mixture of 104 mg of NADPH, 1 mg of *E. coli* thioredoxin and 1 mg of *E. coli* NTR. The reactions occurred in a shaker at 125 rpm at 37° C. for 45 min. Samples were stored overnight at 4° C. The following day untreated (control) or treated BLG, 2.5 gm was mixed with a 12 oz. can of P/D food (Hills) and fed to a dog. Unchallenged animals received dog food alone without BLG while control animals received dog food with untreated BLG. Dogs were initially fed ¼ can of untreated food to initiate gastric flow. After 15 min, they were then fed at 3 intervals separated by 15 min ⅓ of a can of food that had been mixed with 2.5 g of either untreated or thioredoxin treated BLG. During these intervals dogs were monitored and their GI response assessed. Dogs were then observed and their response recorded at hourly intervals for the next 5 hr.

Data Analysis

The digestion response of the food challenged dogs described above was assessed by assigning numbers to the timing, volume and fluidity of vomit induced by feeding. Fluidity: no vomit=0, solid vomit=1, liquid vomit=2, liquid with blood or bile vomit=3. Volume: no vomit=0, small vomit=1 and large vomit=2. Timing: delayed vomit=1, immediate vomit=2.

mBBr Labeling and Analysis of Proteins

Sulfhydryl groups were visualized as their fluorescent mBBr derivatives. mBBr, 10 µl of a 100 mM solution, was added to each protein sample. After 20 min of incubation, the reaction was stopped by adding 10 µl of 100 mM 2-mercaptoethanol, 10 µl of 20% SDS and 20 µl of SDS/PAGE sample buffer containing 80% (v/v) glycerol and 0.005% bromophenol blue. Proteins were then separated by SDS/PAGE (10–20% acrylamide gradient) as described below. After electrophoresis, gels were placed in 12% trichloroacetic acid for 1 hr for fixation and then soaked overnight or longer in 40% (v/v) methanol and 10% (v/v) acetic acid with several changes to remove excess mBBr. The destained gels were then placed under 365 nm UV light to visualize fluorescent bands. Pictures were taken by either (i) Polaroid photographs (Positive/Negative Landfilm, type 55) through a yellow Wratten gelatin filter no. 8 with an exposure time of 45 s at f4.5, or (ii) the Nucleovision system of NucleoTech Corporation.

SDS/PAGE

Gels (10–20% acrylamide gradient, 1.5 mm thickness or 15% acrylamide, 0.75 mm thickness) were prepared according to Laemmli, U.K. (1970), "Cleavage of structural proteins during the assembly of the head of bacteriophage T4", *Nature* 227:680–685. After electrophoresis, gels were stained with 0.01% Coomassie brilliant blue R-250 in 40% methanol and 10% acetic acid for 1 hr and destained overnight with a solution of 20% ethanol and 10% acid acetic. Pictures were taken after destaining by either (i) Polaroid photograph (exposure time 1/15 s at f7) or (ii) the Nucleovision system of NucleoTech Corporation.

Sequence Analyses

The different forms of BLG (oxidized, partly and fully reduced, 10 µg) were separated as mBBr derivatives by SDS-PAGE (10–20% acrylamnide gradient, 1.5 mm thickness or 15% acrylamide, 0.75 mm thickness). An in-gel digestion method was used to obtain peptides containing cys residues that would allow structural characterization (Hwang, B. J. et al. (1996), "Internal sequence analysis of proteins eluted from polyacrylamide gels", *J. Chromatogr. B. Biomed. Appl.* 686:165–175). The dried gel used as starting material was placed in water to allow swelling and the cellophane layer was removed. The appropriate BLG bands were then cut out from the reconstituted gel. Each protein band was diced into 1 to 2 mm pieces. In brief, gel pieces were dehydrated in a speedvac, rehydrated in 0.1 M Tris buffer, pH 9 and 0.05% SDS, pH 9.0, containing 0.03 to 0.05 µg Lys-C endopeptidase (Wako) and incubated overnight at 30° C. Peptides were eluted by extracting the gel twice for 2 hr with water and twice for 2 hr with 70% acetonitrile/0.1% trifluoroacetic acid (TFA). The pooled extracts were dried, dissolved in a minimal volume of 6 M guanidine HCl-Tris, pH 8.2. Extracted peptides were then reduced with dithiothreitol (DTT) and alkylated with iodoacetamide. After the reaction, the mixture was diluted 4-× with water and the reduced guanidinium dodecylsulfate precipitate was removed by centrifugation. In-solution digestion was performed with trypsin in the diluted reaction mixture for complete digestion. Peptides were purified using a C18 microbore column (1 mm×15 cm, VYDAC) using an Applied Biosystems 172 HPLC system. After injection of sample, the column was washed with 95% solvent A (0.1% TFA in water)/5% solvent B (70 acetonitrile/0/075% TFA) for 10 min using a flow rate of 80 ul/min. Peptides were eluted with a gradient of 5 to 70% Solvent B for 90 min. Purified peptides were sequenced using either an ABI 477 or 470A sequencer with on-line HPLC identification of thenylthiohydratoin (PTH) amino acids. Peptides containing either Cys 160 and Cys 119 were isolated as indicated below. The disulfides of the fully oxidized protein correspond to Cys 106-Cys 119 and Cys 60-Cys 160. To identify the disulfide bonds involved in the partly and fully reduced forms, trypsin peptide (s) unique to each were isolated. The partly and fully reduced forms both showed the peptide: -$Leu_{149}$-Ser-Phe-Asn-Pro-Thr-Gln-Leu-Glu-Glu-Gln-$\underline{Cys}_{160}$-His-$Ile_{162}$. The fully reduced protein showed in addition the following peptide: -$Tyr_{102}$-Leu-Leu-Phe-$Cys_{106}$-Met-Glu-Asn-Ser-Ala-Glu-Pro-Glu-Gln-Ser-Leu-Ala-$\underline{Cys}_{119}$-Gln-$\underline{Cys}_{121}$-Leu-Val-.

Results

Reduction of Milk Proteins by the Thioredoxin System

Thioredoxin was effective in the reduction of the most prevalent disulfide protein of milk, namely BLG. To this end, the redox state of pure BLG (A and B forms) was monitored following treatment with the NADP/thioredoxin system (NTS), consisting of NADPH, NTR and thioredoxin. As described above, samples were incubated with the NTS system and then analyzed using the monobromobimane (mBBr)/SDS-polyacrylamide gel electrophoresis (PAGE) procedure. Here, as previously stated, the reduced (—SH) form of a target protein derivatized with mBBr and separated by SDS-PAGE, appears as a fluorescent band when viewed in ultraviolet light. It was found that, as seen in the previous Examples with a spectrum of proteins containing intramolecular disulfide bonds, the A and B forms of pure BLG were actively reduced by thioredoxin. When applied to milk, thioredoxin not only reduced BLG but also several other proteins, including α-lactalbumin as determined by the SDS/PAGE/mBBr labeling procedure used for the gel in FIG. 7. For this gel 50 μg of raw milk in PBS was applied to all lanes. The other variables for each lane are: Lane 1, control at 4° C., no addition; Lane 2, NTS, 55° C.; Lane 3, NTS, 4° C.; Lane 4, NGS, 55° C.; Lane 5, NGS, 4° C.; Lane 6, 5 mM DTT, 100° C., 5 min; Lane 7 was the same as Lane 6 except it was stained with Coomassie blue. Note that the excess of NADPH, NTR and thioredoxin maintained the target milk proteins in the reduced state throughout the experiment. The minor band traveling in front of the major (24 kDa) casein components (α and β) is κ-casein.

Figure 7:
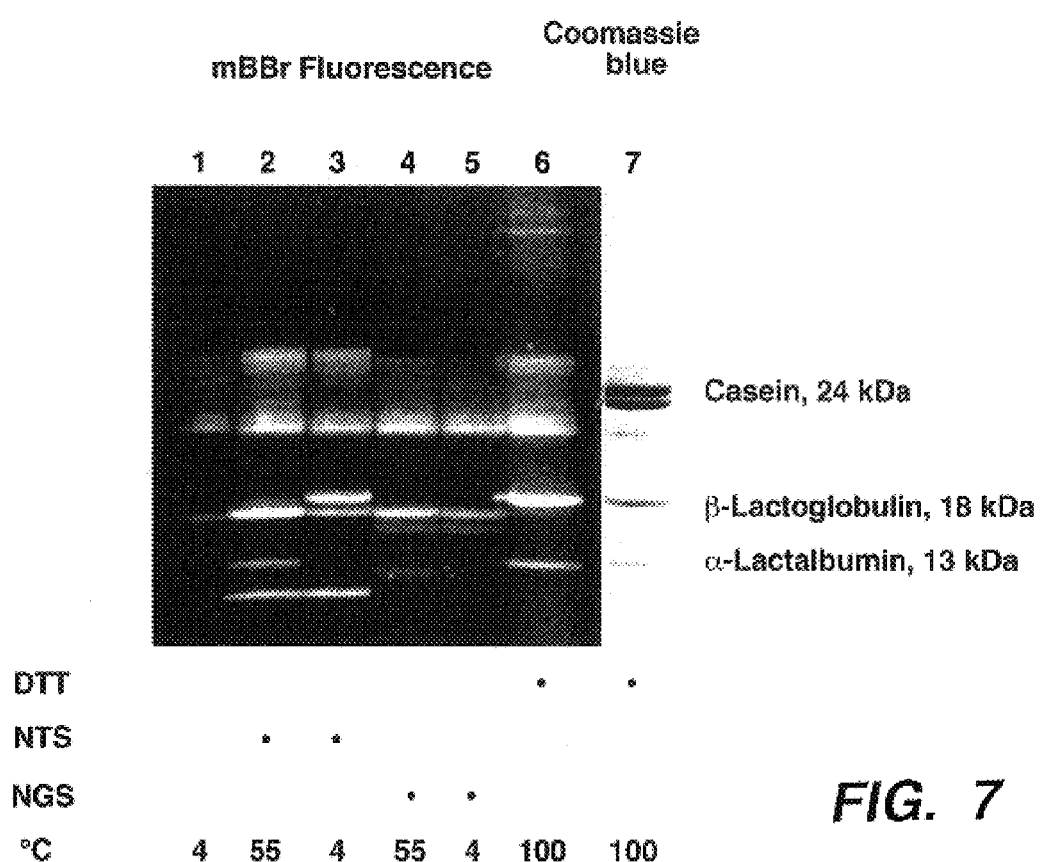
FIG. 7 is a photograph of an SDS polyacrylamide electrophoretic gel showing the extent of thioredoxin-linked and glutathione-linked reduction by means of fluorescence and protein staining.

Temperature was found to have an interesting and useful effect on reduction. When treated at 55° C. (45 min) as shown in FIG. 7, BLG was reduced but its mobility in the gel was only slightly changed. By contrast, when incubated at 4° C. (17 h), the mobility of the bulk of BLG was decreased significantly and a new form of the protein appeared (Lane 3, FIG. 7). An assessment of the extent of reduction by gel scanning revealed that BLG is partly reduced at 55° C. and fully reduced at 4° C. Comparison of the amino acid sequences of the tryptic peptides of the partly and fully reduced forms with the known structure of BLG gave further information on the nature of the reduction.

Figure 8:
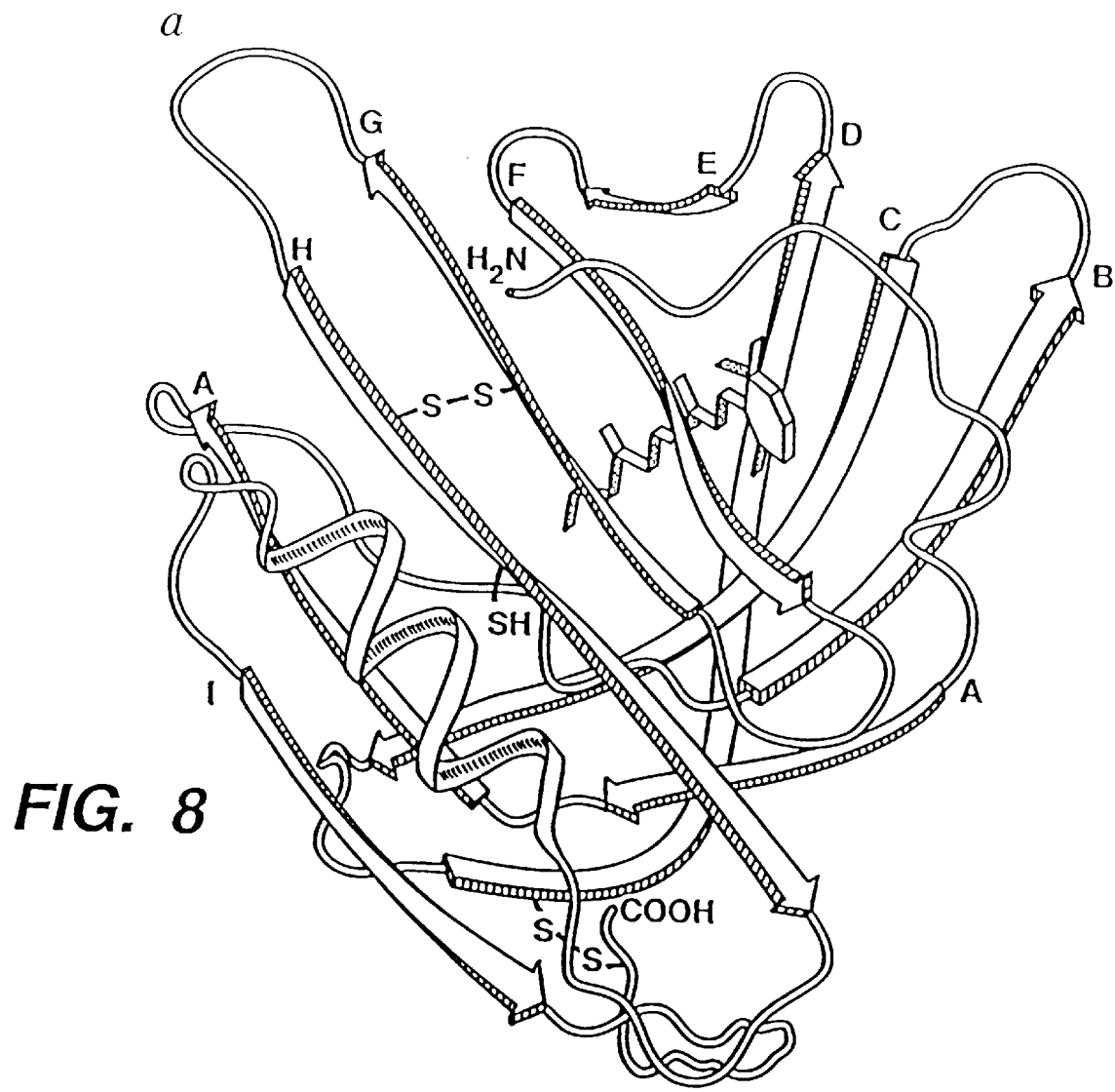
FIG. 8 is a drawing of the tertiary structure of oxidized bovine β-lactoglobulin showing the disulfide bridges and free sulfhydryl.

BLG is known to contain two disulfides, both intramolecular (See, FIG. 8): one clearly accessible on the surface and located close to the C-terminus (Cys 66-Cys 160) and the other, close to the core, located between two β-sheets (Cys 106-Cys 119 or possibly Cys 106-Cys 121). Sequence analysis confirmed that the exposed disulfide (Cys 66-Cys 160) was reduced at 55° C. (partly reduced form) and that this as well as the hidden disulfide (Cys 106-Cys 119 or Cys 106-Cys 121) were both reduced at 4° C. (fully reduced form) (see Materials and Methods). Differential reduction of BLG could also be achieved by altering pH. Reduction at pH 6.8 yielded only the partly reduced form whereas a mixture of the partly and fully reduced forms was observed at pH 8.0 (both at 37° C.) (data not shown). The results confirm the findings of others who showed that BLG was unstable at pH values above neutrality (Tanford, C. et al. (1959), "Transformation of β-Lactoglobulin at pH 7.5", *Biochemistry* 81.4032–4036) and undergoes conformational transitions at temperatures above 40° C. (Qi, X. L. et a. (1997), "Effect of temperature on the secondary structure of beta-lactoglobulin at pH 6.7, as determined by CD and IR spectroscopy: a test of the molten globule hypothesis", *Biochem. J.* 324:341–346). Significantly, the same reduction results for BLG as shown in FIG. 7 were obtained when only the components of the NADP/thioredoxin system were added to raw milk without buffer. Furthermore, the BLG in this treated milk without buffer remained reduced for 2 days when stored at 4° C. in air (data not shown).

As seen in Lanes 4 and 5 of the gel in FIG. 7, the monothiol glutathione maintained in the reduced state by NADPH and glutathione reductase also reduced BLG and to some extent other milk proteins, but less effectively than NTS. Other disulfide reductants, dithiotreitol and lipoic acid, were effective but only when combined with thioredoxin as described in previous Examples for venom neurotoxins (data not shown).

Digestion of Milk Proteins by Pepsin and Trypsin

As shown in Examples 19 and 29, the trypsin sensitivity of small proteins containing intramolecular disulfide bonds (e.g., trypsin inhibitors, venom neurotoxins) increases dramatically following reduction by thioredoxin. Likewise, BLG was seen to follow this same pattern, that is, the thioredoxin-reduced BLG was highly sensitive to trypsin digestion whereas the oxidized BLG (i.e., pure, untreated) was resistant (See, Example 34). Similar results were obtained in this Example with the pure BLG as well as with milk subjected to simulated gastric fluid as described by Astwood, J. D. et al., supra. When separated by SDS-PAGE and stained with Coomassie blue, BLG was found to be digested by pepsin but only after reduction by thioredoxin (See, FIG. 9). FIG. 9 shows the digestion of oxidized and reduced BLG as determined by mini SDS/PAGE and Coomassie blue dye. All incubations with SGF were at 37° C. 13.5 μl of SGF mixture was applied as indicated. The other variables for the gel in FIG. 9 were: Lane 1, BLG, SGF, 0 min; Lane 2, BLG, SGF, 60 min; Lane 3, reduced BLG by NTS at 55° C., SGF, 0 min; Lane 4, reduced BLG by NTS at 55° C., SGF, 60 min; Lane 5, reduced BLG at 4° C., SGF, 0 min; Lane 6, reduced BLG at 55° C., SGF, 60 min; Lane 7, SGF; Lane 8, BLG. As seen in FIG. 9, the difference in sensitivity was striking.

Figure 10A:
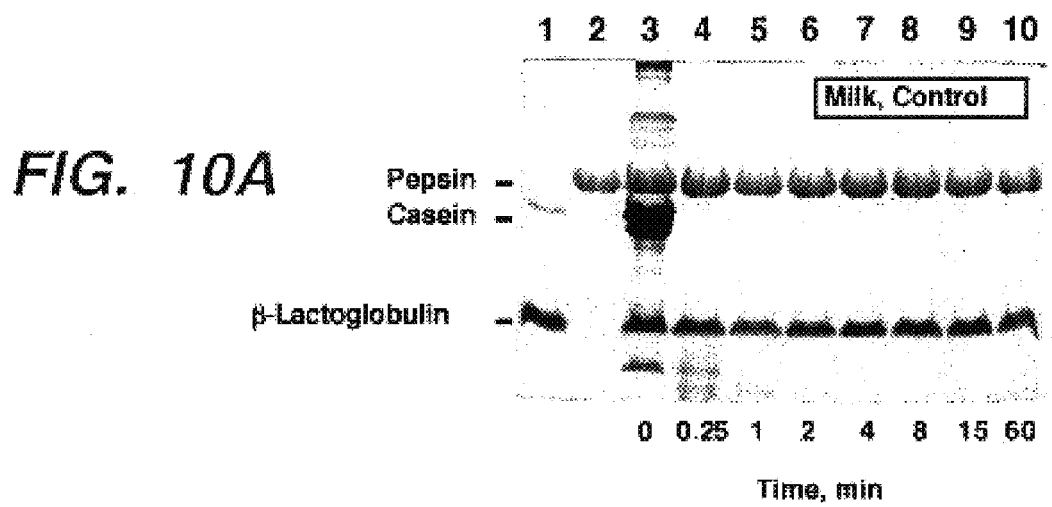
FIG. 10A represents a photograph of a protein stained SDS polyacrylamide electrophoretic gel showing the effect of time on the digestion of untreated milk.
Figure 10B:
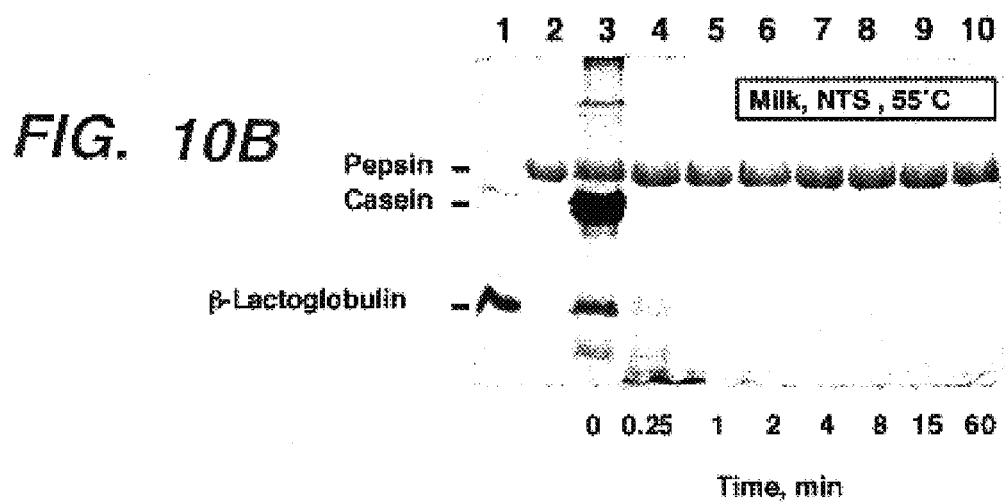
FIG. 10B represents a photograph of a protein stained SDS polyacrylamide electrophoretic gel showing the effect of time on the digestion of milk following thioredoxin-linked reduction that occurred at 55° C.
Figure 10C:
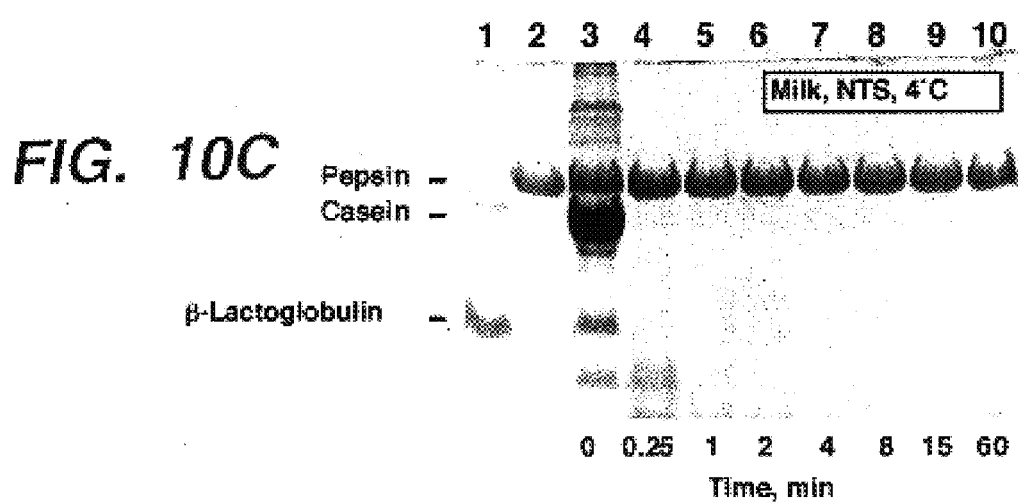
FIG. 10C represents a photograph of a protein stained SDS polyacrylamide electrophoretic gel showing the effect of time on the digestion of milk following thioredoxin-linked reduction that occurred at 4° C.

Oxidized BLG in milk was found to resist digestion for at least 60 min whereas the thioredoxin-reduced form was digested within 60 seconds (See, FIGS. 10A-10C). FIGS. 10A, 10B and 10C depict the effect of time on the digestion of milk buffered in PBS after thioredoxin reduction determined by mini SDS/PAGE and Coomassie blue dye. Samples 2–10 contained 13.5 μl of simulated gastric fluid mixture and samples 3–10 contained 50 μg milk protein. After 0, 0.25, 1, 2, 4, 8, 15, 30, 60 min incubation the digestion was stopped by neutralization and aliquots were applied to the appropriate lanes of each of the gels in FIGS. 10A, 10B and 10C. The other variables for the gel in FIG. 10A were buffered milk control; for the gel in FIG. 10B: buffered milk, NTS, 55° C.; for the gel in FIG. 10C: buffered milk, NTS, 4° C. The reduction of a single disulfide bond was sufficient. The partly (55° C.) and fully (4° C.) reduced forms of BLG showed no difference in pepsin sensitivity (compare FIGS. 10B and 10C). Significantly, even though partially reduced by thioredoxin, the glutathione-treated sample was insensitive to digestion by simulated gastric fluid (data not shown). While the sensitivity of α-lactalbumin and κ-casein were somewhat enhanced by thioredoxin reduction, BLG, either pure or in milk, was found to be the only protein not digested without reduction by thioredoxin (See, FIGS. 7, 9 and 10A-10C).

Allergy Status of Reduced and Digested Milk Proteins

Figure 11A:
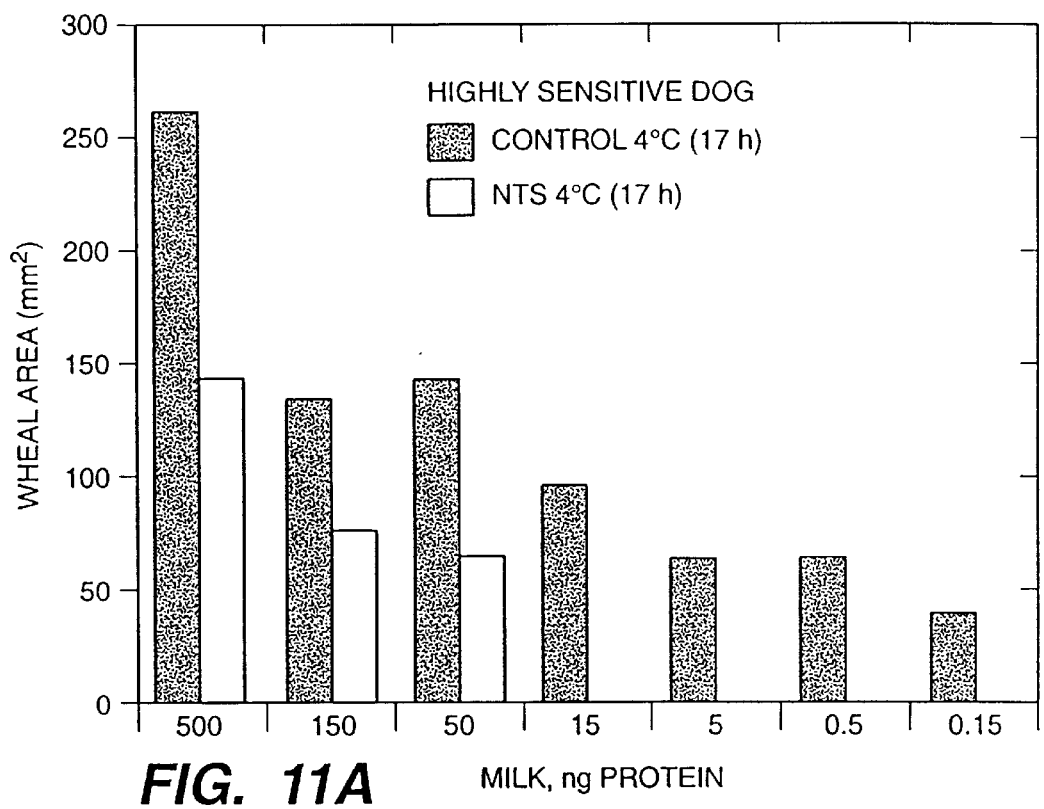
FIG. 11A is a bar graph showing the thioredoxin-linked mitigation of a skin test response in a dog highly sensitive to milk.
Figure 11B:
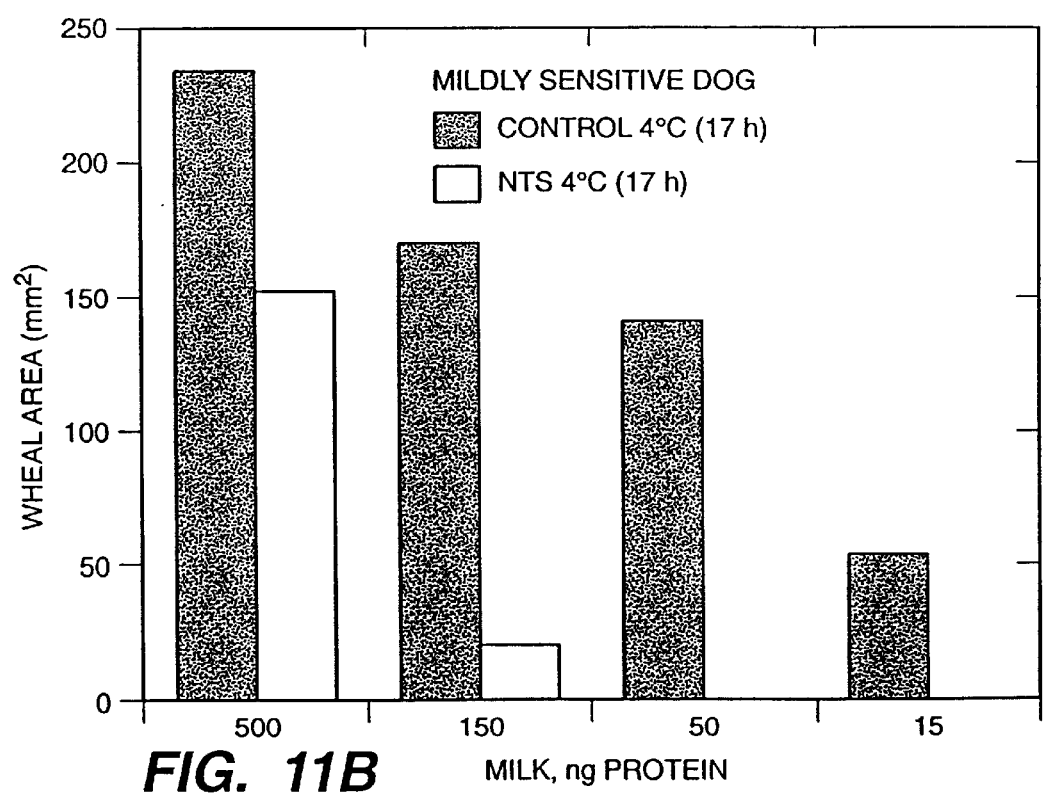
FIG. 11B is a bar graph showing the thioredoxin-linked mitigation of a skin test response in a dog mildly sensitive to milk.

A comparison of the allergenicity of the major proteins of milk (casein, α-lactalbumin, BSA, BLG) using dog model skin tests revealed that BLG is the major allergen of milk, accounting for 80% of the total wheal-inducing activity. Furthermore, when treated with the thioredoxin system, both milk and BLG showed a decreased ability to elicit an allergic response. Thus, similar to the results in the previous Examples testing allergenicity, the allergenicity of raw milk was decreased by a factor of 10 to 300, depending on the sensitivity of the dog tested (See, FIGS. 11A and 11B). The graphs in FIGS. 11A and 11B compare the thioredoxin-linked mitigation of skin test response to raw milk allergens in two dogs of differing sensitivity. The type I hypersensitivity reaction determined by the wheal area ($mM^2$) was induced by 100 μl intradermal injections of milk solution in PBS as indicted in FIGS. 11A and 11B. The solutions were either pretreated with the NADP/thioredoxin system (NTS, 4° C.) or untreated (control). The response of the two dogs is shown to illustrate that despite differences in sensitivity, the thioredoxin treatment mitigated allergenicity in both cases (i.e., for mildly (FIG. 11B) and highly (FIG. 11A) sensitive animals). A PBS/glycerol control and NTS were found to be negative for each dog. Also, tests with a number of dogs showing different sensitivity revealed no consistent difference in the allergenicity of the partly and fully reduced forms of BLG either pure or in milk (data not shown). The skin test data thus show that reduction by thioredoxin alters epitope accessibility such that the allergenicity of BLG and possibly other milk proteins is decreased.

Figure 12A:
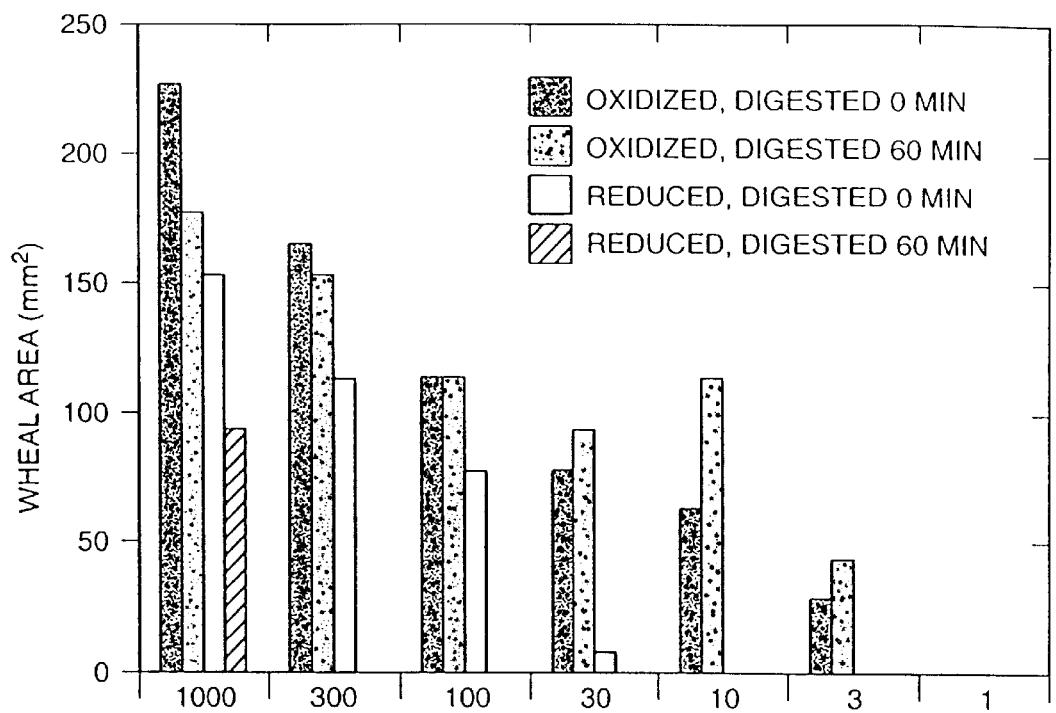
FIG. 12A is a bar graph showing the effect of thioredoxin-linked reduction and digestibility on the allergenicity of β-lactoglobulin.
Figure 12B:
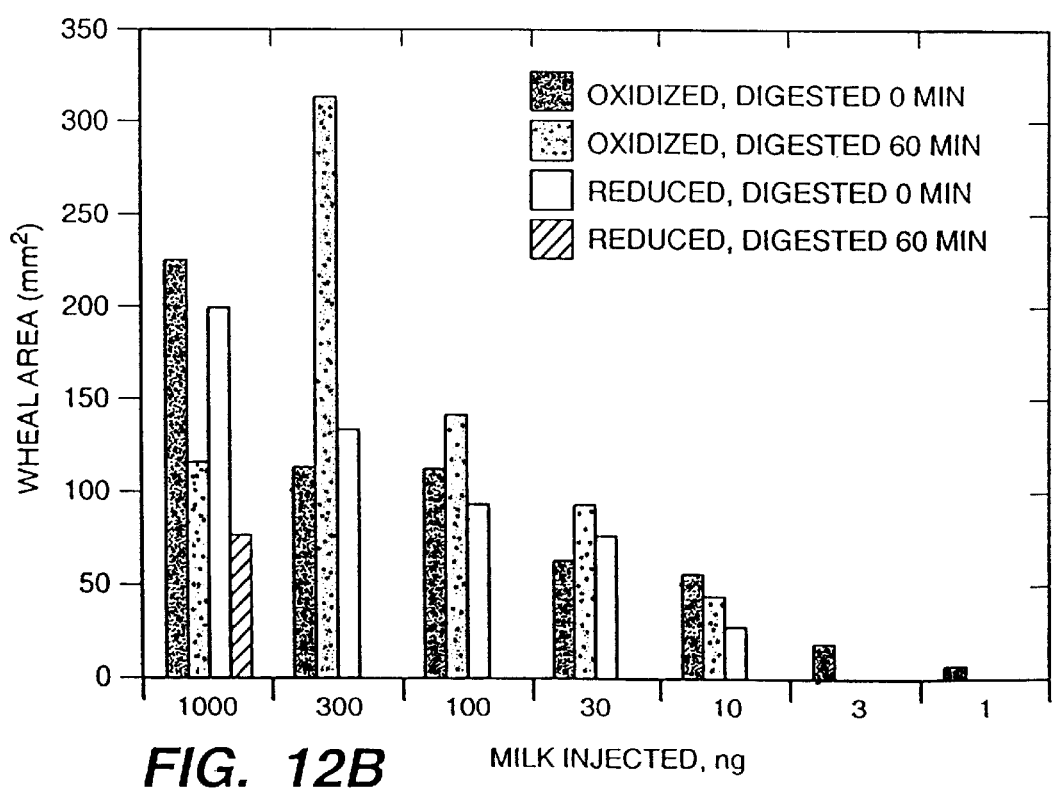
FIG. 12B is a bar graph showing the effect of thioredoxin-linked reduction and digestibility on the allergenicity of milk.

Pure BLG showed an allergenic response similar to milk (compare oxidized and reduced zero time samples in FIGS. 12A and 12B). In FIGS. 12A and 12B, the oxidized "0" min and reduced "0" min bars represent the samples before digestion treatment, the oxidized 60 min and reduced 60 min bars represent samples treated with pepsin containing SGF. The type I hypersensitivity reaction observed by the skin wheal area (mm$^2$) was induced by 100 µl intradermnal injections of digested neutralized BLG (FIG. 12A) or milk (FIG. 12B) either pretreated with the NADP/thioredoxin system (NTS) (reduced) or untreated (oxidized control). A neutraized SGF control was found to be negative for all tested dogs. Furthermore, skin tests showed no difference between the pure A and B forms of BLG with respect to the effect of thioredoxin on allergenicity (data not shown).

Skin tests carried out with both BLG and milk revealed that peptic digestion nearly completely eliminated the allergenicity of both preparations (See FIGS. 12A and 12B). Based on skin tests, the allergy response is decreased by 300 to 1000 when digestion is coupled to reduction. Furthermore, the allergenicity of the digested samples was decreased to marginal levels, in both highly and mildly sensitive dogs.

Figure 13:
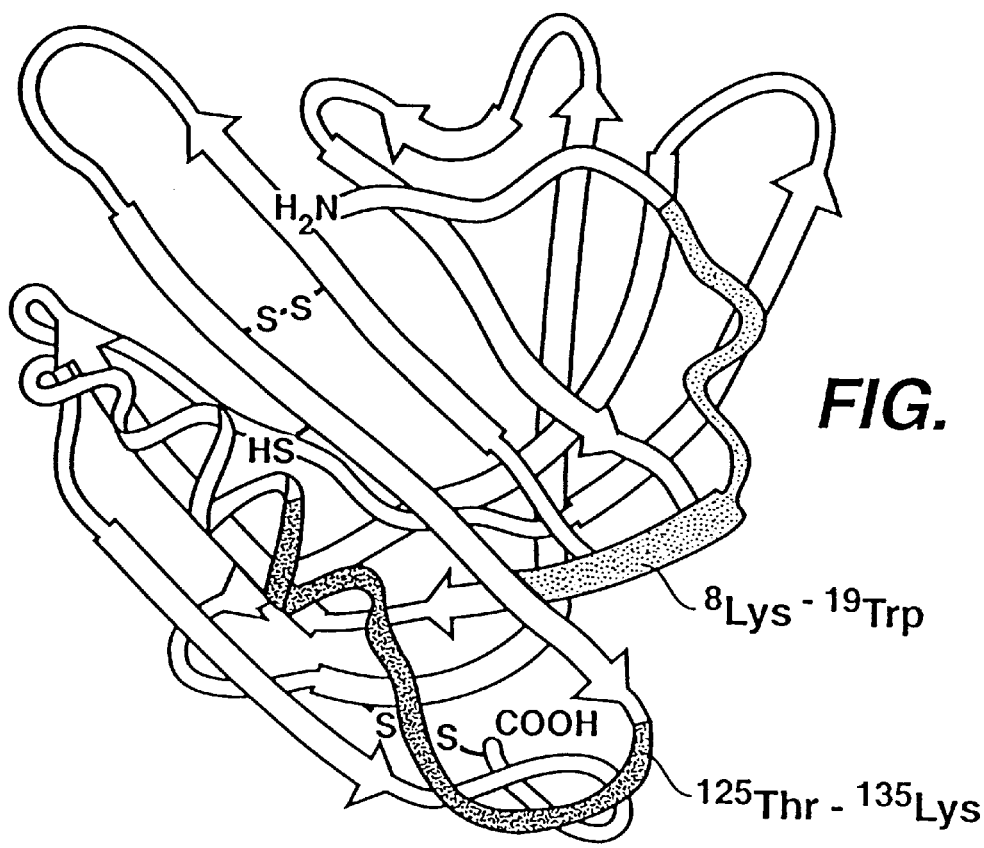
FIG. 13 is a drawing of the tertiary structure of oxidized bovine β-lactoglobulin showing the mouse antibody (MAb) epitopes.
Figure 14:
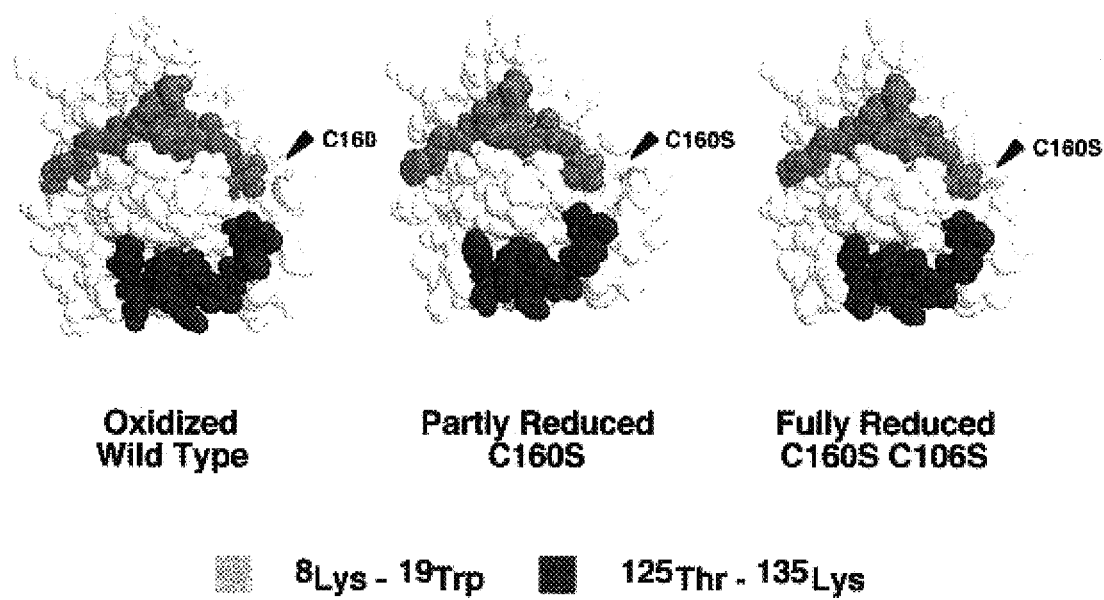
FIG. 14 is a graphic of a computer generated molecular model of the tertiary structure of bovine β-lactoglobulin showing predicted monoclonal antibody epitope changes after cystine mutagenesis.

These results are consistent with the conclusion that reduction by thioredoxin (1) alters the accessibility of the epitopes of intact proteins, so that allergenicity is decreased in most animals, and (2) renders stable allergens such as BLG susceptible to pepsin digestion with the consequent almost complete loss of allergenic properties (see FIGS. 13 and 14).

Finally, it was also found that α-lactalbumin and BLG are digested by trypsin when reduced by the NTS system (See, Example 34). These results, coupled with the results obtained in this example with pepsin, confirm the ability of thioredoxin to render BLG protease sensitive.

Feeding Trials with Atopic Dogs

Upsets in the gastrointestinal tract leading to vomiting and diarrhea are symptoms that accompany the ingestion of food allergens but also the indigestibility of food proteins. Furthermore, the severity of these symptoms provides a measure of the strength of allergens that complements skin tests. To obtain evidence on the gastrointestinal response, the food of sensitive dogs was supplemented with BLG. As shown from the results set forth in Table VIII below, dogs consuming food containing 2.5 gm of reduced BLG (2.5 gm of BLG corresponds to ¾ liter of milk) showed a significantly reduced extent of the vomiting. Repeated feeding trails indicated that, on average, about 70% of the gastric reflux disappeared. Significantly, this pattern was observed in a single set of dogs fed either treated or untreated BLG. A similar alleviation of the associated gastrointestinal upset response was observed by decreasing the BLG from the 2.5 gm used in Table VIII to 1.25 gm per can of food fed to each dog (data not shown). These observations complement the skin test results discussed above in showing that allergen recognition by the mucosal lymphatic tissue is mitigated by treatment with thioredoxin.

TABLE XVIII

Allergic Response of Dogs Alternately Fed
Untreated or Thioredoxin-Treated β-Lactoglobulin

| | Upper GI Index* | | | |
|---|---|---|---|---|
| | Exp. A | | Exp. B | |
| Dog | Control | Treated | Control | Treated |
| 6GCB3 | 7 | — | — | 0 |
| 6GCB7 | 6 | — | — | 3 |
| 6GCB1 | — | 0 | 5 | — |
| 6GCB4 | — | 6 | 9 | — |
| 6GCB6 | — | 0 | 8 | — |

*Measure of quantity and fluidity of induced vomit
Upper GI index response was measured using thioredoxin treated or untreated (control) BLG, 2.5 gm, mixed with one can of dog food. Index calculations were performed after two separate feeding experiments, A and B. Upper GI index quotations were: no vomit = 0, small vomit = 1, large vomit = 2, solid vomit = 1, liquid vomit = 2, liquid vomit with blood or bile = 3, delayed vomit = 1 and immediate vomit = 2.

Discussion

In this Example, thioredoxin was found to reduce specifically the intramolecular disulfide bonds present in BLG, a major milk allergen. Depending on conditions, thioredoxin, reduced by NADPH and NTR reduced either one or both of the disulfide bonds of BLG whether analyzed with pure protein or milk. The change in epitope distribution revealed experimentally by skin tests and feeding challenges was seen at the molecular level in structural models (Peitsch, M. C. (1996), supra.). When the exposed disulfide bond of BLG (Cys66-Cys160) was disrupted by site-directed mutagenesis using a computer model, the $^{125}$Thr-$^{135}$Lys epitope (Kaminogawa, S. et al. (1989), "Monoclonal antibodies as probes for monitoring the denaturation process of bovine β-lactoglobulin", *Biochemica et Biophisica Acta* 998:50–56), which is nearby changed its position significantly whereas the epitope which is distant from both disulfides ($^8$Lys-$^{19}$Trp) did not (See, FIGS. 13 and 14). Mutagenesis of the buried disulfide (Cys106-Cys119 or possibly Cys106-Cys121) led to no further change in the position of the epitope. A similar observation was made with a model prepared with human BLG epitopes (Ball, G. et al. (1994), "A major continuous allergenic epitope of bovine beta-lactoglobulin recognized by human IgE binding", *Clinical and Experimental Allergy* 24:758–764).

The present results suggest that reduction by thioredoxin lowers allergenicity of a target protein allergen in two ways. Reduction effects a change in protein structure that restricts epitope accessibility and enhances digestibility. In this way, the strength of the allergen is decreased and, in addition, should be more rapidly eliminated in the gastrointestinal tract.

EXAMPLE 40

Digestion of Reduced Gliadins by Pepsin and Trypsin

The protease susceptibility of the gliadin fraction isolated by ethanol extraction of wheat flour as described in Examples 9 and 10 was investigated. As shown in previous Example 10, gliadins contain intramolecular disulfide bonds that are specifically reduced by thioredoxin. Gliadins are also a major food allergen in wheat. Buchanan, B. B. et al. (1997), "Thioredoxin-linked mitigation of allergic responses to wheat", *Proc. Nati. Acad. Sci. USA* 94:5372–5377. The thioredoxin itself can be reduced either enzymatically by NADPH and NADP-thioredoxin reductase or chemically by dithiothreitol (DTT). For this Example, aliquots (50 μl) of isolated gliadin (1.04 mg/ml) were incubated with or without thioredoxin (1.0 μg) which was reduced in the presence or absence of 1 mM DTT for an hour at room temperature at pH 7.5 in Tris-HCl buffer. At the end of the incubation, 5 μl of trypsin from Sigma (1 mg/ml) was added to each sample. The samples were subjected to digestion for another hour at 30° C. Digestion was terminated by PMSF (phenylmethylsulfonyl fluoride (2 μl of 100 mM) in each sample. After mixing with SDS (10 μl of 10%) and glycerol (15 μl of 50%), samples were analyzed by SDS-PAGE. After electrophoresis the 15% gel was stained with Coomassie blue and destained by methanol and acetic acid. Analysis of the protein bands demonstrated that the gliadins were stable to digestion in the oxidized (untreated) state but were degraded to lower molecular weight components following reduction by thioredoxin. Similar results were obtained when the gliadin aliquots were treated and digested with pepsin instead of trypsin as in Example 39.

This Example and Examples 34 and 39 show that a consequence of allergen reduction by thioredoxin is the striking increase in sensitivity to proteases. Thus, whereas the oxidized forms of gliadins and BLG were resistant to pepsin, the reduced forms were highly susceptible and were readily digested. The average concentration of innate thioredoxin in wheat flour is about 0.01% (Johnson, T. C. et al. (1987), "Reduction of purothionin by the wheat seed thioredoxin system and potential function as a secondary thiol messenger in redox control", *Plant Physiol.* 85:446–451). This is about 100 mg to about 200 mg per kilogram of flour or in bread, about 2 mg of thioredoxin per 100 gm of flour. However, the upper limit of naturally occurring thioredoxin in flour could be about 2 mg per gram of food protein. Bread, for example, that contained higher concentrations of thioredoxin treated with a thioredoxin reductant would be a less allergenic and more digestible bread. The increase in the sensitivity to pepsin by food proteins treated with thioredoxin and a thioredoxin reductant, seen also at the molecular level through modeling for BLG, would likely lead to a more rapid processing of ingested BLG in the gastrointestinal tract. If extended to the whole animal, treatment of milk and wheat and other food products with the thioredoxin system would be expected to provide relief from the long-term effects of allergenicity and indigestibility—notably edema and diarrhea.

Commercialization of the thioredoxin technology with respect to milk could be achieved by treating milk with the NTS before or after pasteurization (i.e., at 55° C. for 45 min or at 4° C. for at least 10 hr). Such applications might include the following:

1. Applying the thioredoxin system in liquid form to raw milk or whey and coupling reduction to the pasteurization process.
2. Passing raw or pasteurized milk through a column of bound reduced thioredoxin The thioredoxin could be reduced with NADPH and NTR prior to application of the milk. The thioredoxin could also possibly be reduced with dithiothreitol which could be removed from the column by washing prior to application of the milk
3. Storing NTS treated milk under non-oxidizing conditions to increase shelf life by using for example full or evacuated containers.
4. Adding thioredoxin and NTR to milk after pasteurization and adding NADPH in solid form just prior to use.
5. After treatment with thioredoxin, subjecting milk to limited proteolytic digestion with enzymes such as trypsin. Such product could be used to induce tolerance in milk-sensitive individuals.

CONCLUDING REMARKS

It can be seen from the foregoing general description of the invention and from the specific examples illustrating applications thereof, that the invention has manifold and far reaching consequences. The invention basically provides novel dough and dough mixtures and novel methods for creating new doughs and for improving the quality of dough and baked goods as well as novel methods for inactivating enzyme inhibitors in cereal products. The invention also provides a novel method for altering the biological activity and inactivity of animal toxins, and for eliminating or decreasing the allergenicity of several foods, namely wheat, egg, milk, whey, soy, nuts and beef and for increasing the proteolysis and digestibility of foods, particularly milk, whey and their products and wheat products. The invention further provides a novel protein that is a pullulanase inhibitor and a method for its inactivation.

While the invention has described in connection with certain specific embodiments thereof, it should be realized that various modifications as may be apparent to those of skill in the art to which the invention pertains also fall within the scope of the invention as defined by the appended claims.

What is claimed is:

1. A hyperdigestible food product containing added thioredoxin and nicotinamide adenine dinucleotide phosphate-thioredoxin reductase; and further containing NADP that resulted from added NADPH, wherein said food is more susceptible to pepsin digestion than the same food without added thioredoxin, nicotinamide adenine dinucleotide phosphate-thioredoxin reductase, and NADPH.

2. A food containing more than 2 mg thioredoxin per gram of protein in said food.

3. A hyperdigestible food that has been treated with thioredoxin, nicotinamide adenine dinucleotide phosphate-thioredoxin reductase and NADPH, wherein said food is more susceptible to pepsin digestion than the same food without treatment.

4. Hyperdigestible milk that has been treated with thioredoxin, nicotinamide adenine dinucleotide phosphate-thioredoxin reductase and NADPH.

5. A hyperdigestible food or food product that has been treated with thioredoxin and dithiothreitol, wherein said food or food product is more susceptible to pepsin digestion than the same food or food product without treatment.

* * * * *